United States Patent [19]

Yamada et al.

[11] Patent Number: 5,770,344
[45] Date of Patent: Jun. 23, 1998

[54] SILVER HALIDE PHOTOGRAPHIC LIGHT-SENSITIVE MATERIAL

[75] Inventors: Kohzaburoh Yamada; Hiroyuki Suzuki; Toshihide Ezoe, all of Kanagawa, Japan

[73] Assignee: Fuji Photo Film Co., Ltd., Kanagawa, Japan

[21] Appl. No.: 774,227

[22] Filed: Dec. 27, 1996

[30] Foreign Application Priority Data

Dec. 27, 1995 [JP] Japan .................................... 7-351279
Dec. 27, 1995 [JP] Japan .................................... 7-351287
Oct. 25, 1996 [JP] Japan .................................... 8-299877

[51] Int. Cl.$^6$ ...................................................... G03C 1/73
[52] U.S. Cl. ............................................................. 430/264
[58] Field of Search .............................................. 430/264

[56] References Cited

U.S. PATENT DOCUMENTS 5,212,045  5/1993  Koga et al. ............................. 430/264
5,279,920  1/1994  Onodera et al. ....................... 430/264
5,378,578  1/1995  Hoshimiya et al. .................... 430/264

FOREIGN PATENT DOCUMENTS

A10736798  10/1996  European Pat. Off. .
6486134   3/1989  Japan .
416938   1/1992  Japan .
5142688   6/1993  Japan .
5197091   6/1993  Japan .
WO9532453  11/1995  WIPO .

Primary Examiner—Hoa Van Le
Attorney, Agent, or Firm—Sughrue, Mion, Zinn, Macpeak & Seas, PLLC

[57] ABSTRACT

A silver halide photographic light-sensitive material containing a hydrazide compound represented by the following formula (I), (II), (I') or (II'):

$$A_1-(B)b_1 \qquad (I)$$

$$L_0-\{A_2-(B)b_2\}m_1 \qquad (II)$$

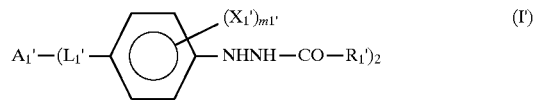

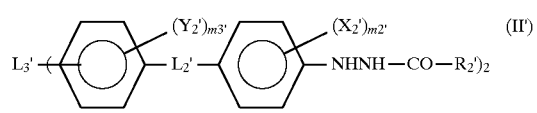

wherein the symbols in the above formulae are defined in the specification.

3 Claims, No Drawings

SILVER HALIDE PHOTOGRAPHIC LIGHT-SENSITIVE MATERIAL

FIELD OF THE INVENTION

The present invention relates to a silver halide photographic light-sensitive material containing a hydrazide compound having a specific structure.

BACKGROUND OF THE INVENTION

In the field of graphic art, in order to obtain good reproduction of a halftone image in continuous gradation or of a line work, an image formation system exhibiting an ultrahigh contrast (particularly having a γ value of 10 or more) photographic property is required. An image formation system of performing development with a processing solution having good storage stability and providing an ultrahigh contrast photographic property is demanded. To cope with it, a system for forming an ultrahigh contrast negative image having a γ value exceeding 10 by processing a surface latent image-type silver halide photographic light-sensitive material having incorporated therein a specific acylhydrazine compound with a developer containing 0.15 mol/l or more of a sulfite preservative and having a pH of 11.0 to 12.3 has been proposed as described in U.S. Pat. Nos. 4,166,742, 4,168,977, 4,221,857, 4,224,401, 4,243,739, 4,272,606 and 4,311,781. This new image formation system is characterized in that silver iodobromide or silver chloroiodobromide can be used, though only silver chlorobromide having a high silver chloride content can be used in conventional ultrahigh contrast image formation methods. This system is also characterized in that although conventional lith developers can contain a very small amount of sulfite preservative, the developer can contain a large amount of sulfite preservative, and therefore has relatively good storage stability. However, if the developer has a pH of 11 or more, it is readily air oxidized and unstable and cannot withstand storage or use for a long period of time. Accordingly, attempts have been made to develop a silver halide light-sensitive material containing a hydrazine compound with a developer having a lower pH to form a high contrast image. JP-A-1-179939 (the term "JP-A" as used herein means an "unexamined published Japanese patent application") and JP-A-1-179940 disclose a method for processing a light-sensitive material which contains a nucleation development accelerator having an adsorptive group to a silver halide emulsion grain and a nucleating agent having the same adsorptive group, with a developer having a pH of 11.0 or less. However, since the emulsion used in these inventions is a silver bromide or silver iodobromide emulsion, change in the development progressiveness or in the photographic capabilities due to change in the composition of processing solutions is large and the stability thereof is inadequate.

U.S. Pat. Nos. 4,998,604, 4,994,365 and 4,975,354 disclose a hydrazine compound having an ethylene oxide repeating unit or a hydrazine compound having a pyridinium group. However, in the Examples, the contrast is inadequate and it is difficult in these inventions to achieve high contrast and required Dmax under practical development conditions. Further, the nucleation contrast light-sensitive material using a hydrazine derivative undergoes large change in the photographic properties accompanying the change in the pH of the developer. The pH of the developer greatly changes, more specifically, the pH increases due to oxidation of the developer by air or due to thickening resulting from evaporation of water, or decreases due to absorption of carbon dioxide in air. Accordingly, attempts have been made to reduce dependency of the photographic capabilities upon the pH of the developer.

In general, dot-to-dot work light-sensitive materials capable of handling in a bright room are predominating as one of light-sensitive materials for plate-making processing and, in this field, high letter image quality is required so that lean chinese letters of Mincho style can be reproduced. Accordingly, development of nucleating agents having higher activity has been demanded. Particularly, in light-sensitive materials for the bright room which has low sensitivity so as to be handled even in a bright room, the contrast-enhancing effect of the nucleating agents is unwilling to be caused. Therefore, nucleating agents having higher activity have been demanded.

To achieve these objects, for example, JP-A-6-148828, JP-A-6-180477 and JP-A-6-194774 disclose highly active hydrazine-base nucleating agents.

The nucleating agent having a substituted alkyl group substituted by at least one electron withdrawing group as an acyl group is particularly excellent because extremely high contrast photographic property can be obtained even with a developer having a pH of 11 or less and because change in the photographic capabilities due to fatigue of the developer is small. However, in some cases, the nucleating agent itself is readily oxidized and the storability is in need of much improvement.

JP-A-64-86134, JP-A-4-16938 and JP-A-5-197091 disclose compounds having two hydrazino groups incorporated into the molecule. In particular, JP-A-5-197091 discloses some compounds superior in the contrasting capability to conventional acylhydrazine compounds having the same acyl group. However, these are still insufficient in terms of the contrast obtained with a developer having a pH of 11 or less, the stability against fluctuation factor of the processing solutions, and the storability. Accordingly, improvements thereof are needed.

On the other hand, a method for obtaining a direct positive image by surface developing an internal latent image-type silver halide photographic emulsion in the presence of a nucleating agent, and a photographic emulsion or light-sensitive material for use in the method are known, for example, in U.S. Pat. Nos. 2,456,953, 2,497,875, 2,497,876, 2,588,982, 2,592,250, 2,675,318, 3,227,552 and 3,317,322, British Patents 1,011,062, 1,151,363, 1,269,640 and 2,011,391, JP-B-43-29405 (the term "JP-B" as used herein means an "examined Japanese patent publication"), JP-B-49-38164, JP-A-53-16623, JP-A-53-137133, JP-A-54-37732, JP-A-54-40629, JP-A-54-74536, JP-A-54-74729, JP-A-55-52055 and JP-A-55-90940.

In the above-described method for obtaining a direct positive image, a nucleating agent may be added to the developer, however, a method of adding the nucleating agent to the photographic emulsion layer or other appropriate layer of the light-sensitive material is more commonly used.

As the nucleating agent added to the direct positive silver halide light-sensitive material, hydrazine compounds are most well known and specific examples thereof include those described in *Research Disclosure*, No. 23510 (November, 1953), ibid., No. 15162, Vol. 151 (November, 1976), ibid., No. 17626, Vol. 176 (December, 1978). In general, the hydrazine-base nucleating agent provides large difference between the maximum density (Dmax) and the minimum density (Dmin) and is excellent in the point of discrimination, however, it is deficient in that a high pH (11 or more) is required in the processing, and still in need of improvement in this point.

U.S. Pat. No. 5,252,426 discloses hydrazide compounds having a difluoroacetyl group or monofluoroacetyl group as an acyl group. However, these compounds do not have sufficient properties in terms of nucleation contrasting capability.

On the other hand, Japanese Patent 3-125134 discloses hydrazide compounds having a difluoroacetyl group. However, these compounds do not exhibit sufficient nucleating capability.

SUMMARY OF THE INVENTION

Accordingly, a first object of the present invention is to provide a silver halide photographic light-sensitive material capable of achieving extremely high contrast photographic property having a γ value exceeding 10 using a stable developer.

A second object of the present invention is to provide a silver halide photographic light-sensitive material for plate making, which has high processing stability and excellent storability.

A third object of the present invention is to provide a direct positive light-sensitive material capable of exhibiting sufficiently high reversibility even with a developer having a low pH and a small addition amount of a hydrazide compound.

A fourth object of the present invention is to provide a hydrazide compound having a specific structure useful in achieving these objects.

Other objects and effects of the present invention will be apparent from the following description.

In a first embodiment, the present invention relates to a silver halide photographic light-sensitive material containing a hydrazide compound represented by the following formula (I) or (II):

$$A_1\text{-}(B)b_1 \tag{I}$$

$$L_0\text{-}\{A_2\text{-}(B)b_2\}m_1 \tag{II}$$

wherein $A_1$ represents a substituted or unsubstituted benzene ring, $A_2$ represents an arylene group, B represents a group represented by the following formula (III), $b_1$ represents an integer of from 3 to 6, $L_0$ represents a di-, tri-, tetra-, penta- or hexavalent linking group, $b_2$ represents an integer of from 1 to 5, and $m_1$ represents an integer of from 2 to 6, provided that when $b_2$ is 1, $m_1$ represents an integer of from 3 to 6:

$$-L_1-Ar_1-NHNH-G_1-R_1 \tag{III}$$

wherein $G_1$ represents a carbonyl group, an oxalyl group, a sulfonyl group or a phosphoryl group, $R_1$ represents a hydrogen atom or a block group, $Ar_1$ represents an aromatic group and $L_1$ represents a linking group.

In a second embodiment, the present invention relates to a hydrazide compound represented by the following formula (I') or (II') and a silver halide photographic light-sensitive material containing the same:

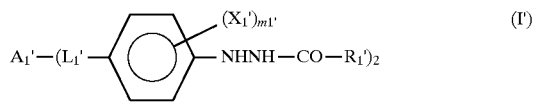

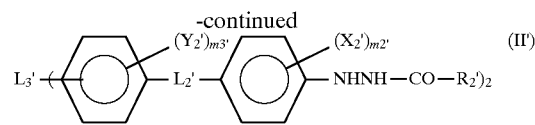

wherein $A_1'$ represents a substituted or unsubstituted benzene ring, $L_1'$, $L_2'$ and $L_3'$ each represents a divalent linking group, $X_1'$, $X_2'$ and $Y_2'$ each represents a substituent, $m_1'$, $m_2'$ and $m_3'$ each represents an integer of from 0 to 4, $R_1'$ and $R_2'$ each represents a hydrogen atom or a block group, provided that at least one of two $R_1'$ groups in formula (I') and at least one of two $R_2'$ groups in formula (II') each represents a substituted alkyl group substituted by one or more fluorine atoms.

In a preferred embodiment, at least one of two $L_1'$ groups in formula (I') and at least one of two $L_2'$ groups in formula (II') each is an —SO$_2$NH group.

In another preferred embodiment, at least one of two $R_1'$ groups in formula (I') and at least one of two $R_2'$ groups in formula (II') each is a trifluoromethyl group or a difluoromethyl group.

DETAILED DESCRIPTION OF THE INVENTION

The term "substituent" as used in the present invention means a halogen atom or a substituent bonded to the ring or main chain through a carbon atom, an oxygen atom, a nitrogen atom or a sulfur atom. Examples of the substituent bonded through a carbon atom include an alkyl group, an alkenyl group, an alkynyl group, an aryl group, a carbamoyl group, an alkoxycarbonyl group, an aryloxycarbonyl group, an acyl group, an acylcarbamoyl group, a sulfonylcarbamoyl group, a carboxyl group and a salt thereof, a cyano group and a heterocyclic group. Examples of the substituent bonded through an oxygen atom include a hydroxy group, an alkoxy group, an aryloxy group, a heterocyclic oxy group, an acyloxy group, a carbamoyloxy group and a sulfonyloxy group. Examples of the substituent bonded through a nitrogen atom include an acylamino group, an amino group, an alkylamino group, an arylamino group, a heterocyclic amino group, a ureido group, a sulfamoylamino group, an alkoxycarbonylamino group, an aryloxycarbonylamino group, a sulfonamido group, an imido group and a heterocyclic group. Examples of the substituent bonded through a sulfur atom include an alkylthio group, an arylthio group, a heterocyclic thio group, a sulfamoyl group, an acylsulfamoyl group, an alkoxysulfonyl group, an aryloxysulfonyl group, a sulfonyl group, a sulfo group and a salt thereof, and a sulfinyl group. These substituents each may further be substituted.

The substituent is described in more detail below. Examples of the halogen atom include a fluorine atom, a chlorine atom and a bromine atom. The alkyl group is a linear, branched or cyclic alkyl group having from 1 to 16, preferably from 1 to 10 carbon atoms and examples thereof include methyl ethyl, isopropyl, t-butyl, benzyl and cyclopentyl. The alkenyl group is an alkenyl group having from 2 to 16 carbon atoms and examples thereof include vinyl, 1-propenyl, 1-hexenyl and styryl. The alkynyl group is an alkynyl group having from 2 to 16 carbon atoms and examples t hereof include ethynyl, 1-butynyl, 1-dodecenyl and phenylethyl. The aryl group is an aryl group having from 6 to 24 carbon atoms and examples thereof include phenyl, naphthyl and p-methoxyphenyl.

The carbamoyl group is a carbamoyl group having from 1 to 18 carbon atoms and examples thereof include carbamoyl, N-ethylcarbamoyl, N-octylcarbamoyl and N-phenylcarbamoyl. The alkoxycarbonyl group is an alkoxycarbonyl group having from 2 to 18 carbon atoms and examples thereof include methoxycarbonyl and benzyloxycarbonyl. The aryloxycarbonyl group is an aryloxycarbonyl group having from 7 to 18 carbon atoms and examples thereof include phenoxycarbonyl. The acyl group is an acyl group having from 1 to 18 carbon atoms and examples thereof include acetyl and benzoyl. The heterocyclic group bonded through a carbon atom on a ring is a 5- or 6-membered, saturated or unsaturated heterocyclic ring having from 1 to 5 carbon atoms and containing one or more hetero atoms selected from an oxygen atom, a nitrogen atom and sulfur atom, in which the number and the kind of the element of the hetero atoms constituting the ring may be one or in plurality, and examples thereof include 2-furyl, 2-thienyl, 2-pyridyl and 2-imidazolyl. The acylcarbamoyl group is an acylcarbamoyl group having from 1 to 18 carbon atoms and examples thereof include N-acetylcarbmoyl and N-benzoylcarbamoyl. The sulfonylcarbamoyl group is a sulfonylcarbamoyl group having from 1 to 18 carbon atoms and examples thereof include N-methanesulfonylcarbamoyl and N-benzenesulfonylcarbamoyl.

The alkoxy group is an alkoxy group having from 1 to 16, preferably from 1 to 10 carbon atoms and examples thereof include methoxy, 2-methoxyethoxy and 2-methanesulfonylethoxy. The aryloxy group is an aryloxy group having from 6 to 24 carbon atoms and examples thereof include phenoxy, p-methoxyphenoxy, m-(3-hydroxypropionamido)phenoxy. The heterocyclic oxy group is a 5- or 6-membered, saturated or unsaturated heterocyclic oxy group having from 1 to 5 carbon atoms and containing one or more hetero atoms selected from an oxygen atom, a nitrogen atoms and a sulfur atom, in which the number and the kind of the element of the hetero atoms constituting the ring may be one or in plurality, and examples thereof include 1-phenyltetrazolyl-5-oxy, 2-tetrahydropyranyloxy and 2-pyridyloxy. The acyloxy group is an acyloxy group having from 1 to 16, preferably from 1 to 10 carbon atoms and examples thereof include acetoxy, benzoyloxy and 4-hydroxybutanoyloxy. The carbamoyloxy group is a carbamoyloxy group having from 1 to 16, preferably from 1 to 10 carbon atoms and examples thereof include N,N-dimethylcarbamoyloxy, N-hexylcarbamoyloxy and N-phenylcarbamoyloxy. The sulfonyloxy group is a sulfonyloxy group having from 1 to 16 carbon atoms and examples thereof include methanesulfonyloxy and benzenesulfonyloxy.

The acylamino group is an acylamino group having from 1 to 16, preferably from 1 to 10 carbon atoms and examples thereof include acetamido and p-chlorobenzoylamido. The alkylamino group is an alkylamino group having from 1 to 16, preferably from 1 to 10 carbon atoms and examples thereof include N,N-dimethylamino and N-(2-hydroxyethyl) amino. The arylamino group is an arylamino group having from 6 to 24 carbon atoms and examples thereof include anilino and N-methylanilino. The heterocyclic amino group is a 5- or 6-membered, saturated or unsaturated heterocyclic amino group having from 1 to 5 carbon atoms and containing one or more hetero atoms selected from an oxygen atom, a nitrogen atom and a sulfur atom, in which the number and the kind of the element of the hetero atoms constituting the ring may be one or in plurality, and examples thereof include 2-oxazolylamino, 2-tetrahydropyranylamino and 4-pyridylamino. The ureido group is a ureido group having from 1 to 16, preferably from 1 to 10 carbon atoms and examples thereof include ureido, methylureido, N,N-diethylureido and 2-methanesulfonamidoethylureido.

The sulfamoylamino group is a sulfamoylamino group having from 0 to 16, preferably from 0 to 10 carbon atoms and examples thereof include methylsulfamoylamino and 2-methoxyethylsulfamoylamino. The alkoxycrbonylamino group is an alkoxycarbonylamino group having from 2 to 16, preferably from 2 to 10 carbon atoms and examples thereof include methoxycarbonylamino. The aryloxycarbonylamino group is an aryloxycarbonylamino group having from 7 to 24 carbon atoms and examples thereof include phenoxycarbonylamino and 2,6-dimethoxyphenoxycarbonylamino. The sulfonamido group is a sulfonamido group having from 1 to 16, preferably from 1 to 10 carbon atoms and examples thereof include methanesulfonamido and p-toluenesulfonamido. The imido group is an imido group having from 4 to 16 carbon atoms and examples thereof include N-succinimido and N-phthalimido. The oxamoylamino group is an oxamoylamino group having from 2 to 16, preferably from 2 to 10 carbon atoms and examples thereof include N-ethyloxamoylamino. The heterocyclic group bonded through a nitrogen atom on a ring is a 5- or 6-membered heterocyclic ring consisting of a nitrogen atom and at least one of carbon atom, oxygen atom and sulfur atom and examples thereof include pyrrolidino, morpholino and imidazolino.

The alkylthio group is an alkylthio group having from 1 to 16, preferably from 1 to 10 carbon atoms and examples thereof include methylthio and 2-phenoxyethylthio. The arylthio group is an arylthio group having from 6 to 24 carbon atoms and examples thereof include phenylthio and 2-carboxyphenylthio. The heterocyclic thio group is a 5- or 6-membered, saturated or unsaturated heterocyclic thio group having from 1 to 5 carbon atoms and containing one or more hetero atoms selected from an oxygen atom, a nitrogen atom and a sulfur atom, in which the number and the kind of the element of the hetero atoms constituting the ring may be one or in plurality, and examples thereof include 2-benzothiazolylthio and 2-pyridylthio.

The sulfamoyl group is a sulfamoyl group having from 0 to 16, preferably from 0 to 10 carbon atoms and examples thereof include sulfamoyl, methylsulfamoyl and phenylsulfamoyl. The alkoxysulfonyl group is an alkoxysulfonyl group having from 1 to 16, preferably from 1 to 10 carbon atoms and examples thereof include methoxysulfonyl. The aryloxysulfonyl group is an aryloxysulfonyl group having from 6 to 24, preferably from 6 to 12 carbon atoms and examples thereof include phenoxysulfonyl. The sulfonyl group is a sulfonyl group having from 1 to 16, preferably from 1 to 10 carbon atoms and examples thereof include methanesulfonyl and benzenesulfonyl. The sulfinyl group is a sulfinyl group having from 1 to 16, preferably from 1 to 10 carbon atoms and examples thereof include methanesulfinyl and benzenesulfinyl. The acylsulfamoyl group is an acylsulfamoyl group having from 1 to 18, preferably from 1 to 16 carbon atoms and examples thereof include N-acetylsulfamoyl and N-benzoylsulfamoyl.

First, the hydrazide compound for use in the silver halide photographic light-sensitive material according to the first embodiment of the present invention are described in detail below.

In formula (I), $A_1$ represents a substituted or unsubstituted benzene ring. The substituent of the benzene ring represented by $A_1$ is preferably a hydroxy group, a halogen atom, an alkyl group, an aryl group, a carbamoyl group, an alkoxycarbonyl group, an aryloxycarbonyl group, an acyl group, a cyano group, an alkoxy group, an aryloxy group, a carbamoyloxy group, an acylamino group, a ureido group, a sulfamoylamino group, an alkoxycarbonylamino group, a sulfonamido group, a sulfamoyl group or a sulfonyl group, more preferably a halogen atom, an alkyl group, an aryl group, a carbamoyl group, an alkoxy group, an aryloxy group, an acylamino group, a ureido group, a sulfonamido group or a sulfamoyl group.

The compound represented by formula (I) may have an adsorption accelerator to silver halide as a substituent.

Examples of the adsorption accelerator to silver halide include those described in U.S. Pat. Nos. 4,385,108 and 4,459,347, JP-A-59-195233, JP-A-59-200231, JP-A-59-201045, JP-A-59-201046, JP-A-59-201047, JP-A-59-201048, J-A-59-201049, JP-A-61-170733, JP-A-61-270744, JP-A-62-948, JP-A-63-234244, JP-A-63-234245 and JP-A-63-234246, such as a thiourea group, a heterocyclic thioamide group, a mercapto heterocyclic group and a triazole group.

Specific examples of preferred adsorption accelerators to silver halide include thioureido, thioamide, thiourethane, 5-mercaptotetrazole, 3-mercapto-1,2,4-triazole, 2-mercapto-1,3,4-thiadiazole, 2-mercapto-1,3,4-oxadiazole, alkylmercapto, arylmercapto and benzotriazole.

In formula (II), $A_2$ represents an arylene group.

The arylene group is a monocyclic or condensed ring arylene group and specific examples thereof include a substituted or unsubstituted phenylene group and a naphthylene group.

When $A_2$ has a substituent, the substituent include those described as the substituent of $A_1$ in formula (I) and the preferred examples thereof are also the same.

In formula (II), $A_2$ is preferably a substituted or unsubstituted phenylene group.

In formula (II), the di-, tri-, tetra-, hepta- or hexavalent linking group represented by $L_0$ is a di-, tri-, tetra-, hepta- or hexavalent group consisting of a combination of groups selected from an alkylene group, a cycloalkylene group, an alkenylene group, an alkynylene group, a phenylene group, —O—, —S—, —N($R_N$)— (wherein $R_N$ represents a single bond, a hydrogen atom, an alkyl group or an aryl group), —CO—, —C(=S)—, —C(=N—$R_N$)—, —SO$_2$—, —SO—, —P(=O)— and —N($R_N$)N($R_N$)—.

The alkylene group is a linear or branched, substituted or unsubstituted alkylene group and specific examples thereof include a methylene group, an ethylene group, a propylene group, a hexafluoropropylene group and an a-ethylmethylene group. The cycloalkylene group is a mono-, bi- or tricyclic, substituted or unsubstituted cycloalkylene group and specific examples thereof include a cyclohexylene group, a bicyclohexylene group, an adamantylene group, a norbornylene group and a decalin-2,6-diyl group. The alkenylene group is a substituted or unsubstituted alkenylene group and specific examples thereof include a vinylene group, a 1,3-butadien-1,4-diyl group and a tetrafluorovinylene group. The alkynylene group is a substituted or unsubstituted alkynylene group and specific examples thereof include an ethynylene group. The phenylene group is a substituted or unsubstituted phenylene group.

However, the compound represented by formula (I) or (II) does not contain a partial structure of biphenyl, diphenylmethane (including bisphenol), triphenylmethane, benzophenone, triphenylamine, diphenylether, diphenylsulfide, diphenylsulfone, stilbene, fluorenone, anthraquinone, binaphthyl or dinaphthylether. Further, in the case of a diphenylamino group, when the group represented by B in formula (I) or (II) is not linked directly or indirectly to the nitrogen atom, the compound does not have a partial structure of a diphenylamino group.

When the group represented by $L_0$ has a substituent, the substituent includes those described as the substituent of $A_1$ in formula (I) and the preferred examples thereof are also the same.

Specific examples of the di- to hexa-valent linking groups represented by $L_0$ in formula (II) are set forth below.

Examples of the divalent linking group:

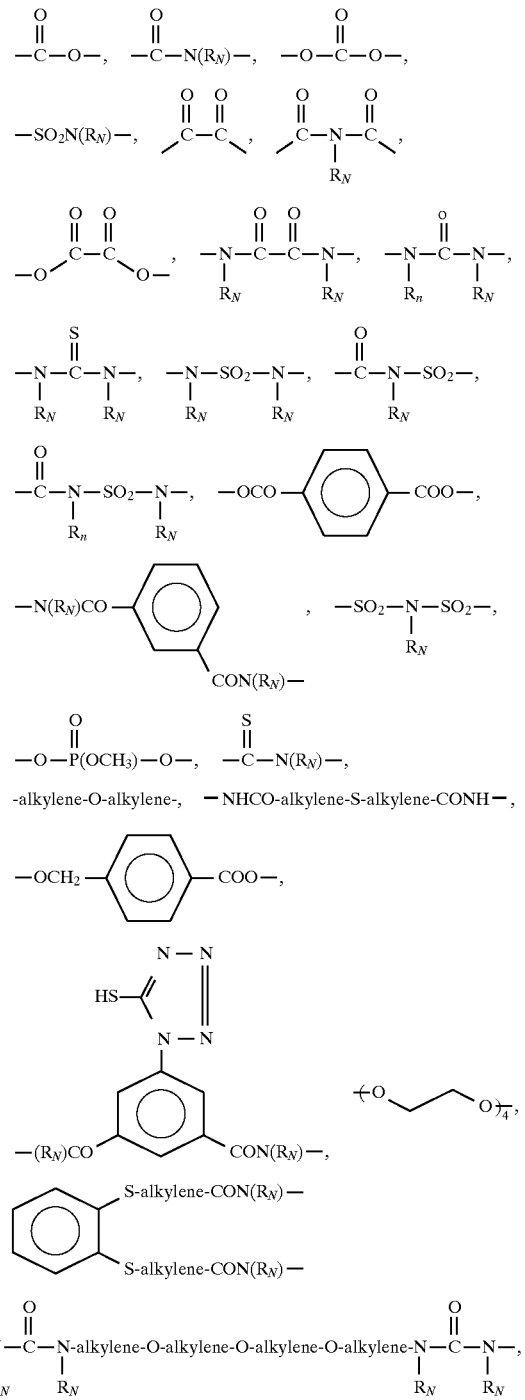

-continued
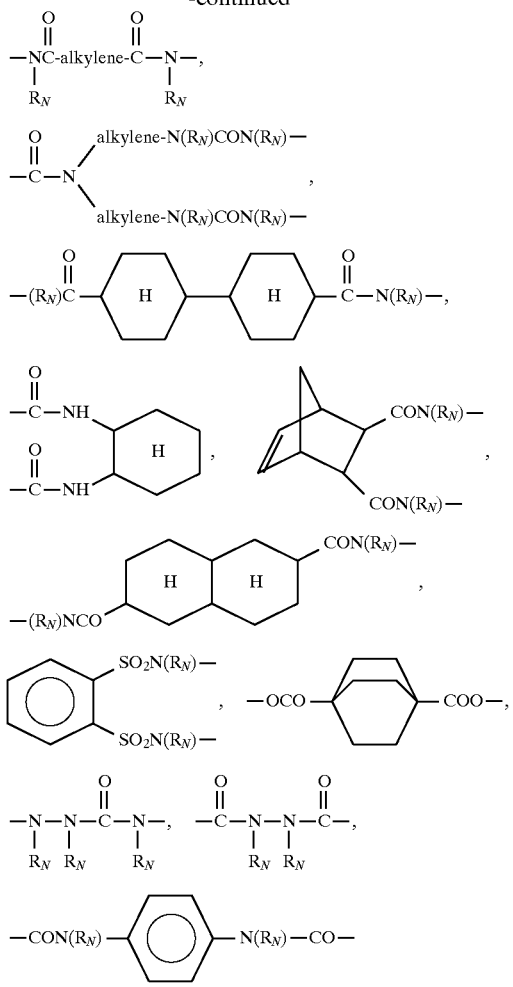
Examples of the trivalent linking group:
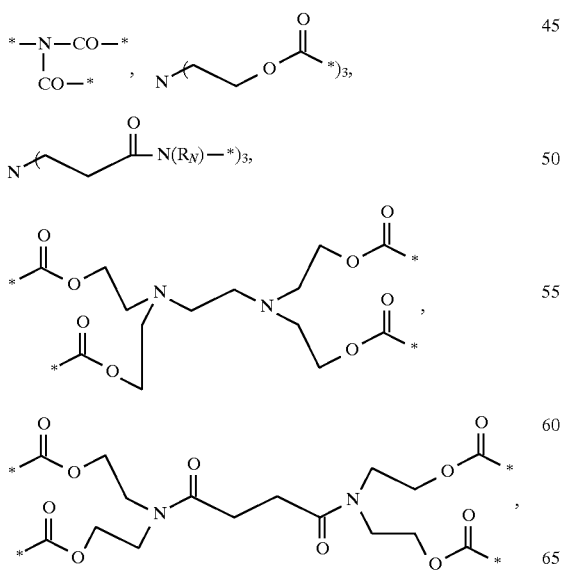
-continued
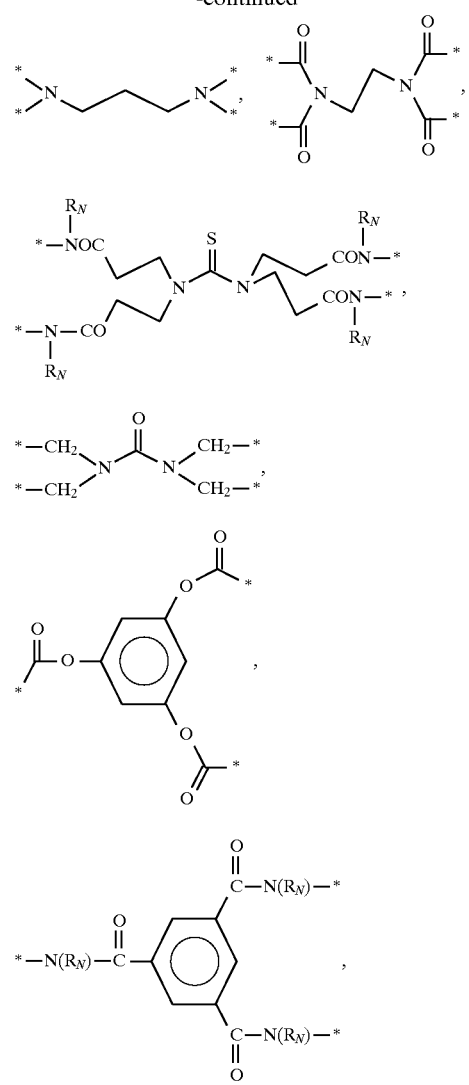

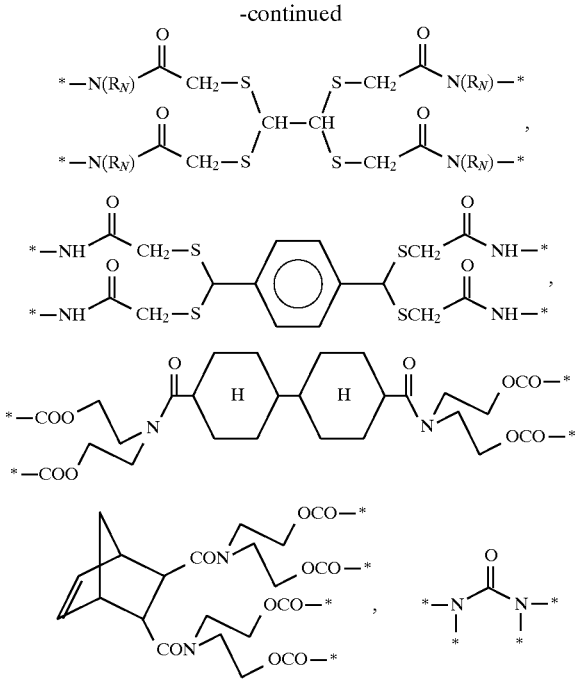

In formula (III), the linking group represented by $L_1$ is a group consisting of a combination of groups selected from —O—, —S—, —N($R_N$)— (wherein $R_N$ represents a hydrogen atom, an alkyl group or an aryl group), —CO—, —C(=S)—, —SO$_2$—, —SO— and —P(=O)—.

Specific examples of the group consisting of the combination include —CON($R_N$)—, —SO$_2$N($R_N$)—, —COO—, —N($R_N$)CON($R_N$)—, —N($R_N$)CSN($R_N$)—, —N($R_N$)SO$_2$N($R_N$)—, —SO$_2$N($R_N$)CO—, —SO$_2$N($R_N$)CON($R_N$)—, —N($R_N$)COCON($R_N$)— and —CON($R_N$)CO—.

These groups each may be bonded from either the left site or the right site thereof.

In formula (III), when the linking group represented by $L_1$ contains a tri- or more valent group, $L_1$ may link two or more groups represented by —Ar$_1$—NHNH—G$_1$—R$_1$ in formula (III). In this case, the tri- or more valent linking group contained in $L_1$ specifically includes an amino group.

In formula (III), $L_1$ is preferably —SO$_2$NH—, —NHCONH—, —O—, —S— or —N($R_N$)—, more preferably —SO$_2$NH—.

In formula (III), the aromatic group represented by Ar$_1$ is a monocyclic or bicyclic arylene group and specific examples thereof include a substituted or unsubstituted phenylene and naphthylene groups.

In formula (III), Ar$_1$ is preferably a phenylene group.

The group represented by Ar$_1$ may have a substituent and the substituent includes those described as the substituent of $A_1$ in formula (I).

Preferred examples of the substituent on the group represented by Ar$_1$ include a carboxyl group, a sulfo group, an alkyl group, an amino group, an alkylamino group, a hydroxy group, an alkoxy group, a halogen atom, an acylamino group, a sulfonamido group and a ureido group, and these groups each preferably has a total carbon number of from 1 to 12, more preferably from 1 to 8.

In formula (III), Ar$_1$ is preferably an unsubstituted phenylene group.

In formula (III), G$_1$ represents a carbonyl group, an oxaryl group, a sulfonyl group or a phosphoryl group, preferably a carbonyl group or an oxaryl group, still more preferably a carbonyl group.

In formula (III), $R_1$ represents a hydrogen atom or a block group. Specific examples of the block group include an alkyl group, an aralkyl group, an alkenyl group, an alkynyl group, an aryl group, a heterocyclic group, an alkoxy group, an aryloxy group, an amino group and a hydrazino group, and these groups exclusive of the hydrogen atom each may be substituted.

Examples of the alkyl group include a methyl group, a trifluoromethyl group, a difluoromethyl group, a 2-carboxytetrafluoroethyl group, a methoxyethyl group, a phenoxymethyl group, a pyridiniomethyl group, a 3-hydroxypropyl group, a 3-methanesulfonamidopropyl group and a phenylsulfonylmethyl group. Examples of the aralkyl group include an o-hydroxybenzyl group and an o-aminobenzyl group. Examples of the alkenyl group include a vinyl group and a 2-ethoxycarbonylvinyl group. Examples of the alkynyl group include an ethynyl group and 2-methoxycarbonylethynyl group. Examples of the aryl group include a 3,5-dichlorophenyl group, a 2-hydroxymethylphenyl group, a 2-carbamoylphenyl group, a 3,5-dichloro-2-hydroxymethylphenyl group, a 2-methanesulfonamidophenyl group, a 4-cyanophenyl group and a 3,4-dinitrophenyl group. Examples of the heterocyclic group include a 4-pyridyl group, a benzotriazol-5-yl group, a 3-(2-mercaptotetrazolyl)phenyl group and an N-methyl-4-pyridinio group. Examples of the alkoxy group include a methoxy group, a propoxy group and a 2-hydroxyethoxy group. Examples of the aryloxy group include a phenoxy group and a 1-naphthyloxy group. Examples of the amino group include an amino group, a propylamino group, a dimethylamino group, a 2,2,6,6-tetramethylpiperidin-4-yl group, an anilino group, a 2-hydroxyanilino group, a 5-benzotriazolylamino group and a 1-benzyl-3-pyridinioamino group. Examples of the hydrazino group include a hydrazino group, a 2-phenylhydrazino group and a 4-benzenesulfonamidophenylhydrazino group.

When these groups each has a substituent, the substituent include those described as the substituent of $A_1$ in formula (I), however, the total number of carbon atoms of the substituents is preferably from 0 to 12, more preferably from 0 to 8.

In formula (III), when G$_1$ represents a carbonyl group, $R_1$ is preferably a hydrogen atom, an alkyl group, an alkenyl group, an alkynyl group, an aryl group or a heterocyclic group, more preferably a hydrogen atom, an alkyl group or an aryl group, most preferably an alkyl group.

In formula (III), when G$_1$ represents an oxalyl group, $R_1$ is preferably an alkoxy group, an aryloxy group or an amino group, more preferably an amino group.

Among the compounds represented by formula (III), more preferred are those represented by the following formula (IV):

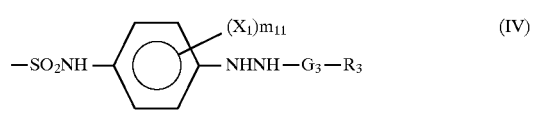

wherein G$_3$ and R$_3$ have the same meanings as G$_1$ and R$_1$ in formula (III), respectively, X$_1$ represents a substituent, and $m_{11}$ represents an integer of from 0 to 4.

In formula (IV), the substituent represented by X$_1$ is the same as the substituent on the group represented by Ar$_1$ in formula (III) and the preferred examples thereof are also the same. $m_{11}$ represents an integer of from 0 to 4, and $m_{11}$ is preferably 0 or 1, more preferably 0.

In formula (I) or (II), $b_1$ represents an integer of from 3 to 6, and $b_1$ is preferably 3 or 4, more preferably 3. In formula (II), $b_2$ represents an integer of from 1 to 5, and $b_2$ is preferably 1 or 2, more preferably 1 $m_1$ represents an integer of from 2 to 6, provided that when $b_2$ is 1, $m_1$ represents an integer of from 3 to 6, preferably 3 or 4, and when $b_2$ is 2, $m_1$ is preferably 2.

In formula (I), from three to six B groups may be the same or different. In formula (II), from two to six $\{A_2-(B)b_2\}$ groups may be the same or different and from one to five B groups may also be the same or different.

Examples of the compounds of the present invention are set forth below, however, the present invention is by no means limited thereto.

TABLE 1-1-1

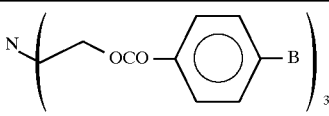

| | | R = | | |
|---|---|---|---|---|
| | −H | −CF$_3$ | −CF$_2$H | −C$_2$F$_4$COOH or (−C$_2$F$_4$−COOK) |
| 1 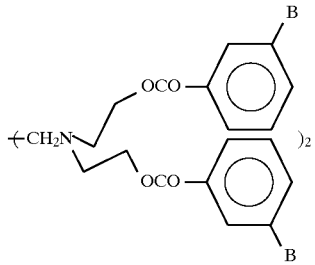 | 1a | 1b | 1c | 1d |
| 2 | 2a | 2b | 2c | 2d |
| 3 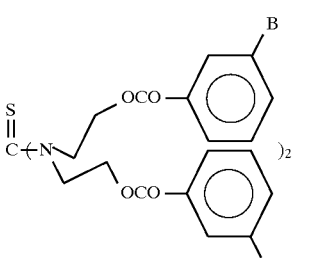 | 3a | 3b | 3c | 3d |
| 4 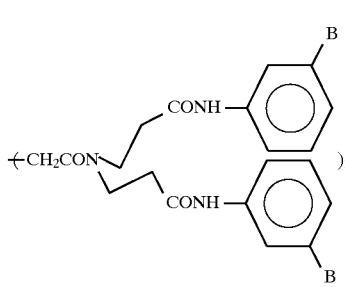 | 4a | 4b | 4c | 4d |
| 5 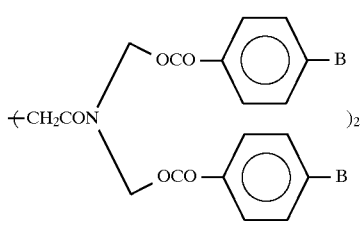 | 5a | 5b | 5c | 5d |

TABLE 1-1-1-continued

B = —SO$_2$NH—⟨phenyl⟩—NHNH—C(=O)—R

| | | | R = | |
|---|---|---|---|---|
| | —H | —CF$_3$ | —CF$_2$H | —C$_2$F$_4$COOH or (—C$_2$F$_4$—COOK) |
| 6 [structure] | 6a | 6b | 6c | 6d |
| 7 N(—CH$_2$CONH—⟨phenyl⟩—B)$_3$ | 7a | 7b | 7c | 7d |
| 8 N(—CH$_2$COO—CH$_2$CONH—⟨phenyl⟩—B)$_3$ | 8a | 8b | 8c | 8d |

TABLE 1-1-2

B = —SO$_2$NH—⟨phenyl⟩—NHNH—C(=O)—R

| | | | R = | |
|---|---|---|---|---|
| | —H | —CF$_3$ | —CF$_2$H | —C$_2$F$_4$COOH or (—C$_2$F$_4$—COONa) |
| 9 N(—CH$_2$CH$_2$CONH—⟨phenyl⟩—B)$_3$ | 9a | 9b | 9c | 9d |
| 10 [structure] | 10a | 10b | 10c | 10d |
| 11 [structure] | 11a | 11b | 11c | 11d |

TABLE 1-1-2-continued $$B = -SO_2NH-\underset{}{\underset{}{\bigcirc}}-NHNH-\underset{\parallel}{\overset{O}{C}}-R$$

| | | R = | | |
|---|---|---|---|---|
| | −H | −CF$_3$ | −CF$_2$H | −C$_2$F$_4$COOH or (−C$_2$F$_4$−COONa) |
| 12 | 12a | 12b | 12c | 12d |
| 13 | 13a | 13b | 13c | 13d |
| 14 | 14a | 14b | 14c | 14d |
| 15 | 15a | 15b | 15c | 15d |
| 16 | 16a | 16b | 16c | 16d |

TABLE 1-1-3

B = —SO₂NH—⟨phenyl⟩—NHNH—C(=O)—R

| | R = —H | —CF₃ | —CF₂H | —C₂F₄COOH or (—C₂F₄—COOK) |
|---|---|---|---|---|
| 17 | 17a | 17b | 17c | 17d |
| 18 | 18a | 18b | 18c | 18d |
| 19 | 19a | 19b | 19c | 19d |
| 20 | 20a | 20b | 20c | 20d |
| 21 | 21a | 21b | 21c | 21d |
| 22 | 22a | 22b | 22c | 22d |

TABLE 1-1-3-continued $$B = -SO_2NH-\underset{}{\underset{}{\bigcirc}}-NHNH-\overset{O}{\underset{\|}{C}}-R$$

| | R = | | | |
|---|---|---|---|---|
| | −H | −CF$_3$ | −CF$_2$H | −C$_2$F$_4$COOH or (−C$_2$F$_4$−COOK) |
| 23 [B-C$_6$H$_4$-NHCOCH$_2$S / (CH(CH$_3$)$_2$)$_2$C$_6$H$_4$ / SCH$_2$CONH-C$_6$H$_4$-B]$_2$ | 23a | 23b | 23c | 23d |
| 24 [B-C$_6$H$_4$-NHCO / norbornene / CONH-C$_6$H$_4$-B]$_2$ | 24a | 24b | 24c | 24d |

TABLE 1-1-4

$$B = -SO_2NH-\underset{}{\underset{}{\bigcirc}}-NHNH-\overset{O}{\underset{\|}{C}}-R$$

| | R = | | |
|---|---|---|---|
| | 4-CN-C$_6$H$_4$- | 3-HO-C$_6$H$_4$- | −CH$_2$−N$^+$C$_5$H$_5$ Cl$^\ominus$ |
| 25 (−CH(SCH$_2$CONH-C$_6$H$_4$-B)−)$_2$ | 25e | 25f | 25g |
| 26 (S=C(N(CH$_2$CH$_2$CONH-C$_6$H$_4$-B))−)$_2$ | 26e | 26f | 26g |

TABLE 1-1-4-continued

B = —SO₂NH—⟨C₆H₄⟩—NHNH—C(=O)—R

| | | 27e | 27f | 27g |
|---|---|---|---|---|
| 27 | *—⟨C₆H₄⟩—*  *—CONH—NHCONH—⟨C₆H₄⟩—B | | | |

R =

(27g: acetamido-substituted piperidine-type group)

| | | | | 25h |
|---|---|---|---|---|
| 25 | (CH—SCH₂CONH—⟨C₆H₄⟩—B)₂ | | | |

| | | | | 26h |
|---|---|---|---|---|
| 26 | S=C—N(CH₂CH₂CONH—⟨C₆H₄⟩—B)₂ | | | |

| | | | | 27h |
|---|---|---|---|---|
| 27 | *—⟨C₆H₄⟩—*  *—CONH—NHCONH—⟨C₆H₄⟩—B | | | |

TABLE 1-1-5

B = —SO₂NH—⟨C₆H₄⟩—NHNH—C(=O)—R

R =

(28i: 2-hydroxyphenyl acetamido group; 28j: benzotriazol-5-yl acetamido group)

| | | 28i | 28j |
|---|---|---|---|
| 28 | N(—CH₂CH₂OCO—⟨C₆H₄⟩—B)₃ | | |

TABLE 1-1-5-continued
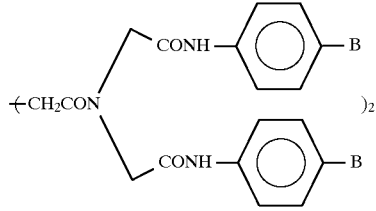

TABLE 1-1-5-continued

B = —SO₂NH—⟨phenyl⟩—NHNH—C(=O)—R

| 30 | 30k | 30l |

Structure 30: Glyceryl tris(4-B-benzoate) — CH(CH₂OCO-C₆H₄-B)₃

| 31 | 31k | 31l |

Structure 31: 1,4-phenylenebis(NHCON(CH₂CH₂NHCO-C₆H₄-B)₂)

TABLE 1-1-6

32

CF₂H—C(=O)—NHNH—⟨C₆H₄⟩—NHCONH—⟨C₆H₃⟩(NHCONH—⟨C₆H₄⟩—NHNH—C(=O)—CF₂H)(SO₂NH—⟨C₆H₄⟩—NHNH—C(=O)—CF₂CF₂—COO⁻K⁺)

33

H—C(=O)—NHNH—⟨C₆H₄⟩—NHC(=O)—⟨C₆H₃⟩(SO₂NH—⟨C₆H₄⟩—NHNH—C(=O)—CF₃)(SO₂NH—⟨C₆H₄⟩—NHNH—C(=O)—CF₃)

34

CF₂H—C(=O)—NHNH—⟨C₆H₄⟩—NHSO₂—⟨C₆H₃⟩(COOH)(CONH—⟨C₆H₄⟩—NHNH—C(=O)—C₂F₄—COOH)(CONH—⟨C₆H₄⟩—NHNH—C(=O)—C₂F₄—COOH)

TABLE 1-1-6-continued

35
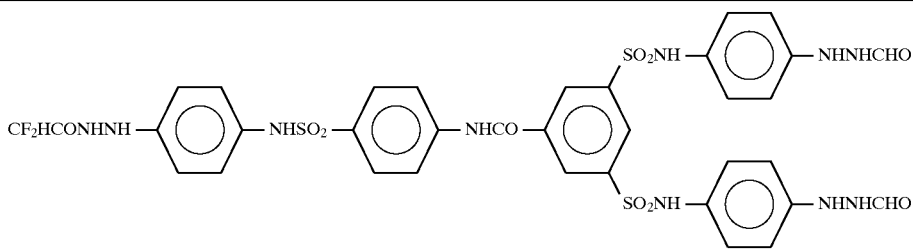

36
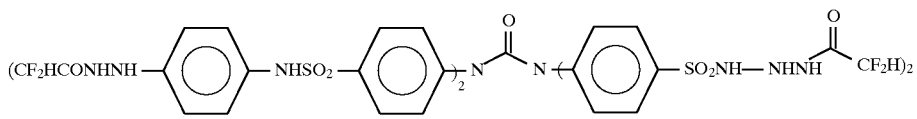

Synthesis Example 1-1
(Synthesis Compound 19c)

Compound 19c was synthesized according to Scheme 1.

Scheme 1:

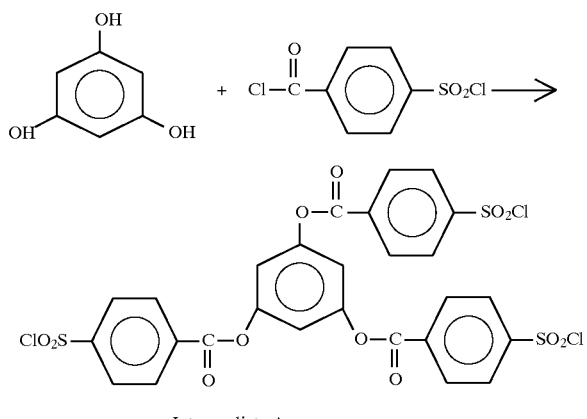

Intermediate A

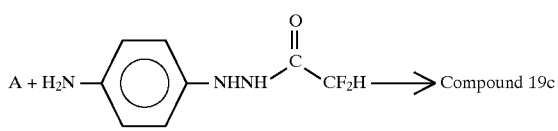 Compound 19c (Synthesis of Intermediate A)

To 100 ml of an acetonitrile solution containing 1.4 g of phloroglucinol, 9.3 ml of triethylamine was added and ice cooled, and thereto 80 ml of an acetonitrile solution containing 16.1 g of p-chlorosulfonylbenzoyl chloride was added dropwise. After stirring the mixture at room temperature for one hour, ethyl acetate and diluted hydrochloric acid were added and the product was extracted, dried and concentrated to obtain 12.6 g of Intermediate A.

(Synthesis of Compound 19c)

To 80 ml of an isopropyl alcohol solution containing 10.3 g of N-p-aminophenyl-N'-difluoroacetylhydrazine obtained by iron reducing N-p-nitrophenyl-N'-difluoroacetylhydrazine, 4.1 ml of pyridine was added, and 50 ml of an acetonitrile/dimethylacetamide mixed solution containing 12.6 g of Intermediate A was added and stirred for one hour. Ethyl acetate and diluted hydrochloric acid were added and the product was extracted, dried, concentrated and subjected to silica gel column chromatography to obtain 15.5 g of Compound 19c.

Synthesis Example 1-2
(Synthesis of Compounds 19a and 19d)

Compounds 19a and 19d were synthesized according to Scheme 2.

Scheme 2:

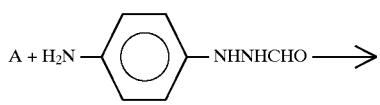

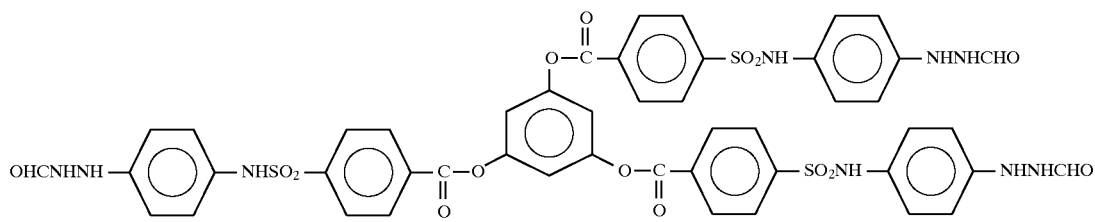

Compound 19a

-continued
Scheme 2:

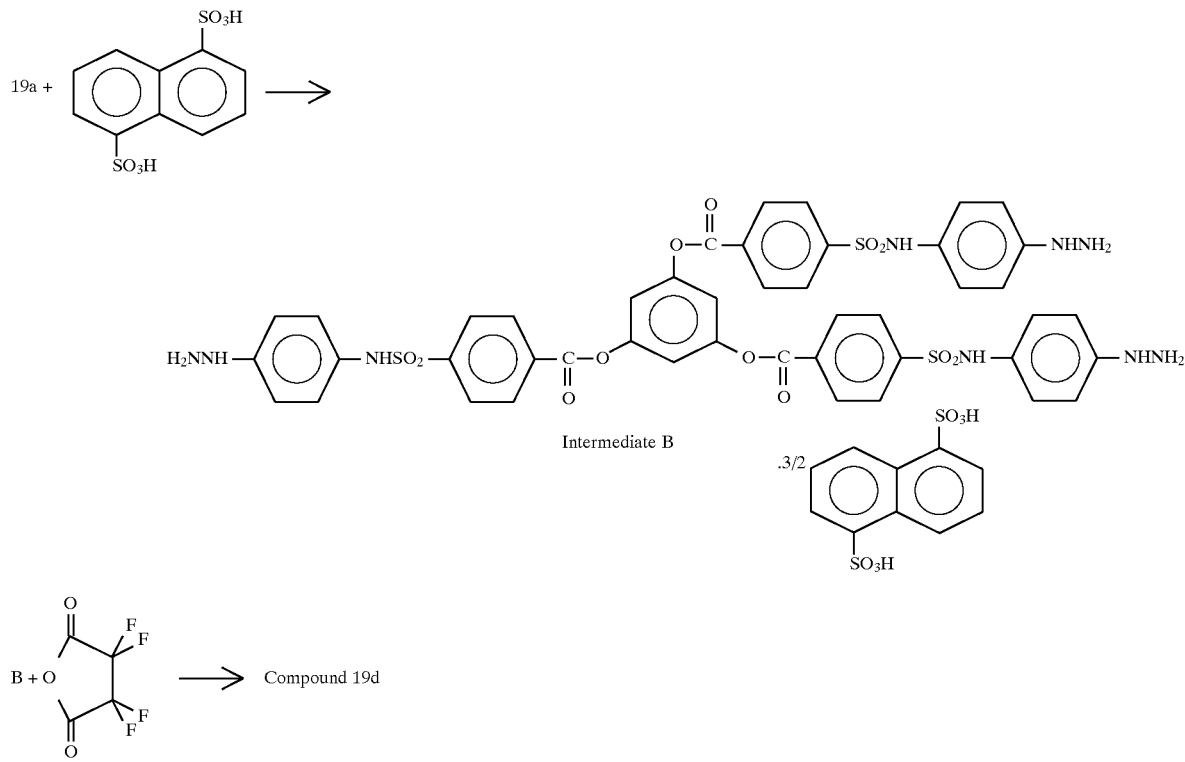

Intermediate B (Synthesis of Compound 19a)

To 40 ml of a dimethylacetamide solution containing 4.5 g of N-p-aminophenyl-N'-formylhydrazine, 2.4 ml of pyridine and 7.31 g of Intermediate A were gradually added in a nitrogen atmosphere under ice cooling. After stirring for 2 hours, ethyl acetate and diluted hydrochloric acid were added and the product was extracted, dried and concentrated. Dimethylacetamide was added thereto and dissolved, diluted hydrochloric acid was added, and the product was crystallized to obtain 7.71 g of Compound 19a.

(Synthesis of Intermediate B)

A methanol and acetonitrile mixed suspension (100 ml) containing 7.71 g of Compound 19a and 3.8 g of 1,5-naphthalenedisulfonic acid was stirred at 50° C. for 2 hours. Insoluble matters were recovered by filtration to obtain 9.37 g of Intermediate B.

(Synthesis of Compound 19d)

An acetonitrile/dimethylacetamide mixed solution (100 ml) containing 9.37 g of Intermediate B was ice cooled in a nitrogen atmosphere, and thereto 2.7 ml of triethylamine and 3.4 g of tetrafluorosuccinic acid anhydride were added. After stirring the mixture at room temperature for one hour, ethyl acetate and diluted hydrochloric acid were added and the product was extracted, dried, concentrated and subjected to silica gel column chromatography to obtain 4.32 g of Compound 19d.

Synthesis Example 1-3

(Synthesis of Compound 20c)

Compound 20c was synthesized according to Scheme 3.

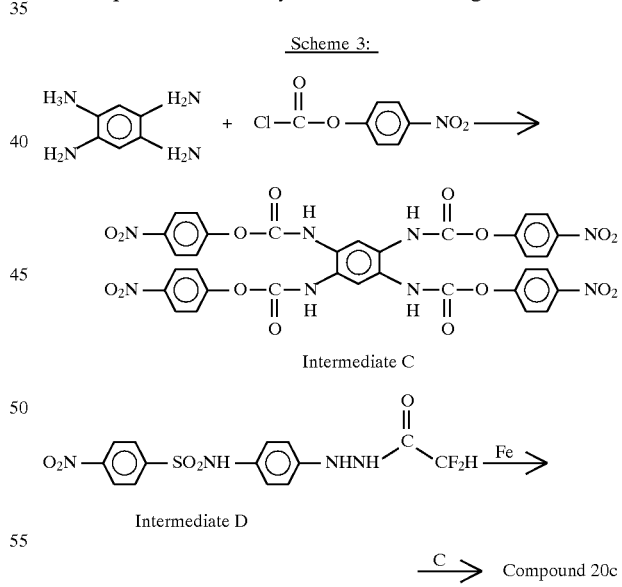

(Synthesis of Intermediate C)

To 50 ml of an acetonitrile solution containing 3.5 g of 1,2,4,5-benzenetetramine, 14 ml of triethylamine was added and ice cooled, and then 80 ml of an acetonitrile solution containing 24 g of phenyl p-nitrochlorofumarate was added to act thereon. The mixture was stirred at room temperature for one hour, insoluble matters were separated by filtration, ethyl acetate and diluted hydrochloric acid were added and the product was extracted, dried and concentrated to obtain 21.6 g of Intermediate C.

(Synthesis of Compound 20c)

To 100 ml of an isopropyl alcohol solution containing 20 g of Intermediate D prepared from p-nitrobenzenesulfonylchloride and N-p-aminophenyl-N'-difluoroacetylhydrazine, 1 g of ammonium chloride and 10 ml of water were added and heated under reflux, then thereto iron powder was added and the mixture was stirred for one hour. Insoluble matters were removed by Celite filtration, 4.0 ml of pyridine was added to the resulting filtrate, 30 ml of an acetonitrile/dimethylacetamide mixed solution containing 12 g of Intermediate C was added, and the mixture was stirred for one hour. Then, thereto ethyl acetate and diluted hydrochloric acid were added and the product was extracted, dried, concentrated and subjected to silica gel column chromatography to obtain 11.3 g of Compound 20c.

Synthesis Example 1-4

Compound 12a was synthesized according to Scheme 4.

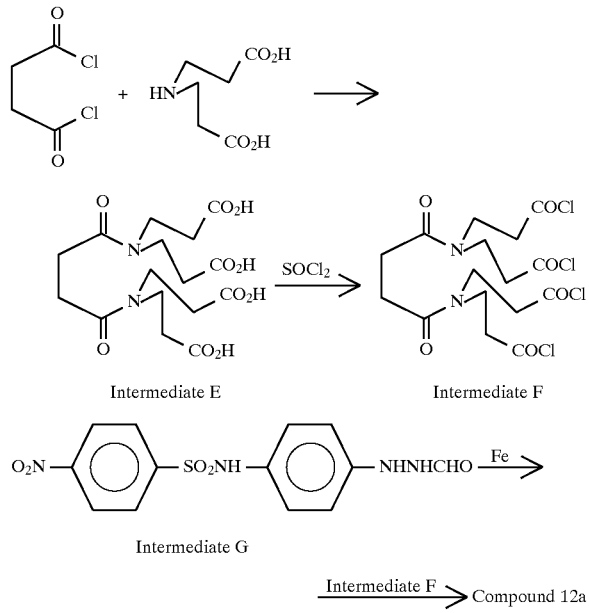

(Synthesis of Intermediate F)

To 70 ml of an acetonitrile solution containing 6.22 g of succinic acid dichloride, 50 ml of an acetonitrile solution containing 11 ml of triethylamine and 8.4 g of iminodipropionic acid was added dropwise under ice cooling. After stirring the mixture at room temperature for one hour, ethyl acetate and diluted hydrochloric acid were added, and the product was extracted, dried and concentrated to obtain 12.4 g of Intermediate E.

(Synthesis of Intermediate F)

To 50 ml of a methylene chloride solution containing 12.4 g of Intermediate E, 1 ml of dimethylformamide was added, and then thereto 30 ml of thionyl chloride was added dropwise at room temperature. The reaction solution was heated under reflux for 2 hours and excessive thionyl chloride was distilled off under reduced pressure to obtain 4.1 g of Intermediate F.

(Synthesis of Compound 12a)

To 100 ml of an isopropyl alcohol solution containing 16.7 g of Intermediate G prepared from p-nitrobenzenesulfonyl chloride and N-p-aminophenyl-N'-formylhydrazine, 1 g of ammonium chloride and 10 ml of water were added and heated under reflux, then thereto iron powder was added, and the mixture was stirred for one hour. Insoluble matters were removed by Celite filtration, 4 ml of pyridine was added to the resulting filtrate, 30 ml of an acetonitrile/dimethylacetamide mixed solution containing 4.1 g of Intermediate F was added, and the mixture was stirred for one hour. Thereto, ethyl acetate and diluted hydrochloric acid were added and the product was extracted, dried, concentrated and subjected to silica gel column chromatography to obtain 8.6 g of Compound 12a.

Synthesis Example 1-5

Compound 12b was synthesized according to Scheme 5.

Scheme 5:

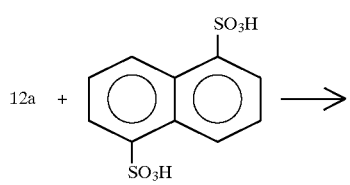

-continued
Scheme 5:

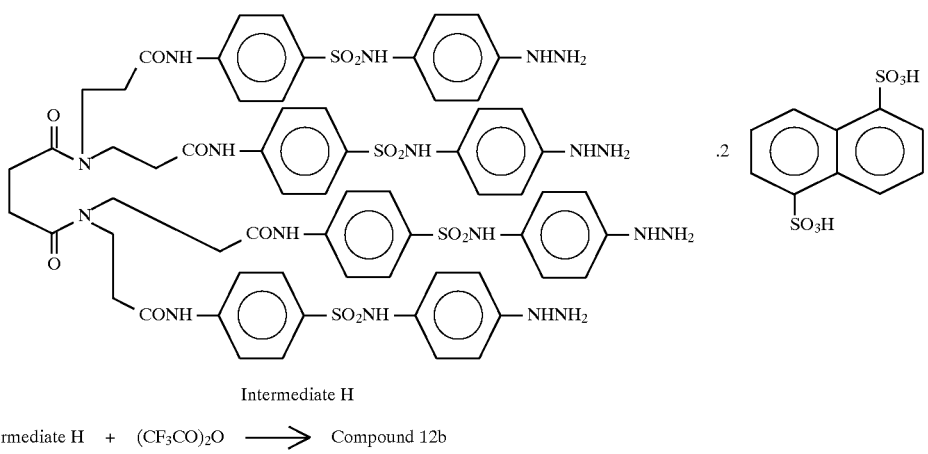

Intermediate H

Intermediate H + (CF₃CO)₂O ⟶ Compound 12b (Synthesis of Intermediate H)

A methanol and acetonitrile mixed suspension (100 ml) containing 5.84 g of Compound 12a and 6.0 g of 1,5-naphthalenedisulfonic acid was stirred at 50° C. for 2 hours. Insoluble matters were recovered by filtration to obtain 11.66 g of Intermediate H.

(Synthesis of Compound 12b)

An acetonitrile/dimethylacetamide mixed solution (100 ml) containing 4.74 g of Intermediate H was ice cooled in a nitrogen atmosphere, and thereto 3 ml of triethylamine and 3.3 g of trifluoroacetic anhydride were added. The mixture was stirred at room temperature for one hour, then thereto ethyl acetate and diluted hydrochloric acid were added, and the product was extracted, dried, concentrated and subjected to silica gel column chromatography to obtain 5.68 g of Compound 12b.

Synthesis Example 1-6

Compound 12b was synthesized according to Scheme 6.

Scheme 6:

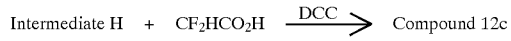

Intermediate H + CF₂HCO₂H —DCC→ Compound 12c

To 60 ml of an acetonitrile solution containing 7.44 g of Intermediate H and 3 g of difluoroacetic acid, 4.6 ml of triethylamine was added, and thereto 20 ml of an acetonitrile solution containing 6.2 g of dicyclohexylcarbodiimide was added dropwise under ice cooling. The mixture was stirred at room temperature for 2 hours, insoluble matters were separated by filtration, ethyl acetate and diluted hydrochloric acid were added, and the product was extracted, dried, concentrated and subjected to silica gel column chromatography to obtain 6.3 g of Compound 12c.

Synthesis Example 1-7

Compound 4a was synthesized according to Scheme 7.

Scheme 7:

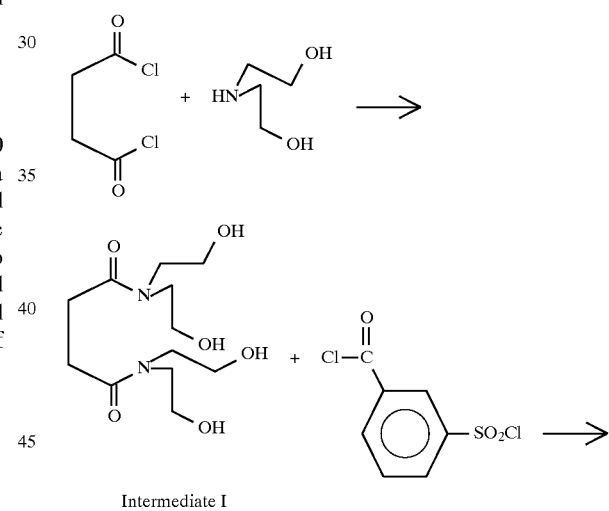

Intermediate I

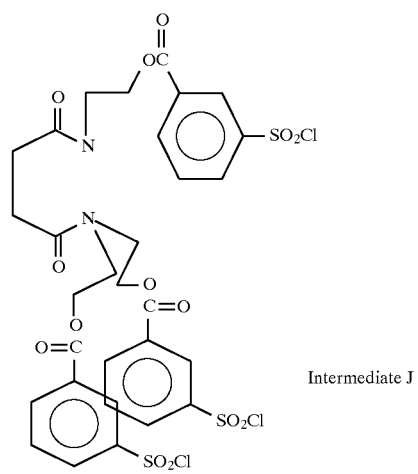

Intermediate J

-continued
Scheme 7:

Intermediate J + 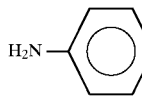 ⟶ Compound 4a (Synthesis of Intermediate J)

To 80 ml of an acetonitrile solution containing 6.22 g of succinic acid chloride, 60 ml of an acetonitrile solution containing 15 ml of triethylamine and 8.4 g of diethanolamine was added dropwise under ice cooling. The mixture was stirred at room temperature for one hour, then thereto ethyl acetate and diluted hydrochloric acid were added, and the product was extracted, dried and concentrated to obtain 13.7 g of Intermediate I.

(Synthesis of Intermediate J)

To 100 ml of an acetonitrile solution containing 3.4 g of Intermediate I, 7 ml of triethylamine was added and ice cooled, and thereto 40 ml of an acetonitrile solution containing 11 g of m-chlorosulfonylbenzoyl chloride was added to act thereon. The mixture was stirred at room temperature for one hour, then thereto ethyl acetate and diluted hydrochloric acid were added, and the product was extracted, dried and concentrated to obtain 10.6 g of Intermediate J.

(Synthesis of Compound 4a)

To 40 ml of a dimethylacetamide solution containing 6 g of N-p-aminophenyl-N'-formylhydrazine, 10.6 g of Intermediate J was gradually added in a nitrogen atmosphere under ice cooling. The mixture was stirred for 2 hours, then thereto ethyl acetate and diluted hydrochloric acid were added, and the product was extracted, dried and concentrated. Thereto, dimethylacetamide was added and dissolved, then diluted hydrochloric acid was added, and the product was crystallized to obtain 12.1 g of Compound 4a.

Synthesis Example 1-8

Compound 4c was synthesized thoroughly in the same manner as Compound 4a except for using N-p-aminophenyl-N'-difluoroacetylhydrazine in place of N-p-aminophenyl-N'-formylhydrazine in the synthesis of Compound 4a.

Synthesis Example 1-9

Compound 4d was synthesized according to Scheme 8.

Scheme 8:

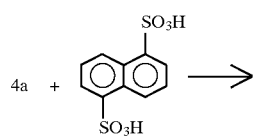 ⟶

-continued
Scheme 8:

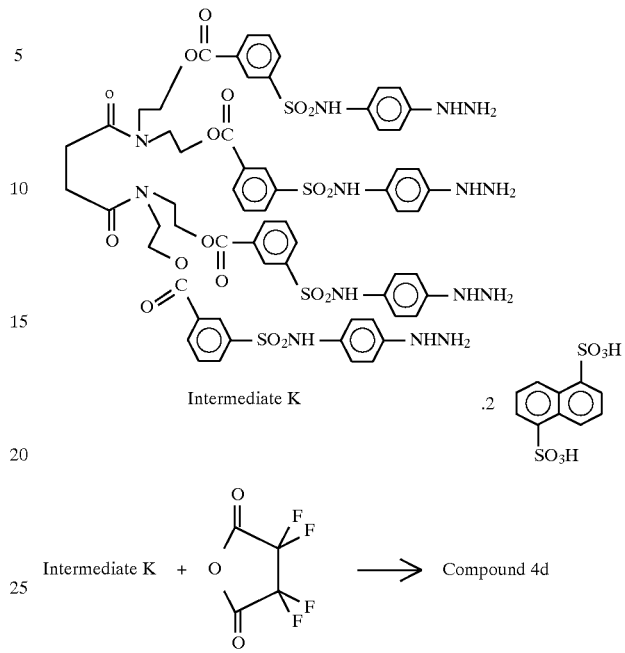

(Synthesis of Intermediate K)

A methanol and acetonitrile mixed suspension (100 ml) containing 12.7 g of Compound 4a and 6 g of 1,5-naphthalene-disulfonic acid was stirred at 50° C. for 2 hours. Insoluble matters were recovered by filtration to obtain 15.1 g of Intermediate K.

(Synthesis of Compound 4d)

An acetonitrile/dimethylacetamide mixed solution (100 ml) containing 5.44 g of Intermediate K was ice cooled in a nitrogen atmosphere, and thereto 1.5 ml of triethylamine and then 1.8 g of tetrafluorosuccinic anhydride were added. The mixture was stirred at room temperature for one hour, then thereto ethyl acetate and diluted hydrochloric acid were added, and the product was extracted, dried, concentrated and subjected to silica gel chromatography to obtain 6.23 g of Compound 4d.

Next, the hydrazide compound for use in the silver halide photographic light-sensitive material according to the second embodiment of the present invention are described in detail below.

In formulae (I') and (II'), $X_1'$, $X_2'$ and $Y_2'$ each represents a substituent capable of substitution on the benzene ring. Preferred examples of the substituent represented by $X_1'$, $X_2'$ or $Y_2'$ include a carboxyl group, a sulfo group, an alkyl group, an amino group, an alkylamino group, a hydroxy group, an alkoxy group, a halogen atom, an acylamino group, a sulfonamido group and a ureido group, and these groups each preferably has a total carbon number of from 1 to 12, more preferably from 1 to 8.

In formula (I') or (II'), $m_1'$, $m_2'$ and $m_3'$ each represents an integer of from 0 to 4. $m_1'$, $m_2'$ and $m_3'$ each is preferably 0 or 1, more preferably 0.

In formula (I') or (II'), $R_1'$ and $R_2'$ each represents a hydrogen atom or a block group.

Specific examples of the block group include an alkyl group, an aralkyl group, an alkenyl group, an alkynyl group, an aryl group, a heterocyclic group, an alkoxy group, an aryloxy group, an amino group and a hydrazino group, and these groups exclusive of the hydrogen atom each may be substituted.

Examples of the alkyl group include a methyl group, a trifluoromethyl group, a difluoromethyl group, a 2-carboxytetrafluoroethyl group, a methoxyethyl group, a phenoxymethyl group, a pyridiniomethyl group, a 3-hydroxypropyl group, a 3-methanesulfonamidopropyl group and a phenylsulfonylmethyl group. Examples of the aralkyl group include an o-hydroxy-benzyl group and an o-aminobenzyl group. Examples of the alkenyl group include a vinyl group and a 2-ethoxycarbonyl-vinyl group. Examples of the alkynyl group include an ethynyl group and 2-methoxycarbonylethynyl group. Examples of the aryl group include a 3,5-dichlorophenyl group, a 2-hydroxymethylphenyl group, a 2-carbamoylphenyl group, a 3,5-dichloro-2-hydroxymethylphenyl group, a 2-methanesulfonamidophenyl group, a 4-cyanophenyl group and a 3,4-dinitrophenyl group. Examples of the heterocyclic group include a 4-pyridyl group, a benzotriazol-5-yl group, a 3-(2-mercaptotetrazolyl)phenyl group and an N-methyl-4-pyridinio group. Examples of the alkoxy group include a methoxy group, a propoxy group and a 2-hydroxyethoxy group. Examples of the aryloxy group include a phenoxy group and a 1-naphthyloxy group. Examples of the amino group include an amino group, a propylamino group, a dimethylamino group, a 2,2,6,6-tetramethylpiperidin-4-yl group, an anilino group, a 2-hydroxyanilino group, a 5-benzotriazolylamino group and a 1-benzyl-3-pyridinioamino group. Examples of the hydrazino group include a hydrazino group, a 2-phenylhydrazino group and a 4-benzenesulfonamidophenylhydrazino group.

When these groups each has a substituent, the substituent include those described as the substituent of $A_1'$ in formula (I'), however, the total carbon atom number of the substituent is preferably from 0 to 12, more preferably from 0 to 8.

At least one of two $R_1'$ groups in formula (I') and at least one of two $R_2'$ groups in formula (II') each represents a fluorine-substituted alkyl group substituted by one or more fluorine atoms.

The fluorine-substituted alkyl group is a branched or linear substituted alkyl group having from 1 to 18 carbon atoms, substituted only by a fluorine atom or by a fluorine atom and a substituent other than fluorine atom. Specific examples thereof include a trifluoromethyl group, a difluoromethyl group, a monofluoromethyl group, a 2-carboxytetrafluoroethyl group, a chlorodifluoromethyl group, a methoxydifluoromethyl group, a methylthiodifluoromethyl group, a phenylthiodifluoromethyl group, a pentafluoroethyl group, a heptafluoropropyl group, a 4-carboxyhexafluoropropyl group and a 2-methoxycarbonyl-1,1-difluoroethyl group.

In formula (I') or (II'), the group represented by $R_1'$ or $R_2'$ is preferably a fluorine-substituted alkyl group having a total number of carbon atoms of from 1 to 8, more preferably a trifluoromethyl group, a difluoromethyl group or a 2-carboxytetrafluoroethyl group, and most preferably a trifluoromethyl group or a difluoromethyl group.

In formula (I') or (II'), two units of the group which is represented by one of the following formulae and is linked to $A_1'$ or $L_3'$ may be the same or different, more specifically two $R_1'$ groups, two $R_2'$ groups, two or more $X_1'$ groups, two or more $X_2'$ groups, two or more $Y_2'$ groups, two $L_1'$ groups, and two $L_2'$ groups may be the same or different, respectively.

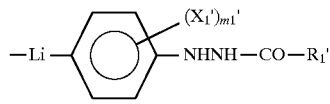

or

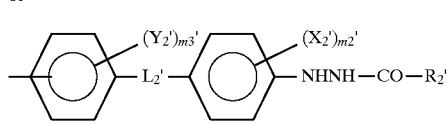

In formula (I'), $A_1'$ represents a substituted or unsubstituted benzene ring. When the ring has a substituent, the substituent includes those described as the substituent on the substituent represented by $X_1'$, $X_2'$ or $Y_2'$ in formula (I') or (II').

The substituent of $A_1'$ is preferably a halogen atom, an alkyl group, an aryl group, a carbamoyl group, an alkoxycarbonyl group, an aryloxycarbonyl group, an acyl group, a cyano group, an alkoxy group, an aryloxy group, a carbamoyloxy group, an acylamino group, a ureido group, a sulfamoylamino group, an alkoxycarbonylamino group, a sulfonamido group, a sulfamoyl group or a sulfonyl group, more preferably a halogen atom, an alkyl group, an aryl group, a carbamoyl group, an alkoxy group, an aryloxy group, an acylamino group, a ureido group, a sulfonamido group or a sulfamoyl group.

The compound represented by formula (I') may have an adsorption accelerator to silver halide as a substituent.

Examples of the adsorption accelerator to silver halide include those described in U.S. Pat. Nos. 4,385,108 and 4,459,347, JP-A-59-195233, JP-A-59-200231, JP-A-59-201045, JP-A-59-201046, JP-A-59-201047, JP-A-59-201048, J-A-59-201049, JP-A-61-170733, JP-A-61-270744, JP-A-62-948, JP-A-63-234244, JP-A-63-234245 and JP-A-63-234246, such as a thiourea group, a heterocyclic thioamide group, a mercapto heterocyclic group and a triazole group.

Specific examples of preferred adsorption accelerators to silver halide include thioureido, thioamide, thiourethane, 5-mercaptotetrazole, 3-mercapto-1,2,4-triazole, 2-mercapto-1,3,4-thiadiazole, 2-mercapto-1,3,4-oxadiazole, alkylmercapto, arylmercapto and benzotriazole.

In formula (II'), the divalent linking group represented by $L_3'$ is a group consisting of a combination of groups selected from an alkylene group, a cycloalkylene group, an alkenylene group, an alkynylene group, a phenylene group, —O—, —S—, —N($R_N$)—(wherein $R_N$ represents a single bond, a hydrogen atom, an alkyl group or an aryl group), —CO—, —C(=S)—, —C(=N—$R_N$)—, —SO$_2$—, —SO— and —P(=O)—.

The alkylene group is a linear or branched, substituted or unsubstituted alkylene group, and specific examples thereof include a methylene group, an ethylene group, a propylene group, a hexafluoropropylene group and an α-ethylmethylene group. The cycloalkylene group is a mono-, bi- or tricyclic, substituted or unsubstituted cycloalkylene group, and specific examples thereof include a cyclohexylene group, a bicyclohexylene group, an adamantylene group, a norbornylene group and a decalin-2,6-diyl group. The alkenylene group is a substituted or unsubstituted alkenylene group, and specific examples thereof include a vinylene group, a 1,3-butadien-1,4-diyl group and a tetrafluorovinylene group. The alkynylene group is a substituted or unsubstituted alkynylene group, and specific examples thereof include an ethynylene group. The phenylene group is a substituted or unsubstituted phenylene group.

The group represented by $L_3'$ in formula (II') does not contain a partial structure of biphenyl, diphenylmethane (including bisphenol), triphenylmethane, benzophenone, diphenylamine, triphenylamine, diphenylether, diphenylsulfide, diphenylsulfone, stilbene, fluorenone, anthraquinone, binaphthyl or dinaphthylether.

Further, $L_3'$ does not contain a quaternary nitrogen atom such as an ammonio group and a pyridinio group.

The group represented by $L_3'$ in formula (II') preferably does not contain a cationic group.

Specific examples of the divalent linking group represented by $L_3'$ in formula (II') are set forth below.

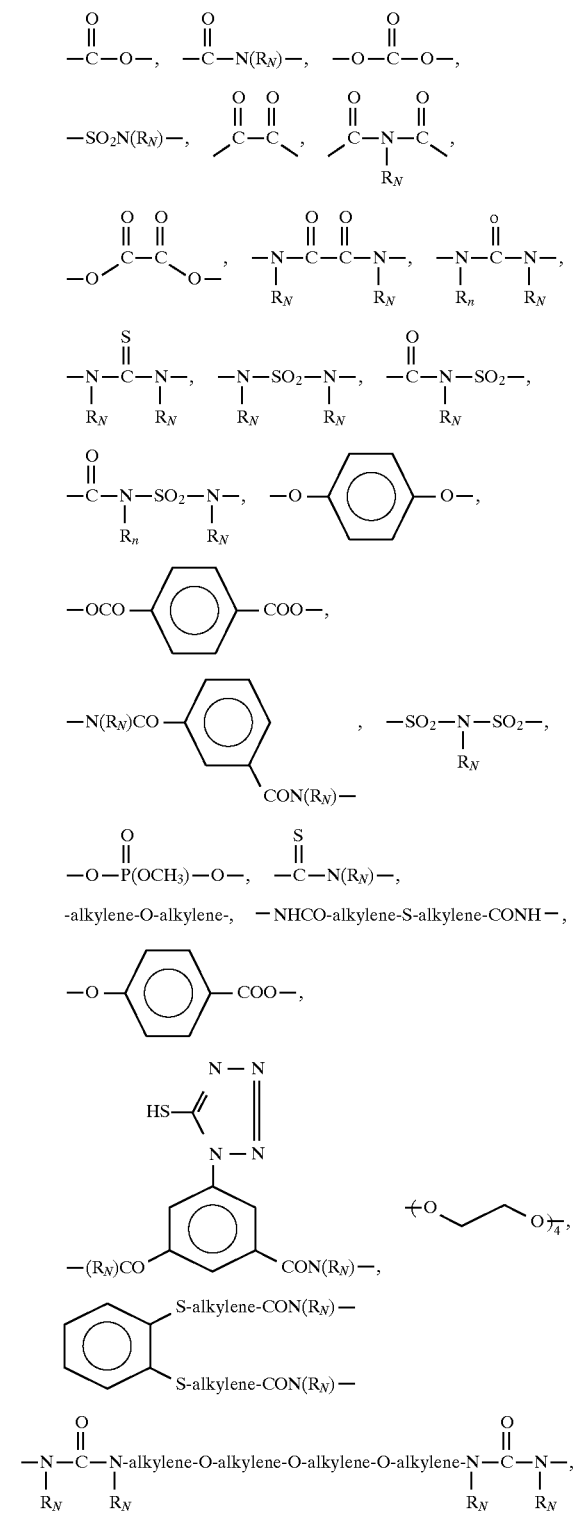

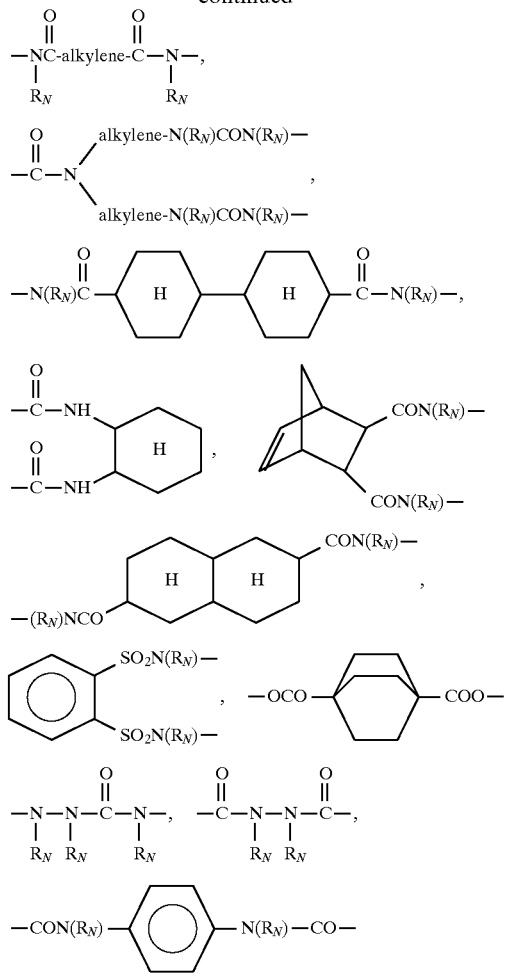

When the group represented by $L_3'$ has a substituent, the substituent includes those described as the substituent of $A_1'$ in formula (I'), and the preferred examples thereof are also the same.

In formula (I') or (II'), the divalent linking group represented by $L_1'$ or $L_2'$ is a group consisting of a combination of groups selected from —O—, —S—, —N($R_N$)— (wherein $R_N$ represents a hydrogen atom, an alkyl group or an aryl group), —CO—, —C(=S)—, —SO$_2$—, —SO— and —P(=O)—.

Specific examples of the group consisting of the combination include —CON($R_N$)—, —SO$_2$N($R_N$)—, —COO—, —N($R_N$)CON($R_N$)—, —N($R_N$)CSN($R_N$)—, —N($R_N$)SO$_2$N ($R_N$)—, —SO$_2$N($R_N$)CO—, —SO$_2$N($R_N$)CON($R_N$)—, —N($R_N$)COCON($R_N$)—, —CON($R_N$)CO— and —N($R_N$)N ($R_N$)CON($R_N$)—. These groups each may be bonded from either the left site or the right site thereof.

In formula (I') or (II'), $L_1'$ and $L_2'$ each is preferably —SO$_2$NH—, —NHCONH—, —CONH—, —O—, —S— or —N($R_N$)—, more preferably —SO$_2$NH—.

At least one of two $L_1'$ groups in formula (I') and at least one of two $L_2'$ groups in formula (II') each is more preferably an —SO$_2$NH— group.

Examples of the compounds of the present invention are set forth below, however, the present invention is by no means limited thereto.

TABLE 1-2-1
$$B = -SO_2NH-\underset{}{\underset{}{\bigcirc}}-NHNH-\overset{O}{\underset{\|}{C}}-R$$
| | | | R = | |
|---|---|---|---|---|
| | | | $-CF_2CF_2COOH$ or | |
| | $-CF_3$ | $-CF_2H$ | $(-CF_2CF_2COOK)$ | $-CF_2OCH_3$ |
| 1 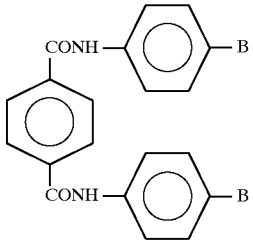 | 1a' | 1b' | 1c' | 1d' |
| 2 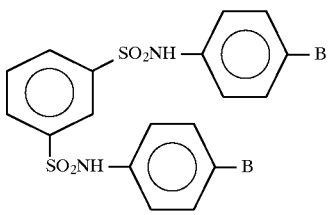 | 2a' | 2b' | 2c' | 2d' |
| 3 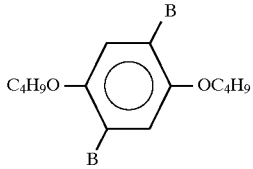 | 3a' | 3b' | 3c' | 3d' |
| 4 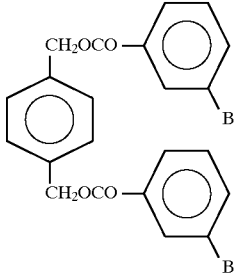 | 4a' | 4b' | 4c' | 4d' |
| 5 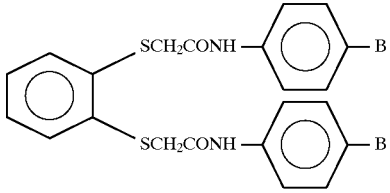 | 5a' | 5b' | 5c' | 5d' |

TABLE 1-2-1-continued

TABLE 1-2-2-continued
B = —SO$_2$NH—C$_6$H$_4$—NHNH—C(=O)—R
| | | R = | | |
|---|---|---|---|---|
| | —CF$_3$ | —CF$_2$H | —CF$_2$CF$_2$COOH or (—C$_2$F$_4$COOK) | —CF$_2$SCH$_3$ |
| 10 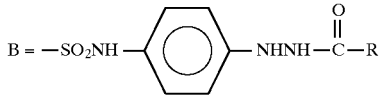 | 10a' | 10b' | 10c' | 10e' |
| 11 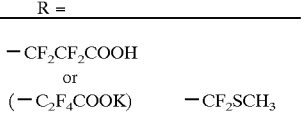 | 11a' | 11b' | 11c' | 11e' |
| 12 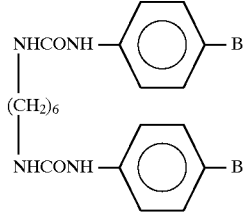 | 12a' | 12b' | 12c' | 12e' |
| 13 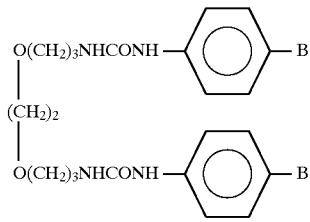 | 13a' | 13b' | 13c' | 13e' |
| 14 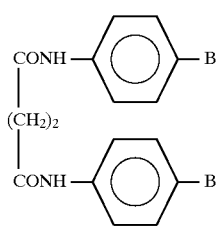 | 14a' | 14b' | 14c' | 14e' |
| 15 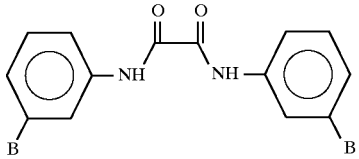 | 15a' | 15b' | 15c' | 15e' |
| 16 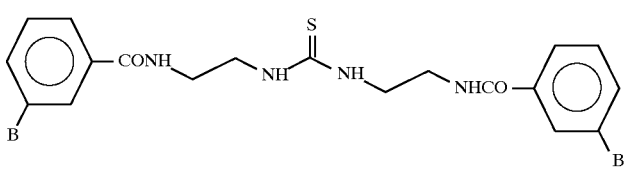 | 16a' | 16b' | 16c' | 16e' |

TABLE 1-2-3

$$B = -SO_2NH-\underset{}{\bigcirc}-NHNH-\overset{O}{\underset{\|}{C}}-R$$

| | R = | | | |
|---|---|---|---|---|
| | $-CF_3$ | $-CF_2H$ | $-CF_2CF_2COOH$ or $(-CF_2CF_2COOK)$ | $-C_3F_6-COOH$ or $(-C_3F_6COOK)$ |
| 17 B—⟨⟩—NHCO—⟨H⟩—⟨H⟩—CONH—⟨⟩—B | 17a' | 17b' | 17c' | 17f' |
| 18 (norbornene with two CONH—⟨⟩—B) | 18a' | 18b' | 18c' | 18f' |
| 19 (cyclohexane with two NHCO—⟨⟩—B) | 19a' | 19b' | 19c' | 19f' |
| 20 B—⟨⟩—NHOC...COOH / HOOC...CONH—⟨⟩—B | 20a' | 20b' | 20c' | 20f' |
| 21 (diethylene glycol diester with two ⟨⟩—B) | 21a' | 21b' | 21c' | 21f' |
| 22 (adamantane with two NHCONH—⟨⟩—B) | 22a' | 22b' | 22c' | 22f' |
| 23 (hydroquinone with two SO_2NH—⟨⟩—B) | 23a' | 23b' | 23c' | 23f' |

TABLE 1-2-3-continued $$B = -SO_2NH-\underset{}{\underset{}{\bigcirc}}-NHNH-\overset{O}{\underset{\parallel}{C}}-R$$

| | | R = | | |
|---|---|---|---|---|
| | $-CF_3$ | $-CF_2H$ | $-CF_2CF_2COOH$ or $(-CF_2CF_2COOK)$ | $-C_3F_6-COOH$ or $(-C_3F_6COOK)$ |
| 24 ![structure with C8H17, CONH, two B-substituted phenyl rings] | 24a' | 24b' | 24c' | 24f' |

TABLE 1-2-4

$$B = -SO_2NH-\underset{}{\underset{}{\bigcirc}}-NHNH-\overset{O}{\underset{\parallel}{C}}-R$$

| | | R = | | |
|---|---|---|---|---|
| | $(-CF_2COOH$ or $-CF_2COONa)$ | $-CFH_2$ | $-CF_2CF_2COOCH_3$ | $-CF_2-S-\bigcirc$ |
| 25 $(-SCH_2CONH-\bigcirc-B)_2$ | 25g' | 25h' | 25i' | 25j' |
| 26 ![structure: B-phenyl-COO-(CH2CH2O)4-OCO-phenyl-B] | 26g' | 26h' | 26i' | 26j' |
| 27 ![structure: CH3O, CH3O substituted benzene with two SO2NH-phenyl-B groups] | 27g' | 27h' | 27i' | 27j' |

TABLE 1-2-5

Synthesis Example 2-1

(Synthesis of Compound 4b')

Compound 4b' was synthesized according to Scheme 1'.

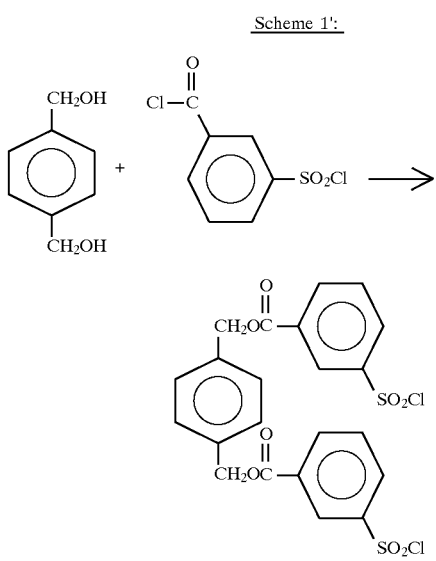

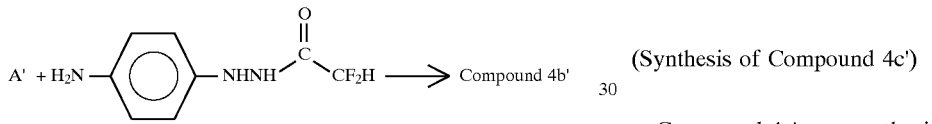

(Synthesis of Intermediate A')

To 100 ml of an acetonitrile solution containing 1.4 g of p-xylenedimethanol, 0.8 ml of triethylamine was added and ice cooled, and 40 ml of an acetonitrile solution containing 4.84 of p-chlorosulfonylbenzoyl chloride was added to act thereon. After stirring the mixture at room temperature for one hour, ethyl acetate and diluted hydrochloric acid were added and the product was extracted, dried and concentrated to obtain 5.01 g of Intermediate A'.

(Synthesis of Compound 4b')

To 60 ml of an isopropyl alcohol solution containing 3.7 g of N-p-aminophenyl-N'-difluoroacetylhydrazine obtained by iron reducing N-p-nitrophenyl-N'-difluoroacetylhydrazine, 1.5 ml of pyridine was added, and 20 ml of an acetonitrile/dimethylacetamide mixed solution containing 5.0 g of Intermediate A' was added and stirred for one hour. Ethyl acetate and diluted hydrochloric acid were added and the product was extracted, dried, concentrated and subjected to silica gel column chromatography to obtain 4.13 g of Compound 4b' (mp: 150°–153° C.).

Synthesis of Example 2-2

(Synthesis of Compound 4c')

Compound 4c' was synthesized according to Scheme 2'.

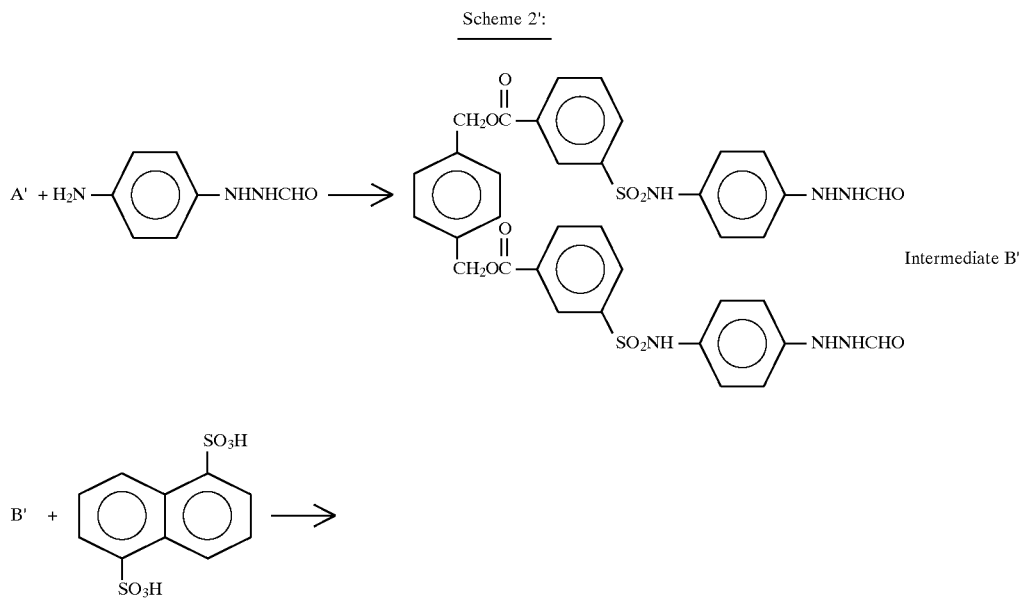

-continued
Scheme 2':

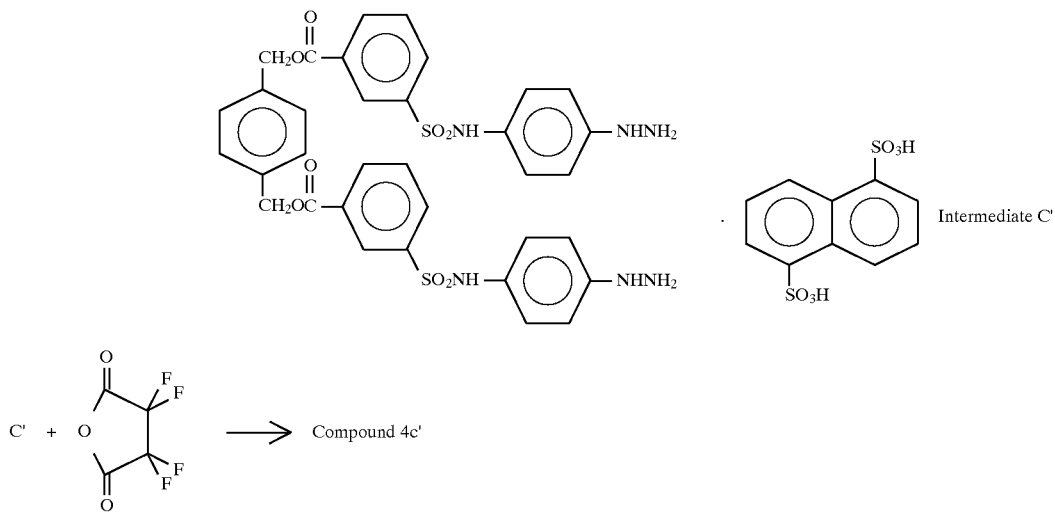

(Synthesis of Intermediate B')

To 40 ml of a dimethylacetamide solution containing 3.73 g of N-p-aminophenyl-N'-formylhydrazine, 6.70 g of Intermediate A' was gradually added in a nitrogen atmosphere under ice cooling. After stirring for 2 hours, ethyl acetate and diluted hydrochloric acid were added and the product was extracted, dried and concentrated. Dimethylacetamide was added thereto and dissolved, diluted hydrochloric acid was added, and the product was crystallized to obtain 4.86 g of Intermediate B'.

(Synthesis of Intermediate C')

A methanol/acetonitrile mixed suspension (100 ml) containing 4.86 g of Intermediate B' and 2.47 g of 1,5-naphthalenedisulfonic acid was stirred at 50° C. for 2 hours. Insoluble matters were recovered by filtration to obtain 6.11 g of Intermediate C'.

(Synthesis of Compound 4c')

An acetonitrile/dimethylacetamide mixed solution (100 ml) containing 6.11 g of Intermediate C' was ice cooled in a nitrogen atmosphere, and thereto 4.6 ml of triethylamine and 2.4 g of tetrafluorosuccinic acid anhydride were added. After stirring the mixture at room temperature for one hour, ethyl acetate and diluted hydrochloric acid were added and the product was extracted, dried, concentrated and subjected to silica gel column chromatography to obtain 6.64 g of Compound 4c' (amorphous).

Synthesis Example 2-3

(Synthesis of Compound 31b')

Compound 31b' (amorphous) was synthesized thoroughly in the same manner as in the synthesis of Compound 4b' except for using 1,4-cyclohexanedimethanol in place of p-xylenedimethanol.

Synthesis Example 2-4

(Synthesis of Compound 18c')

Compound 18c' was synthesized according to Scheme 3'.

Scheme 3':

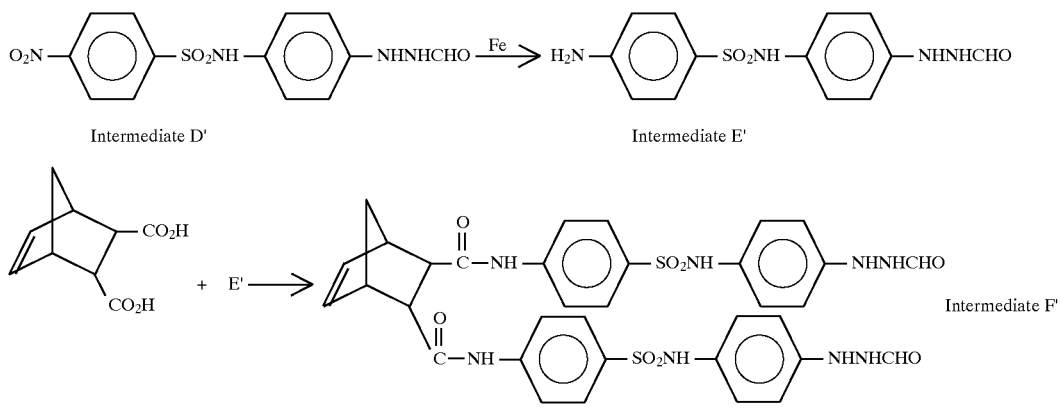

(Synthesis of Intermediate E')

To 100 ml of an isopropyl alcohol solution containing 17.3 g of Intermediate D' prepared from p-nitrobenzenesulfonylchloride and N-p-aminophenyl-N'-formylhydrazine, 1 g of ammonium chloride and 10 ml of water were added and heated under reflux, then thereto iron powder was added and the mixture was stirred for one hour. Insoluble matters were removed by Celite filtration, the solvent was distilled off and the residue was recrystallized from methylene chloride to obtain 12.6 g of Intermediate E'.
(Synthesis of Intermediate F')

To 70 ml of an acetonitrile solution containing 3.75 g of cis-5-norbornene-endo-2,3-dicarboxylic acid, 80 ml of an acetonitrile solution containing 12.6 g of Intermediate E' was added dropwise in the presence of 8.5 g of dicyclohexylcarbodiimide, and the mixture was stirred for one hour. The solid deposited was separated by filtration, ethyl acetate and diluted hydrochloric acid were added, and the product was extracted, dried, concentrated and recrystallized from an ethyl acetate/methylene chloride mixed solution to obtain 11.7 g of Intermediate F'.
(Synthesis of Compound 18c')

Compound 18c' (amorphous) was synthesized thoroughly in the same manner as in the synthesis of Compound 4c' except for using Intermediate F' in place of Intermediate B'.

Synthesis Example 5
(Synthesis of Compound 22b')

Compound 22b' was synthesized according to Scheme 4'.

The hydrazide compound for use in the present invention (hereinafter occasionally referred to as a "hydrazine-base nucleating agent") may be dissolved in an appropriate water-miscible organic solvent prior to use. Examples of the solvent include alcohols (e.g., methanol, ethanol, propanol, fluorinated alcohol), ketones (e.g., acetone, methyl ethyl ketone), dimethylformamide, dimethylsulfoxide and methyl cellosolve.

Alternatively, the hydrazide compound may be used in the form of an emulsion dispersion product obtained by dissolving the compound according to a well known emulsion dispersion method using an oil such as dibutyl phthalate, tricresyl phosphate, glyceryl triacetate or diethylphthalate, or an auxiliary solvent such as ethyl acetate or cyclohexanone, and mechanically forming it into an emulsion dispersion product. Further, powder of the hydrazine derivative may be dispersed in water according to a method known as a solid dispersion method by means of a ball mill, a colloid mill or ultrasonic waves and then used.

The hydrazine-base nucleating agent for use in the present invention is preferably used as a fine dispersion (fine crystal grain) solid dispersion. The fine (crystal) grain solid dispersion of the hydrazine-base nucleating agent can be mechani- Scheme 4':

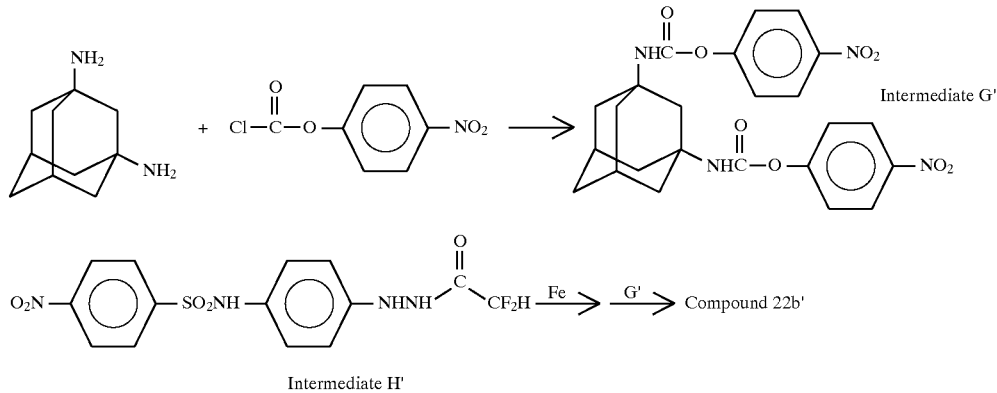

Intermediate H'

(Synthesis of Intermediate G')

To 100 ml of an acetonitrile solution containing 7.13 g of 1,3-adamantanediamine, 12 ml of triethylamine was added and ice cooled, and then 80 ml of an acetonitrile solution containing 20.5 g of phenyl p-nitrochlorofumarate was added to act thereon. After stirring the mixture at room temperature for one hour, insoluble matters were separated by filtration, ethyl acetate and diluted hydrochloric acid were added, and the product was extracted, dried and concentrated to obtain 21.6 g of Intermediate G'.
(Synthesis of Compound 22b')

To 100 ml of an isopropyl alcohol solution containing 13.5 g of Intermediate H' prepared from p-nitrobenzene-sulfonyl chloride and N-p-aminophenyl-N'-difluoroacetyl-hydrazine, 1 g of ammonium chloride and 10 ml of water were added and heated under reflux, then thereto iron powder was added, and the mixture was stirred for one hour. Insoluble matters were removed by celite filtration, 3.0 ml of pyridine was added to the resulting filtrate, 30 ml of an acetonitrile/dimethylacetamide mixed solution containing 10 g of Intermediate G' was added, and the mixture was stirred for one hour. Thereto, ethyl acetate and diluted hydrochloric acid were added and the product was extracted, dried, concentrated and subjected to silica gel column chromatography to obtain 15.2 g of Compound 22b' (amorphous).

cally prepared, if desired, using an appropriate solvent (e.g., water, alcohol) in the presence of a dispersant by a pulverization means (e.g., ball mill, vibration ball mill, planetary ball mill, sand mill, colloid mill, jet mill, roller mill). Also, the hydrazine-base nucleating agent fine (crystal) grain may be prepared using a method of dissolving a hydrazine-base nucleating agent in an appropriate solvent using a surface active agent for dispersion and then adding the solution to a bad solvent of the hydrazine-base nucleating agent to deposit fine crystal, or a method of first dissolving a hydrazine-base nucleating agent by controlling the pH and then finely crystallizing the solution by varying the pH. The thus-obtained hydrazine-base nucleating agent fine (crystal) grains are dispersed in an appropriate binder to prepare a solid dispersion of almost uniform grains, and the solid dispersion is coated on a desired support to provide a layer containing the hydrazine-base nucleating agent fine powder. Alternatively, the layer may be provided by a method of coating a hydrazine-base nucleating agent in the dissociation state as a salt form and overcoating thereon acidic gelatin to achieve dispersion fixation at the time of coating.

The above-described binder may be a polymer having an active methylene group, which is described above, or a hydrophilic colloid or synthetic polymer which can be used in a light-sensitive emulsion layer or a light-insensitive layer. The hydrophilic colloid is not particularly limited, however, gelatin is usually preferred.

The surface active agent for dispersion may be a known surface active agent and it is preferably an anionic, nonionic or amphoteric surface active agent, more preferably an anionic and/or nonionic surface active agent.

The hydrazine-base nucleating agent fine grain in the solid dispersion has an average grain size of from 0.005 to 10 µm, preferably from 0.01 to 1 µm, more preferably from 0.01 to 0.5 µm.

The hydrazine nucleating agent of the present invention may be added to any of silver halide emulsion layers and other hydrophilic colloid layers on the silver halide emulsion layer side of the support, however, it is preferably added to the silver halide emulsion layer or a hydrophilic colloid layer adjacent thereto.

The nucleating agent of the present invention is preferably added in an amount of from $1\times10^{-6}$ to $1\times10^{-2}$ mol, more preferably from $1\times10^{-5}$ to $1\times10^{-3}$ mol, most preferably from $5\times10^{-5}$ to $1\times10^{-3}$ mol, per mol of silver halide.

In the case of processing with the developer having a pH of less than 11 of the present invention, the silver halide photographic light-sensitive material particularly preferably contains a nucleation contrasting accelerator such as an amine derivative, an onium salt, a disulfide derivative or a benzyl alcohol derivative, in a silver halide emulsion layer or other hydrophilic colloid layer.

Examples of the nucleation accelerator for use in the present invention include amine derivatives, onium salts, disulfide derivatives and hydroxymethyl derivatives. Examples thereof include: compounds described in JP-A-7-77783, page 48, lines 2 to 37, specifically, Compounds A-1) to A-73) described at pages 49 to 58; compounds represented by (Chem. 21), (Chem. 22) and (Chem. 23) of JP-A-7-84331, specifically, compounds described in pages 6 to 8; and compounds represented by formulae [Na] and [Nb] of JP-A-7-104426, specifically, Compounds Na-1 to Na-22 and Compounds Nb-1 to Nb-12 described at pages 16 to 20.

The nucleation accelerator for use in the present invention may be dissolved in an appropriate water-miscible organic solvent such as alcohols (e.g., methanol, ethanol, propanol, fluorinated alcohol), ketones (e.g., acetone, methyl ethyl ketone), dimethylformamide, dimethylsulfoxide and methyl cellosolve, prior to use.

Alternatively, the nucleation accelerator may be used in the form of an emulsion dispersion product obtained by dissolving the compound according to a well known emulsion dispersion method using an oil such as dibutyl phthalate, tricresyl phosphate, glyceryl triacetate or diethylphthalate, or an auxiliary solvent such as ethyl acetate or cyclohexanone, and mechanically forming it into an emulsion dispersion product. Further, powder of the nucleation accelerator may be dispersed in water according to a method known as a solid dispersion method by means of a ball mill, a colloid mill or ultrasonic waves and then used.

The nucleation accelerator for use in the present invention may be added to any of silver halide emulsion layers and other hydrophilic colloid layers on the silver halide emulsion layer side of the support, however, it is preferably added to the silver halide emulsion layer or a hydrophilic colloid layer adjacent thereto.

The nucleation accelerator of the present invention is preferably added in an amount of from $1\times10^{-6}$ to $2\times10^{-2}$ mol, more preferably from $1\times10^{-5}$ to $2\times10^{-2}$ mol, most preferably from $2\times10^{-5}$ to $1\times10^{-2}$ mol, per mol of silver halide.

The halogen composition of the silver halide emulsion for use in the present invention is not particularly limited, however, in view of achieving the objects of the present invention more effectively, silver chloride, silver chlorobromide or silver chloroiodobromide having a silver chloride content of 50 mol % or more is preferred. The silver iodide content is preferably less than 5 mol %, more preferably less than 2 mol %.

In the present invention, a light-sensitive material suitable for high illuminance exposure such as scanner exposure or a light-sensitive material for photographing line original contains a rhodium compound so as to achieve high contrast and low fog.

The rhodium compound for use in the present invention may be a water-soluble rhodium compound. Examples thereof include rhodium(III) halogenide compounds and rhodium complex salts having a halogen, an amine or an oxalate as a ligand, such as hexachlororhodium(III) complex salt, hexabromo-rhodium(III) complex salt, hexaminerhodium(III) complex salt and trisalaterhodium (III) complex salt. The rhodium compound is dissolved in water or an appropriate solvent prior to use and a method commonly used for stabilizing the rhodium compound solution, namely, a method of adding an aqueous solution of hydrogen halogenide (e.g., hydrochloric acid, bromic acid, hydrofluoric acid) or an alkali halide (e.g., KCl, NaCl, KBr, NaBr), may be used. In place of using a water-soluble rhodium, separate silver halide grains which are previously doped with rhodium may be added and dissolved at the time of preparation of silver halide.

The addition amount of the rhodium compound is from $1\times10^{-8}$ to $5\times10^{-6}$ mol, preferably from $5\times10^{-8}$ to $1\times10^{-6}$ mol, per mol of silver of the silver halide emulsion.

The rhodium compound may be added during production of silver halide emulsion grains or at any appropriate stage before coating of the emulsion, however, it is preferably added at the time of formation of the emulsion to incorporate it into a silver halide grain.

The photographic emulsion for use in the present invention can be prepared using a method described in P. Glafkides, *Chimie et Physique Photographique*, Paul Montel (1967); G.F. Duffin, *Photographic Emulsion Chemistry*, The Focal Press (1966); and V.L. Zelikman et al, *Making and Coating Photographic Emulsion*, The Focal Press (1964).

A soluble silver salt may be reacted with a soluble halogen salt by any of a single jet method, a double jet method and a combination thereof.

A method of forming grains in the presence of excessive silver ions (so-called reverse mixing process) may also be used. As one of the double jet method, a method of maintaining the pAg constant in the liquid phase where silver halide is produced, namely, a so-called controlled double jet method may be used. Further, it is preferred to form grains using a so-called silver halide solvent such as ammonia, thioether or tetra-substituted thiourea, more preferably using a tetra-substituted thiourea compound, and this is described in JP-A-53-82408 and JP-A-55-77737. Preferred examples of the thiourea compound include tetramethyl thiourea and 1,3-dimethyl-2-imidazolidinethione.

According to the controlled double jet method or the method of forming grains using a silver halide solvent, a silver halide emulsion comprising regular crystal form grains and having a narrow grain size distribution can be easily prepared, and these methods are a useful means for preparing the silver halide emulsion for use in the present invention.

In order to achieve a uniform grain size, it is preferred to rapidly grow grains within the range of not exceeding the critical saturation degree, using a method of changing the addition rate of silver nitrate or alkali halide according to the grain growth rate as described in British Patent 1,535,016, JP-B-48-36890 and JP-B-52-16364, or a method of changing the concentration of the aqueous solution as described in British Patent 4,242,445 and JP-A-55-158124.

The emulsion of the present invention is preferably a monodisperse emulsion having a coefficient of variation of 20% or less, more preferably 15% or less.

The grains in the monodisperse silver halide emulsion have an average grain size of 0.5 $\mu$m or less, more preferably from 0.1 to 0.4 $\mu$m.

The silver halide emulsion of the present invention is preferably subjected to chemical sensitization. The chemical sensitization may be performed using a known method such as sulfur sensitization, selenium sensitization, tellurium sensitization or noble metal sensitization, and these sensitization methods may be used individually or in combination. When these sensitization methods are used in combination, a combination of sulfur sensitization and gold sensitization, a combination of sulfur sensitization, selenium sensitization and gold sensitization, and a combination of sulfur sensitization, tellurium sensitization and gold sensitization are preferred.

The sulfur sensitization for use in the present invention is usually performed by adding a sulfur sensitizer and stirring the emulsion at a high temperature of 40° C. or higher for a predetermined time. The sulfur sensitizer may be a known compound and examples thereof include, in addition to the sulfur compound contained in gelatin, various sulfur compounds such as thiosulfates, thioureas, thiazoles and rhodanines. Preferred sulfur compounds are a thiosulfate and a thiourea compound. The addition amount of the sulfur sensitizer varies depending upon various conditions such as the pH and the temperature at the time of chemical ripening and the size of silver halide grains, however, it is usually from $10^{-7}$ to $10^{-2}$ mol, preferably from $10^{-5}$ to $10^{-3}$ mol, per mol of silver halide.

The selenium sensitizer for use in the present invention may be a known selenium compound. The selenium sensitization is usually performed by adding a labile and/or non-labile selenium compound and stirring the emulsion at a high temperature of 40° C. or higher for a predetermined time. Examples of the labile selenium compound include the compounds described in JP-B-44-15748, JP-B-43-13489, JP-A-4-25832, JP-A-4-109240 and JP-A-4-324855, and among these, particularly preferred are the compounds represented by formulae (VIII) and (IX) of JP-A-4-324855.

The tellurium sensitizer for use in the present invention is a compound which generates silver telluride presumed to be a sensitization nucleus, on the surface or in the inside of a silver halide grain. The generating rate of silver telluride in a silver halide emulsion can be examined according to a method described in JP-A-5-313284.

Specific examples of the tellurium sensitizer include the compounds described in U.S. Pat. Nos. 1,623,499, 3,320,069 and 3,772,031, British Patents 235,211, 1,121,496, 1,295,462 and 1,396,696, Canadian Patent 800,958, JP-A-4-204640, JP-A-4-271341, JP-A-4-333043, JP-A-5-303157, J. Chem. Soc. Chem. Commun., 635 (1980), ibid., 1102 (1979), ibid., 645 (1979), J. Chem. Soc. Perkin. Trans., 1, 2191 (1980), S. Patai (compiler), *The Chemistry of Organic Selenium and Tellurium Compounds*, Vol. 1 (1986), and ibid., Vol. 2 (1987). The compounds represented by formulae (II), (III) and (IV) of JP-A-5-313284 are particularly preferred.

The use amount of the selenium sensitizer or the tellurium sensitizer for use in the present invention varies depending upon silver halide grains used or chemical ripening conditions, however, it is usually approximately from $10^{-8}$ to $10^{-2}$ mol, preferably approximately from $10^{-7}$ to $10^{-3}$ mol, per mol of silver halide. The conditions for chemical sensitization in the present invention are not particularly limited, however, the pH is generally from 5 to 8, the pAg is generally from 6 to 11, preferably from 7 to 10, and the temperature is from 40° to 95° C., preferably from 45° to 85° C.

Examples of the noble metal sensitizer for use in the present invention include gold, platinum, palladium and iridium, and gold sensitization is particularly preferred. Specific examples of the gold sensitizer for use in the present invention include chloroauric acid, potassium chlorate, potassium aurithiocyanate and gold sulfide, and the gold sensitizer is used in an amount of approximately from $10^{-7}$ to $10^{-2}$ mol per mol of silver halide.

In the silver halide emulsion for use in the present invention, a cadmium salt, a sulfite, a lead salt or a thallium salt may be present together during formation or physical ripening of silver halide grains.

In the present invention, reduction sensitization may be used. Examples of the reduction sensitizer which can be used include stannous salt, amines, formamidinesulfinic acid and silane compounds.

To the silver halide emulsion of the present invention, a thiosulfonic acid compound may be added according to the method described in European Unexamined Patent Publication EP-A-293917.

In the light-sensitive material for use in the present invention, one kind of silver halide emulsion may be used or two or more kinds of silver halide emulsions (for example, those having different average grain sizes, different halogen compositions, different crystal habits, or different chemical sensitization conditions) may be used in combination.

In the present invention, the silver halide emulsion particularly suitable as a light-sensitive material for dot-to-dot work comprises silver halide having a silver chloride content of 90 mol % or more, preferably 95 mol % or more, more specifically, silver chlorobromide or silver chloroiodobromide containing from 0 to 10 mol % of silver bromide. If the proportion of silver bromide or silver iodide increases, the safelight safety in a bright room may be worsened or the $\gamma$ value is disadvantageously lowered.

The silver halide emulsion for use in the dot-to-dot work light-sensitive material of the present invention preferably contains a transition metal complex, and examples of the transition metal include Rh, Ru, Re, Os, Ir and Cr.

Examples of the ligand include a nitrosyl bridging ligand, a thionitrosyl bridging ligand, a halogen ligand (e.g., fluorine, chlorine, bromine, iodine), a cyanide ligand, a cyanate ligand, a thiocyanate ligand, a selenocyanate ligand, a tellurocyanate ligand, an acid ligand and an aquo ligand. When an aquo ligand is present, it preferably occupies one or more of the ligands.

More specifically, the rhodium atom may be incorporated by forming it into a metal salt in any form, such as a single salt or a complex salt, and adding the salt at the time of preparation of grains.

Examples of the rhodium salt include rhodium monochloride, rhodium dichloride, rhodium trichloride and ammonium hexachlororhodate, and preferred are a halogen complex compound of water-soluble trivalent rhodium, such as hexachlororhodium(III) acid and a salt thereof (e.g., ammonium salt, sodium salt, potassium salt).

The addition amount of the water-soluble rhodate is from $1.0 \times 10^{-6}$ to $1.0 \times 10^{-3}$, preferably from $1.0 \times 10^{-5}$ to $1.0 \times 10^{-3}$, more preferably from $5.0 \times 10^{-5}$ to $5.0 \times 10^{-4}$ mol, per mol of silver halide.

The following transition metal complexes are also preferred.

1. $[RU(NO)Cl_5]^{-2}$
2. $[Ru(NO)_2Cl_4]^{-1}$
3. $[Ru(NO)(H_2O)Cl_4]^{-1}$
4. $[Rh(NO)Cl_5]^{-2}$
5. $[Re(NO)CN_5]^{-2}$
6. $[Re(NO)ClCN_4]^{-2}$
7. $[Rh(NO)_2Cl_4]^{-1}$
8. $[Rh(NO)(H_2O)Cl_4]^{-1}$
9. $[Ru(NO)CN_5]^{-2}$
10. $[Ru(NO)Br_5]^{-2}$
11. $[Ru(NS)Cl_5]^{-2}$
12. $[Os(NO)Cl_5]^{-2}$
13. $[Cr(NO)Cl_5]^{-3}$
14. $[Re(NO)Cl_5]^{-1}$
15. $[Os(NS)Cl_4(TeCN)]^{-2}$
16. $[Ru(NS)I_5]^{-2}$
17. $[Re(NS)Cl_4(SeCN)]^{-2}$
18. $[Os(NS)Cl(SCN)_4]^{-2}$
19. $[Ir(NO)Cl_5]^{-2}$

The spectral sensitizing dye for use in the present invention is not particularly limited.

The addition amount of the sensitizing dye for use in the present invention varies depending upon the shape or size of silver halide grains, however, it is usually from $4\times10^{-6}$ to $8\times10^{-3}$ mol per mol of silver halide. For example, when the silver halide grain size is from 0.2 to 1.3 μm, the addition amount is preferably from $2\times10^{-7}$ to $3.5\times10^{-6}$ mol, more preferably from $6.5\times10^{-7}$ to $2.0\times10^{-6}$ mol, per 1 $m^2$ of the surface area of silver halide grains.

The light-sensitive silver halide emulsion for use in the present invention may be spectrally sensitized to blue light, green light, red light or infrared light, each having a relatively long wavelength, by a sensitizing dye. Examples of the sensitizing dye which can be used include a cyanine dye, a merocyanine dye, a complex cyanine dye, a complex merocyanine dye, a holopolar cyanine dye, a styryl dye, a hemicyanine dye, an oxonol dye and a hemioxonol dye.

Useful sensitizing dyes for use in the present invention are described, for example, in *Research Disclosure*, Item 17643, IV-A, page 23 (December, 1978), ibid., Item 18431X, page 437 (August, 1979), and publications cited therein. In particular, sensitizing dyes having spectral sensitivity suitable for spectral characteristics of various scanner light sources can be advantageously selected to use.

For example, A) for an argon laser light source, simple merocyanines described in JP-A-60-162247, JP-A-2-48653, U.S. Pat. No. 2,161,331, West German Patent 936,071 and JP-A-5-11389, B) for a helium-neon laser light source, trinuclear cyanine dyes described in JP-A-50-62425, JP-A-54-18726 and JP-A-59-102229, C) for an LED light source and a red semiconductor laser, thiacarbocyanines described in JP-B-48-42172, JP-B-51-9609, JP-B-55-39818, JP-A-62-284343 and JP-A-2-105135, and D) for an infrared semiconductor laser light source, tricarbocyanines described in JP-A-59-191032 and JP-A-60-80841, and dicarbocyanines containing a 4-quinoline nucleus described in JP-A-59-192242 and JP-A-3-67242, formulae (IIIa) and (IIIb), may be advantageously selected to use.

These sensitizing dyes may be used individually or in combination, and the combination of sensitizing dyes is often used for the purpose of supersensitization. In combination with the sensitizing dye, a dye which itself has no spectral sensitization effect or a material which absorbs substantially no visible light, but exhibits supersensitization may be incorporated into the emulsion.

Useful sensitizing dyes, combinations of dyes which exhibit supersensitization, and materials which show supersensitization are described in *Research Disclosure*, Vol. 176, 17643, page 23, Item IV-J (December, 1978).

For the argon laser light source, specifically, Compounds (I)-1 to (I)-8 described in JP-A-60-162247, Compounds I-1 to I-28 described in JP-A-2-48653, Compounds I-1 to I-13 described in JP-A-4-330434, compounds in Examples 1 to 14 of U.S. Pat. No. 2,161,331, and Compounds 1 to 7 described in West German Patent 936,071 are advantageously used.

For the helium-neon light source, Compounds I-1 to I-38 described in JP-A-54-18726, Compounds I-1 to I-35 described in JP-A-6-75322, and Compounds I-1 to I-34 described in JP-A-7-287338 are advantageously used.

For the LED light source, Dyes 1 to 20 described in JP-B-55-39818, Compounds I-1 to I-37 described in JP-A-62-284343, and Compounds I-1 to I-34 described in JP-A-7-287338 are advantageously used.

For the semiconductor laser light source, Compounds I-1 to I-12 described in JP-A-59-191032, Compounds I-1 to I-22 described in JP-A-60-80841, Compounds I-1 to I-29 described in JP-A-4-335342, and Compounds I-1 to I-18 described in JP-A-59-192242 are advantageously used.

For the tungsten and xenon light source in camera work, Compounds (1) to (19) represented by general formula (I) described in JP-A-55-45015, and Compounds 4-A to 4-S, 5-A to 5-Q, and 6-A to 6-T described in JP-A-6-242547 are advantageously used.

The developer for use in developing the light-sensitive material of the present invention may contain additives (e.g., developing agent, alkali agent, pH buffer, preservative, chelating agent) which are commonly used. The development of the present invention may be performed by any of known methods, and a known development processing solution may be used.

The developing agent for use in the developer for the present invention is not particularly limited, however, it preferably contains a dihydroxybenzene or an ascorbic acid derivative, and in view of developing capability, a combination of a dihydroxybenzene with a 1-phenyl-3-pyrazolidone, a combination of a dihydroxybenzene with a p-aminophenol, a combination of an ascorbic acid derivative with a 1-phenyl-3-pyrazolidone and a combination of an ascorbic acid derivative and a p-aminophenol are preferred.

Examples of the dihydroxybenzene developing agent for use in the present invention include hydroquinone, chlorohydroquinone, isopropylhydroquinone, methylhydroquinone and hydroquinone monosulfonate, with hydroquinone being particularly preferred.

Examples of the ascorbic acid derivative developing agent for use in the present invention include an ascorbic acid, an erythorbic acid as a stereoisomer thereof and an alkali metal salt (e.g., sodium salt, potassium salt) thereof.

Examples of the 1-phenyl-3-pyrazolidone or a derivative thereof as the developing agent for use in the present invention include 1-phenyl-3-pyrazolidone, 1-phenyl-4,4-dimethyl-3-pyrazolidone and 1-phenyl-4-methyl-4-hydroxymethyl-3-pyrazolidone.

Examples of the p-aminophenol-base developing agent for use in the present invention include N-methyl-p-aminophenol, p-aminophenol, N-(β-hydroxyethyl)-p-aminophenol and N-(4-hydroxyphenyl)glycine, with N-methyl-p-aminophenol being particularly preferred.

The dihydroxybenzene-base developing agent is usually preferably used in an amount of from 0.05 to 0.8 mol/l, more preferably from 0.2 to 0.6 mol/l. In the case when a dihydroxybenzene and a 1-phenyl-3-pyrazolidone or a p-aminophenol are used in combination, the former is preferably used in an amount of from 0.05 to 0.6 mol/l, more preferably from 0.2 to 0.5 mol/l, and the latter is preferably used in an amount of 0.06 mol/l or less, more preferably 0.03 mol/l or less.

The ascorbic acid derivative developing agent is usually preferably used in an amount of from 0.05 to 0.8 mol/l, more preferably from 0.2 to 0.6 mol/l. In the case when an ascorbic acid derivative and a 1-phenyl-3-pyrazolidone or a p-aminophenol are used in combination, the former is preferably used in an amount of from 0.05 to 0.6 mol/l, more preferably from 0.2 to 0.5 mol/l, and the latter is preferably used in an amount of 0.06 mol/l or less, more preferably 0.03 mol/l or less.

Examples of the preservative for use in the present invention include sodium sulfite, potassium sulfite, lithium sulfite, ammonium sulfite, sodium bisulfite, potassium metabisulfite and sodium formaldehyde bisulfite. The sulfite is used in an amount of 0.20 mol/l or more, preferably 0.3 mol/l or more, however, if it is added in excess, silver stains are caused in the developer, and therefore, the upper limit of the use amount is preferably 1.2 mol/l. The sulfite is used more preferably in an amount of from 0.35 to 0.7 mol/l.

As the preservative of the dihydroxybenzene-base developing agent, a small amount of an ascorbic acid derivative may be used in combination with the sulfite. The ascorbic acid derivative includes an ascorbic acid, an erythorbic acid as a stereoisomer thereof, and an alkali metal salt thereof (e.g., sodium salt, potassium salt), and sodium erythorbate is preferred in view of the cost for materials. The addition amount thereof is, in terms of molar ratio to the dihydroxybenzene-base developing agent, preferably from 0.03 to 0.12, more preferably from 0.05 to 0.10. In the case where an ascorbic acid derivative is used as the preservative, the developer preferably contains no boron compound.

The alkali agent used for adjusting the pH may be a normal water-soluble inorganic alkali metal salt (e.g., sodium hydroxide, potassium hydroxide, sodium carbonate, potassium carbonate). The developer preferably has a pH of from 9.0 to 12.0. More preferably, by adjusting the pH to from 9.0 to 11.0, a stable processing system can be established.

Examples of additives other than those described above include a development inhibitor such as sodium bromide and potassium bromide; an organic solvent such as ethylene glycol, diethylene glycol, triethylene glycol and dimethylformamide; a development accelerator such as alkanolamine (e.g., diethanolamine, triethanolamine), imidazole and a derivative thereof; and an antifoggant or a black pepper inhibitor such as a mercapto-base compound, an imidazole-base compound, a benzotriazole-base compound and a benzimidazole-base compound. Specific examples thereof include 5-nitroindazole, 5-p-nitrobenzoylaminoindazole, 1-methyl-5-nitroindazole, 6-nitroindazole, 3-methyl-5-nitroindazole, 5-nitrobenzimidazole, 2-isopropyl-5-nitrobenzimidazole, 5-nitrobenzotriazole, sodium 4-[(2-mercapto-1,3,4-thiadiazol-2-yl)thio]butanesulfonate, 5-amino-1,3,4-thiadiazole-2-thiol, methylbenzotriazole, 5-methylbenzotriazole and 2-mercaptobenzotriazole. The antifoggant is usually used in an amount of from 0.01 to 10 mmol, preferably from 0.1 to 2 mmol, per l of the developer.

The developer of the present invention can further contain various organic or inorganic chelating agent in combination.

Examples of the inorganic chelating agent include sodium tetrapolyphosphate and sodium hexametaphosphate.

Examples of the organic chelating agent which can be predominantly used, include an organic carboxylic acid, an aminopolycarboxylic acid, an organic phosphonic acid, an aminophosphonic acid and an organic phosphonocarboxylic acid.

Examples of the organic carboxylic acid include an acrylic acid, an oxalic acid, a malonic acid, a succinic acid, a glutaric acid, an adipic acid, a pimelic acid, an azelaic acid, a sebacic acid, a nonanedicarboxylic acid, a decanedicarboxylic acid, an undecanedicarboxylic acid, a maleic acid, an itaconic acid, a malic acid, a citric acid and a tartaric acid, however, the organic carboxylic acid is not limited thereto.

Examples of the aminopolycarboxylic acid include iminodiacetic acid, nitrilotriacetic acid, nitrilotripropionic acid, ethylenediaminemonohydroxyethyltriacetic acid, ethylenediaminetetraacetic acid, glycolethertetraacetic acid, 1,2-diaminopropanetetraacetic acid, diethylenetriaminepentaacetic acid, triethylenetetraminehexaacetic acid, 1,3-diamino-2-propanoltetraacetic acid, glycoletherdiaminetetraacetic acid, and the compounds described in JP-A-52-25632, JP-A-55-67747, JP-A-57-102624 and JP-B-53-40900.

Examples of the organic phosphonic acid include hydroxyalkylidenediphosphonic acid described in U.S. Pat. Nos. 3,214,454 and 3,794,591 and German Patent Application (OLS) No. 2,227,639, and the compounds described in *Research Disclosure*, Vol. 181, Item 18170 (May, 1979).

Examples of the aminophosphonic acid include aminotris (methylenephosphonic acid), ethylenediaminetetramethylenephosphonic acid, aminotrimethylenephosphonic acid, and the compounds described in *Research Disclosure* (supra), No. 18170, JP-A-57-208554, JP-A-54-61125, JP-A-55-29883 and JP-A-56-97347.

Examples of the organic phosphonocarboxylic acid include the compounds described in JP-A-52-102726, JP-A-53-42730, JP-A-54-121127, JP-A-55-4024, JP-A-55-4025, JP-A-55-126241, JP-A-55-65955, JP-A-55-65956 and *Research Disclosure* (supra), No. 18170.

These chelating agents each may be used in the form of an alkali metal salt or an ammonium salt. The chelating agent is preferably added in an amount of from $1 \times 10^{-4}$ to $1 \times 10^{-1}$ mol, more preferably from $1 \times 10^{-3}$ to $1 \times 10^{-2}$ mol, per l of the developer.

The developer may contain the compound described in JP-A-56-24347, JP-B-56-46585, JP-B-62-2849 or JP-A-4-362942 as a silver stain inhibitor.

Further, the developer may contain the compound described in JP-A-62-212651 as a development unevenness inhibitor, and the compound described in JP-A-61-267759 as a dissolution aid.

Furthermore, the developer may contain a color toner, a surface active agent, a defoaming agent or a hardening agent, if desired.

The developer for use in the present invention may contain as a buffer, a carbonate, a boric acid described in JP-A-62-186259, a saccharide (e.g., succarose) described in JP-A-60-93433, an oxime (e.g., acetoxime), a phenol (e.g., 5-sulfosalicylic acid) or a tertiary phosphate (e.g., sodium salt, potassium salt). Of these, a carbonate and a boric acid are preferably used.

The development processing temperature and the development processing time are correlated with each other and they are determined taking account of the entire processing time, however, the development temperature is generally from about 20° C. to about 50° C., preferably from 25° to 45° C., and the development time is generally from 5 seconds to 2 minutes, preferably from 7 seconds to 1.5 minutes.

When a silver halide black-and-white photographic light-sensitive material according to the present invention is processed, the replenisher of the developer is supplied in an amount of 500 ml or less, preferably 400 ml or less, per 1 m$^2$ of the silver halide light-sensitive material.

For saving the cost for transportation of processing solutions, the cost for packaging materials or the space for installation, the processing solution are preferably concentrated and diluted on use. In order to concentrate the developer, it is effective to process the salt components contained in the developer into a potassium salt form.

The fixing solution for use in the fixing step of the present invention is an aqueous solution containing sodium thiosulfate or ammonium thiosulfate and if desired, tartaric acid, citric acid, gluconic acid, boric acid, iminodiacetic acid, 5-sulfosalicylic acid, glucoheptanoic acid, tylon, ethylenediaminetetraacetic acid, diethylenetriaminepentaacetic acid, nitrilotriacetic acid or a salt thereof. In view of environmental consideration in recent years, the fixing solution preferably contains no boric acid.

The fixing agent in the fixing solution for use in the present invention includes sodium thiosulfate and ammonium thiosulfate, and in view of the fixing rate, ammonium thiosulfate is preferred. However, when taken account of environmental consideration in recent years, sodium thiosulfate may be used. The use amount of these known fixing agents may be varied appropriately, however, it is generally from about 0.1 to about 2 mol/l, preferably from 0.2 to 1.5 mol/l.

The fixing solution may contain, if desired, a hardening agent (e.g., water-soluble aluminum compound), a preservative (e.g., sulfite, bisulfite), a pH buffer (e.g., acetic acid), a pH adjusting agent (e.g., ammonia, sulfuric acid), a chelating agent, a surface active agent, a wetting agent or a fixing accelerator.

Examples of the surface active agent include an anionic surface active agent such as sulfated product and sulfonated product, a polyethylene-base surface active agent, and an amphoteric surface active agent described in JP-A-57-6740. A known defoaming agent may also be added. Examples of the wetting agent include alkanolamines and alkylene glycols. Examples of the fixing accelerator include thiourea derivatives described in JP-B-45-35754, JP-B-58-122535 and JP-B-58-122536, alcohols having a triple bond within a molecule, thioether compounds described in U.S. Pat. No. 4,126,459, meso-ionic compounds described in JP-A-4-229860, and the compounds described in JP-A-2-44355.

Examples of the pH buffer include an organic acid such as acetic acid, malic acid, succinic acid, tartaric acid, citric acid, oxalic acid, maleic acid, glycolic acid and adipic acid, and an inorganic buffer such as boric acid, phosphate and sulfite. Among these, preferred are acetic acid, tartaric acid and sulfite.

The pH buffer is used here to prevent an increase of the pH value of the fixing agent due to carrying over of the developer, and it is used in an amount of from 0.01 to 1.0 mol/l, preferably approximately from 0.02 to 0.6 mol/l.

The fixing solution may also contain the compound described in JP-A-64-4739 as a dye elution accelerator.

Examples of the hardening agent in the fixing solution of the present invention include a water-soluble aluminum salt and a chromium salt. Of these, a water-soluble aluminum salt is preferred and examples thereof include aluminum chloride, aluminum sulfate and potassium alum. The addition amount thereof is preferably from 0.01 to 0.2 mol/l, more preferably from 0.03 to 0.08 mol/l.

The fixing temperature is generally from about 20° C. to about 50° C., preferably from 25° to 45° C., and the fixing time is generally from 5 seconds to 1 minute, preferably from 7 to 50 seconds.

The replenishing amount of the fixing solution is generally 600 ml/m$^2$ or less, preferably 500 ml/m$^2$ or less, based on the light-sensitive material processed.

The light-sensitive material processed through development and fixing is then subjected to water washing or stabilization.

The water washing or stabilization is usually performed using water in an amount of 20 l or less per m$^2$ of the silver halide light-sensitive material and they may be performed at a replenishing amount of 3 l or less (including 0, namely, standing water washing). More specifically, the processing can not only be performed with saved water but also dispense with piping for installation of an automatic developing machine.

As a method for reducing the replenishing amount of washing water, a multi-stage countercurrent system (for example, two stages or three stages) has been known. When the multi-stage countercurrent system is applied to the present invention, the light-sensitive material after fixing is processed gradually toward the correct direction, namely, while coming into contact in sequence with processing solutions unstained with the fixing solution, and as a result, water washing can be performed more efficiently.

When water washing is performed with a small amount of water, a rinsing tank such as squeeze roller or cross-over roller described in JP-A-63-18350 and JP-A-62-28725 is preferably provided. Alternatively, addition of various oxidizing agents or filter filtration may be combined so as to reduce the pollution load which is a problem to be caused in water washing with a small amount of water.

The over-flow solution from the water washing or stabilization bath, which is generated as a result of replenishing water with an antimold means to the water washing or stabilization bath by the method of the present invention, may be partially or wholly used in the processing solution having fixing ability as the previous processing step thereof as described in JP-A-60-235133.

Also, a water-soluble surface active agent or a defoaming agent may be added so as to prevent uneven processing due to bubbling which is liable to occur at the time of water washing with a small amount of water, and/or to prevent a processing agent component adhering to the squeeze roller from transferring onto the processed film.

Further, a dye adsorbent described in JP-A-63-163456 may be provided in the water washing tank so as to prevent stain due to a dye dissolved out from the light-sensitive material.

In some cases, stabilization may be performed following the above-described water washing, and an example thereof is the bath containing the compound described in JP-A-2-201357, JP-A-2-132435, JP-A-1-102553 or JP-A-46-44446 used as a final bath of the light-sensitive material.

The stabilizing bath may also contain, if desired, an ammonium compound, a metal compound such as Bi and Al, a fluorescent brightening agent, various chelating agents, a film pH adjusting agent, a hardening agent, a sterilizer, an antimold, an alkanolamine or a surface active agent. Water for use in the water washing or stabilization step may be tap water, but deionized water or water subjected to sterilization with a halogen or ultraviolet bactericidal lamp or various oxidizing agents (e.g., ozone, hydrogen peroxide, chlorate)

is preferably used. Further, washing water containing the compound described in JP-A-4-39652 or JP-A-5-241309 may also be used.

The temperature and the time in water washing or stabilization are preferably from 0° to 50° C. and from 5 seconds to 2 minutes, respectively.

The processing solution for use in the present invention is preferably stored in a packaging material having a low oxygen permeability described in JP-A-61-73147.

The processing solution for use in the present invention may be formed into powder or a solid. To this effect, the methods described in JP-A-61-259921, JP-A-4-85533 and JP-A-4-16841 are preferably used. In particular, the method described in JP-A-61-259921 is preferred.

When the replenishing amount is reduced, the contact area of the processing tank with air is preferably made small so as to prevent evaporation or air oxidation of the solution. The roller transportation-type automatic developing machine is described in U.S. Pat. Nos. 3,025,779 and 3,545,971. In the present invention, the developing machine of this type is simply referred to as a roller transportation-type processor. The roller transportation-type processor generally composed of four processing steps of development, fixing, water washing and drying. It is most preferred that this four-step system is followed also in the present invention, though use of other steps (for example, stopping) is not excluded. In the four-step system, water washing may be replaced by stabilization.

The hydrazine nucleating agent for use in the present invention may also be used in the method for obtaining a direct positive image by surface developing an internal latent image-type silver halide photographic emulsion in the presence of a nucleating agent, or in the photographic emulsion or the light-sensitive material used in such a method (as those described, for examples, in U.S. Pat. Nos. 2,456,953, 2,497,875, 2,497,876, 2,588,982, 2,592,250, 2,675,318, 3,227,552 and 3,317,322, British Patents 1,011,062, 1,151,363, 1,269,640 and 2,011,391, JP-B-43-29405, JP-B-49-38164, JP-A-53-16623, JP-A-53-137133, JP-A-54-37732, JP-A-54-40629, JP-A-54-74536, JP-A-54-74729, JP-A-55-52055 and JP-A-55-90940).

In the above-described method for obtaining a direct positive image, the nucleating agent may be added to the developer, however, it is more commonly added to a photographic emulsion layer or other appropriate layer of a light-sensitive material.

Various additives for use in the light-sensitive material of the present invention and the development processing method are not particularly limited, and for example, those described in the following portions may be preferably used.

| Item | Pertinent Portion |
|---|---|
| 1) Surface active agent | JP-A-2-12236, page 9, from right upper column, line 7 to right lower column, line 7, and JP-A-2-18542, from page 2, left lower column, line 13 to page 4, right lower column, line 18 |
| 2) Antifoggant | JP-A-2-103536, from page 17, right lower column, line 19 to page 18, right upper column, line 4 and page 18, right lower column, lines 1 to 5, and thiosulfinic acid compounds described in JP-A- |

-continued

| Item | Pertinent Portion |
|---|---|
| | 1-237538 |
| 3) Polymer latex | JP-A-2-103536, page 18, left lower column, lines 12 to 20 |
| 4) Compound having acid radical | JP-A-2-103536, from page 18, right lower column, line 6 to page 19, left upper column, line 1 |
| 5) Matting agent, slipping agent and plasticizer | JP-A-2-103536, from page 19, left upper column, line 15 to right upper column, line 15 |
| 6) Hardening agent | JP-A-2-103536, page 18, right upper column, lines 5 to 17 |
| 7) Dye | dyes described in JP-A-2-103536, page 17, right lower column, lines 1 to 18, and solid dyes described in JP-A-2-294638 and JP-A-5-11382 |
| 8) Binder | JP-A-2-18542, page 3, right lower column, lines 1 to 20 |
| 9) Black pepper inhibitor | compounds described in U.S. Patent 4,956,257 and JP-A-1-118832 |
| 10) Redox compound | compounds represented by formula (I) of JP-A-2-301743 (particularly, Compounds 1 to 50), compounds represented by formulae (R-1), (R-2) and (R-3) and Compounds 1 to 75 of JP-A-3-174143, pages 3 to 20, and compounds described in JP-A-5-257239 |
| 11) Monomethine compound | compounds represented by formula (II) of JP-A-2-287532 (particularly Compounds II-1 to II-26) |
| 12) Dihydroxybenzenes | compounds described in JP-A-3-39948, from page 11, left upper column to page 12, left lower column, and EP-A-452772 |

The present invention is described in more detail below with reference to the following Examples, but the invention should not be construed as being limited thereto.

EXAMPLE 1

Preparation of Solid Dispersion of Hydrazide Compound

A 25% aqueous solution of Demol SNB (produced by Kao Corporation) was prepared. Then, to 0.5 g of a hydrazide compound shown in Table 6, 0.6 g of the Demol SNB aqueous solution prepared above and 59 g of water were added to prepare a slurry. The resulting slurry was charged in a dispersing machine (1/16 gallon, Sand Grinder Mill (manufactured by Aimex K.K.)) and dispersed for 15 hours using, as the media, 170 g of glass beads having a diameter of from 0.8 to 1.2 mm. Thereafter, an aqueous gelatin solution was added and mixed to obtain a hydrazide compound concentration of 0.5% and a gelatin concentration of 5%, and then proxel as an antiseptic was added in an amount of 2,000 ppm based on the gelatin. Finally, an ascorbic acid was added to adjust the pH to 5.0. An average particle size of each solid dispersion of hydrazide compound is shown in Tables 2-1 and 2-2.

For comparison with the hydrazide compound of the present invention, the following hydrazide compounds were used.

Comparative Compound 1:
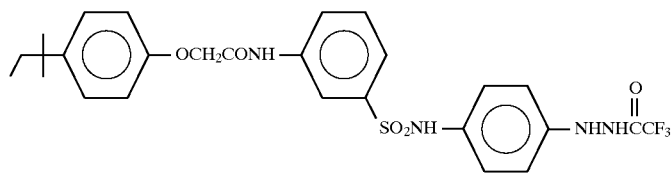
Comparative Compound 2:
(Compound 10 described in JP-A-5-197091)
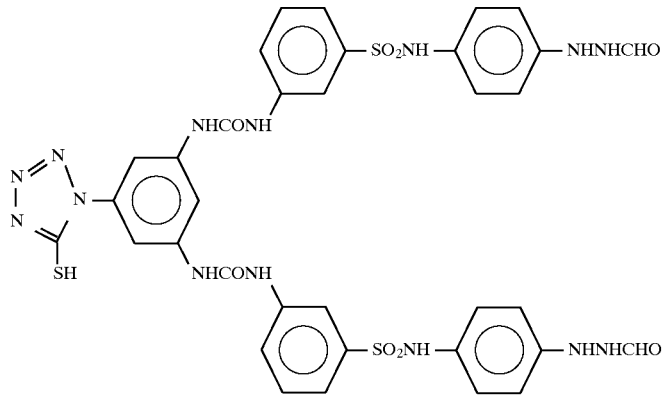
Comparative Compound 3:
(Compound I-43 decribed in JP-A-5-142688)
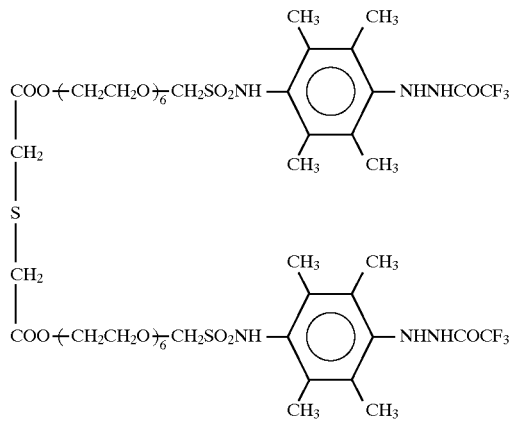
Comparative Compound 4:
(Compound 24 decribed in JP-A-6-148777)
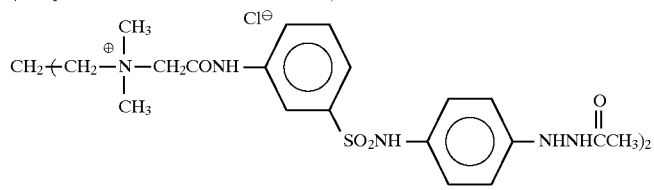
Comparative Compound 1':
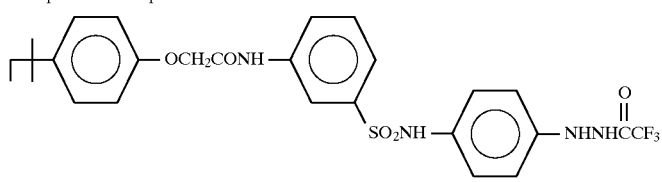

-continued
Comparative Compound 2':
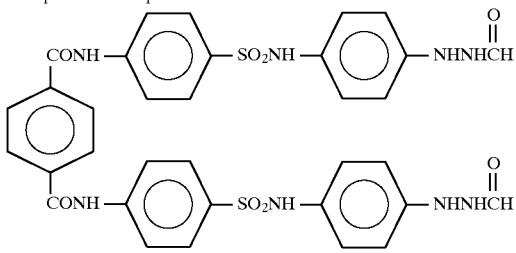
Comparative Compound 3'
(Chem. 19 described in JP-A-5-197091)
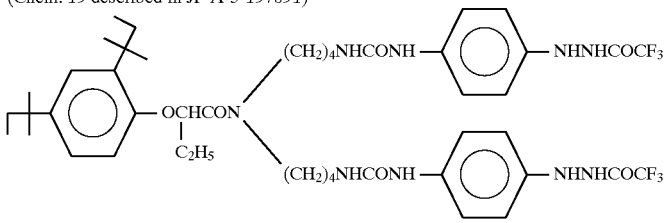
Comparative Compound 4':
(Compound I-43 decribed in JP-A-5-142688)
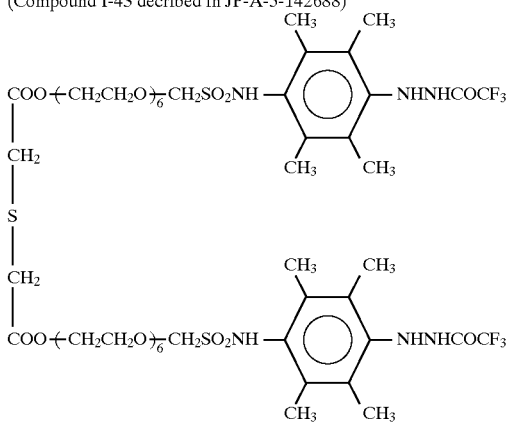
Comparative Compound 5':
(Compound 25 described in JP-A-6-148777)
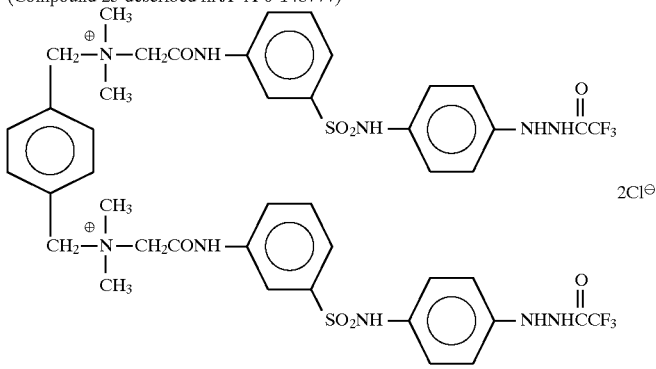
TABLE 2-1
| Solid Dispersion No. | Hydrazide Compound | Average Particle Size ($\mu$m) |
|---|---|---|
| K-1 | Comparative Compound 1 | 0.21 |
| K-2 | Comparative Compound 2 | 0.39 |
| K-3 | Comparative Compound 3 | 0.41 |

TABLE 2-1-continued

| Solid Dispersion No. | Hydrazide Compound | Average Particle Size ($\mu$m) |
|---|---|---|
| K-4 | Comparative Compound 4 | 0.41 |
| K-5 | 1c | 0.50 |
| K-6 | 3c | 0.49 |
| K-7 | 4c | 0.39 |
| K-8 | 5c | 0.40 |
| K-9 | 6c | 0.40 |
| K-10 | 10c | 0.45 |
| K-11 | 11c | 0.35 |
| K-12 | 12c | 0.38 |
| K-13 | 16c | 0.41 |
| K-14 | 19c | 0.42 |
| K-15 | 34 | 0.41 |
| K-16 | 1d | 0.39 |
| K-17 | 3d | 0.48 |
| K-18 | 4d | 0.47 |
| K-19 | 5d | 0.39 |
| K-20 | 6d | 0.40 |
| K-21 | 10d | 0.50 |
| K-22 | 11d | 0.50 |
| K-23 | 12d | 0.38 |
| K-24 | 16d | 0.39 |
| K-25 | 19d | 0.43 |

TABLE 2-2

| Solid Dispersion No. | Hydrazide Compound | Average Particle Size ($\mu$m) |
|---|---|---|
| K-1' | Comparative Compound 1' | 0.21 |
| K-2' | Comparative Compound 2' | 0.50 |
| K-3' | Comparative Compound 3' | 0.45 |
| K-4' | Comparative Compound 4' | 0.41 |
| K-5' | Comparative Compound 5' | 0.37 |
| K-6' | 1a' | 0.49 |
| K-7' | 2a' | 0.36 |
| K-8' | 3a' | 0.39 |
| K-9' | 4a' | 0.40 |
| K-10' | 5a' | 0.48 |
| K-11' | 6a' | 0.47 |
| K-12' | 7a' | 0.45 |
| K-13' | 8a' | 0.41 |
| K-14' | 9a' | 0.43 |
| K-15' | 10a' | 0.50 |
| K-16' | 12a' | 0.37 |
| K-17' | 13a' | 0.35 |
| K-18' | 14a' | 0.40 |
| K-19' | 1b' | 0.39 |
| K-20' | 2b' | 0.44 |
| K-21' | 3b' | 0.45 |
| K-22' | 4b' | 0.49 |
| K-23' | 5b' | 0.48 |
| K-24' | 6b' | 0.48 |
| K-25' | 7b' | 0.48 |
| K-26' | 8b' | 0.38 |
| K-27' | 9b' | 0.47 |
| K-28' | 10b' | 0.49 |
| K-29' | 12b' | 0.49 |
| K-30' | 13b' | 0.39 |
| K-31' | 14b' | 0.40 |
| K-32' | 32' | 0.45 |

EXAMPLE 2

Preparation of Silver Halide Photographic Light-Sensitive Material (Preparation of Emulsion A)

An aqueous silver nitrate solution and an aqueous halogen salt solution containing potassium bromide, sodium chloride, $K_3IrCl_6$ corresponding to $3.5 \times 10^{-7}$ mol/mol-Ag and $K_2Rh(H_2O)Cl_5$ corresponding to $2.0 \times 10^{-7}$ mol/mol-Ag, were added to an aqueous gelatin solution containing sodium chloride and 1,3-dimethyl-2-imidazolidinethione, while stirring by a double jet method to prepare silver chlorobromide grains having an average grain size of 0.25 $\mu$m and a silver chloride content of 70 mol %.

Thereafter, the grains were washed with water by flocculation according to a usual method, 40 g/mol-Ag of gelatin was added thereto, then 7 mg/mol-Ag of sodium benzenethiosulfonate and 2 mg/mol-Ag of benzenesulfinic acid were further added, and the pH and the pAg were adjusted to 6.0 and 7.5, respectively. Thereto, 2 mg/mol-Ag of sodium thiosulfate and 4 mg/mol-Al of chloroauric acid were added, and the mixture was subjected to chemical sensitization to have an optimal sensitivity at 60° C. Then, 150 mg of 4-hydroxy-6-methyl-1,3,3a,7-tetraazaindene as a stabilizer and 100 mg of proxel as an antiseptic were added. The resulting grains were silver chlorobromide cubic grains having an average grain size of 0.25 $\mu$m and a silver chloride content of 70 mol % (coefficient of variation: 10%).

(Preparation of Coated Sample)

On a polyethylene terephthalate film support undercoated by a moisture-proofing layer containing vinylidene chloride, a UL layer, an EM layer, a PC layer and an OC layer were coated in this order from the support side to prepare a sample.

The preparation method and the coating amount of each layer are described below.

(UL Layer)

To an aqueous gelatin solution, a dispersion of polyethyl acrylate was added in an amount of 30 wt % based on the gelatin and the mixture was coated to have a gelatin coverage of 0.5 g/m².

(EM Layer)

To Emulsion A prepared above, $5 \times 10^{-4}$ mol/mol-Ag of Compound (S-1) shown below and $5 \times 10^{-4}$ mol/mol-Ag of Compound (S-2) shown below were added as sensitizing dyes, and further $3 \times 10^{-4}$ mol/mol-Ag of a mercapto compound shown below as Compound (a), $4 \times 10^{-4}$ mol/mol-Ag of a mercapto compound shown below as Compound (b), $4 \times 10^{-4}$ mol/mol-Ag of a triazine compound shown below as Compound (c), $2 \times 10^{-3}$ mol/mol-Ag of 5-chloro-8-hydroxyquinoline, $5 \times 10^{-4}$ mol/mol-Ag of a nucleation accelerator shown below as Compound (A) and $5 \times 10^{-4}$ mol/mol-Ag of a surface active agent shown below as Compound (p) were added. Furthermore, hydroquinone and N-oleyl-N-methyltaurine sodium salt were added to give a coated amount of 100 mg/m² and 30 mg/m², respectively. Then, a solid dispersion of hydrazide compound prepared in Example 1 as a nucleating agent was added as shown in Table 7 in an amount of $5 \times 10^{-4}$ mol/mol-Ag in terms of the hydrazide compound. Further, 200 mg/m² of a water-soluble latex shown below as Compound (d), 200 mg/m² of a polyethyl acrylate dispersion, 200 mg/m² a latex copolymer of methyl acrylate, 2-acrylamido-2-methylpropanesulfonic acid sodium salt and 2-acetoacetoxyethyl methacrylate (weight ratio: 88:5:7), 200 mg/m² of colloidal silica having an average particle size of 0.02 $\mu$m, 200 mg/m² of 1,3-divinylsulfonyl-2-propanol as a hardening agent and 30 mg/m² of sodium polystyrenesulfonate as a thickener were added. The resulting solution was adjusted to have a pH of 5.65 using an acetic acid. Then, the solution was coated to have a coated silver amount of 2.8 g/m².

(PC Layer)

To an aqueous gelatin solution, a dispersion of ethyl acrylate was added in an amount of 50 wt % based on the gelatin. Thereto, Surface Active Agent (w) shown below and 1,5-dihydroxy-2-benzaldoxime were added to give a coated amount of 5 mg/m² and 10 mg/m², respectively. The resulting mixture was coated to give a gelatin coverage of 0.5 g/m².

(OC Layer)

The layer was provided by coating the mixture of 0.5 g/m² of gelatin, 40 mg/m² of an amorphous $SiO_2$ matting agent having an average particle size of about 3.5 μm, 0.1 g/m² of methanol silica, 100 mg/m² of polyacrylamide, 20 mg/m² of silicone oil, and as coating aids, 5 mg/m² of a fluorine surface active agent shown by the following structural formula (e) and 100 mg/m² of sodium dodecylbenzenesulfonate.

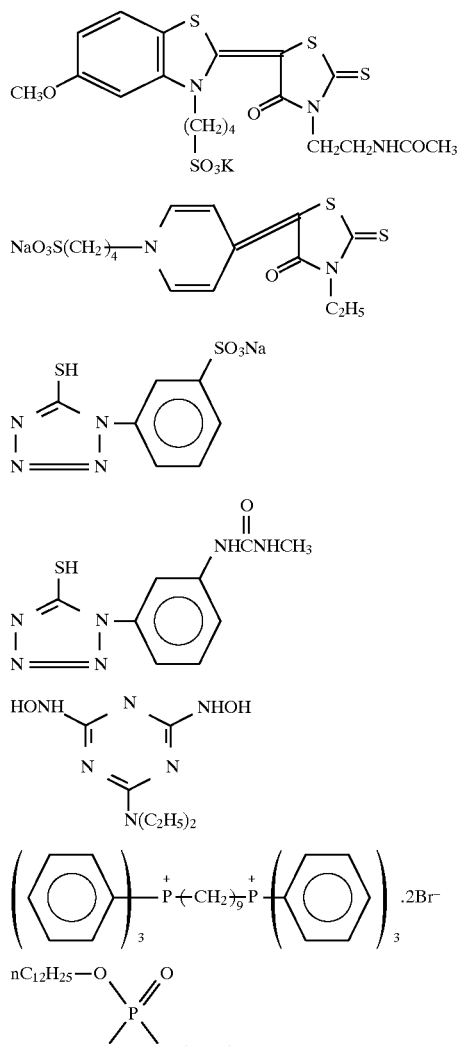

The thus-obtained coated samples each had a back layer and a back protective layer having the following compositions.

| (Formulation of Back Layer) | |
|---|---|
| Gelatin | 3 g/m² |
| Latex: Polyethyl acrylate | 2 g/m² |
| Surface active agent: Sodium p-dodecylbenzenesulfonate | 40 mg/m² |
| $CH_2=CHSO_2CH_2CONH\!-\!\!\!\underset{CH_2=CHSO_2CH_2CONH\!-\!\!\!}{\phantom{X}}\!\!(CH_2)_2$ | 110 mg/m² |
| $SnO_2$/Sb (weight ratio: 90/10, average particle size: 0.20 μm) | 200 mg/m² |
| Dye: Mixture of Dye (a), Dye (b) and Dye (c) | |
| Dye (a) | 70 mg/m² |
| Dye (b) | 70 mg/m² |
| Dye (c) | 90 mg/m² |

Dye (a)

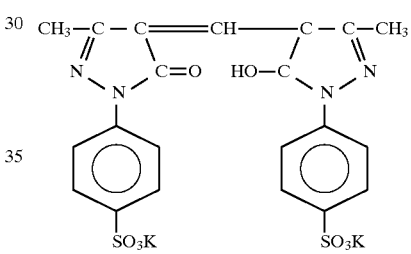

Dye (b)

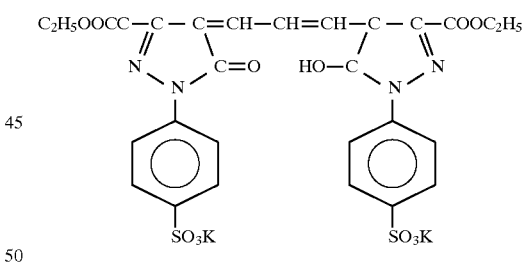

Dye (c)

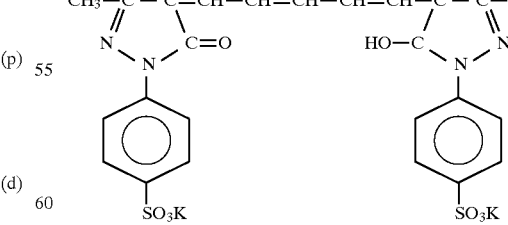

(Back Protective Layer)

| Gelatin | 0.8 mg/m² |
|---|---|
| Polymethyl methacrylate fine particles (average particle size: 4.5 μm) | 30 mg/m² |
| Dihexyl-α-sulfosuccinate sodium salt | 15 mg/m² |

-continued

| | |
|---|---|
| Sodium p-dodecylbenzenesulfonate | 15 mg/m² |
| Sodium acetate | 40 mg/m² |

Samples shown in Tables 3-1 and 3-2 were prepared as described above.

TABLE 3-1

| Sample No. | Solid Dispersion of Hydrazide Compound | Remarks |
|---|---|---|
| 1-1 | K-1 | Comparison |
| 1-2 | K-2 | Comparison |
| 1-3 | K-3 | Comparison |
| 1-4 | K-4 | Comparison |
| 1-5 | K-16 | Invention |
| 1-6 | K-17 | Invention |
| 1-7 | K-18 | Invention |
| 1-8 | K-19 | Invention |
| 1-9 | K-20 | Invention |
| 1-10 | K-21 | Invention |
| 1-11 | K-22 | Invention |
| 1-12 | K-23 | Invention |
| 1-13 | K-24 | Invention |
| 1-14 | K-25 | Invention |

TABLE 3-2

| Sample No. | Solid Dispersion of Hydrazide Compound | Remarks |
|---|---|---|
| 1-1' | K-1' | Comparison |
| 1-2' | K-2' | Comparison |
| 1-3' | K-3' | Comparison |
| 1-4' | K-4' | Comparison |
| 1-5' | K-5' | Comparison |
| 1-6' | K-6' | Invention |
| 1-7' | K-7' | Invention |
| 1-8' | K-8' | Invention |
| 1-9' | K-9' | Invention |
| 1-10' | K-10' | Invention |
| 1-11' | K-11' | Invention |
| 1-12' | K-12' | Invention |
| 1-13' | K-13' | Invention |
| 1-14' | K-14' | Invention |
| 1-15' | K-15' | Invention |
| 1-16' | K-16' | Invention |
| 1-17' | K-17' | Invention |
| 1-18' | K-18' | Invention |

Preparation of Developer

Developer A having the following composition was prepared.

| (Developer A) | |
|---|---|
| Sodium hydroxide | 1.71 g |
| Diethylenetriaminepentaacetic acid | 4 g |
| Potassium carbonate | 27.5 g |
| Sodium carbonate | 25.5 g |
| Sodium erythorbate | 30 g |
| N-Methyl-p-aminophenol | 7.5 g |
| KBr | 2 g |
| 5-Methylbenzotriazole | 0.1 g |
| 1-Phenyl-5-mercaptotetrazole | 0.02 g |
| Sodium sulfite | 5 g |
| Glacial acetic acid | 9 g |

Water was added t make 1 l and pH was adjusted to 9.7.

Developer B and Developer C were prepared by adding an acetic acid to Developer A to adjust the pH to 9.4 and adding sodium hydroxide to Developer A to adjust the pH to 10.0, respectively.

Evaluation (1) Exposure and Development

The thus-prepared samples each was exposed to a xenon flash light using a step wedge through an interference filter having a peak at 488 nm for a luminescence time of $10^{-5}$ sec and then developed with Developer A, Developer B or Developer C in an automatic developing machine FG-680AG manufactured by Fuji Photo Film Co., Ltd., at 35° C. for 20 seconds, followed by fixing, water washing and drying. In the processing, the developer and the fixing solution were replenished in an amount of 100 ml and 150 ml, respectively, per 1 m² of the sample.

Fixing Solution A having the following formulation was used as the fixing solution.

| (Fixing Solution A) | |
|---|---|
| Ammonium thiosulfate | 119.7 g |
| Disodium ethylenediaminetetraacetate dihydrate | 0.03 g |
| Sodium thiosulfate pentahydrate | 10.9 g |
| Sodium sulfite | 25.0 g |
| NaOH (as purity) | 12.4 g |
| Glacial acetic acid | 29.1 g |
| Tartaric acid | 2.92 g |
| Sodium gluconate | 1.74 g |
| Aluminum sulfate | 8.4 g |
| pH (adjusted by sulfuric acid or sodium hydroxide) | 4.8 |
| Water to make | 1 l |

(2) Contrast

Contrast obtained upon development with Developer A was expressed as follows. With respect to the index ($\gamma$) for showing the contrast of an image, a point giving (fog+density of 0.1) in a characteristic curve and a point giving (fog+density of 3.0) were connected by a straight line and the gradient of the straight line was shown as the $\gamma$ value. In other words, $\gamma=(3.0-0.1)/[\log(\text{exposure amount necessary for giving density of 3.0})-(\text{exposure amount necessary for giving density of 0.1})]$, and the larger the $\gamma$ value, the higher the contrast.

(3) Photographic Sensitivity

The sensitivity was expressed by a reciprocal of the exposure amount necessary for giving a density of 1.5 and the sensitivity of each sample was calculated as a relative value to the sensitivity of a comparative sample taken as 100. The larger the value, the higher the sensitivity.

(4) Dependency of Photographic Property on pH of Developer

Using the sensitivity values obtained on development with Developer B and with Developer C, dependency of the sensitivity on the pH of the developer was calculated.

pH Dependency of sensitivity ($\Delta S_{1.5}$)=$S_{1.5}$ (Developer C)-$S_{1.5}$ (Developer B)

The smaller the value, the smaller the dependency on pH of the developer, that is, the higher the processing stability.

(5) Aging Stability of Light-Sensitive Material

Samples stored at a temperature of 60° C. and a humidity of 65% for 3 days each was developed with Developer A according to the above-described method, and the sensitivity was measured. Change in the photographic property between the sample obtained above and the sample stored at room temperature and normal humidity for 3 days was determined according to the following formula.

Change in sensitivity due to aging ($\Delta S_{1.5}$) = $S_{1.5}$ (sample stored at a temperature of 60° C. and a humidity of 65% for 3 days) − $S_{1.5}$ (sample stored at room temperature and normal humidity for 3 days)

The closer to 0 the value, the higher the aging stability of the light-sensitive material.

The results obtained are shown in Tables 4-1 and 4-2.

TABLE 4-1

| Sample No. | γ | Dependency on pH of Developer ($\Delta S_{1.5}$) | Aging Stability of Light-Sensitive Material ($\Delta S_{1.5}$) | Remarks |
|---|---|---|---|---|
| 1-1 | 13 | 0.21 | −0.02 | Comparison |
| 1-2 | 11 | 0.25 | −0.04 | Comparison |
| 1-3 | 15 | 0.16 | −0.09 | Comparison |
| 1-4 | 11 | 0.15 | −0.06 | Comparison |
| 1-5 | 19 | 0.04 | 0 | Invention |
| 1-6 | 20 | 0.04 | −0.01 | Invention |
| 1-7 | 21 | 0.03 | 0 | Invention |
| 1-8 | 19 | 0.06 | 0 | Invention |
| 1-9 | 19 | 0.05 | 0 | Invention |
| 1-10 | 21 | 0.03 | −0.01 | Invention |
| 1-11 | 22 | 0.04 | −0.01 | Invention |
| 1-12 | 22 | 0.04 | −0.01 | Invention |
| 1-13 | 21 | 0.05 | 0 | Invention |
| 1-14 | 19 | 0.03 | −0.01 | Invention |

TABLE 4-2

| Sample No. | γ | Dependency on pH of Developer ($\Delta S_{1.5}$) | Aging Stability of Light-Sensitive Material ($\Delta S_{1.5}$) | Remarks |
|---|---|---|---|---|
| 1-1' | 13 | 0.21 | −0.02 | Comparison |
| 1-2' | 12 | 0.22 | −0.03 | Comparison |
| 1-3' | 15 | 0.15 | −0.07 | Comparison |
| 1-4' | 15 | 0.16 | −0.09 | Comparison |
| 1-5' | 14 | 0.14 | −0.06 | Comparison |
| 1-6' | 25 | 0.02 | −0.01 | Invention |
| 1-7' | 25 | 0.04 | −0.02 | Invention |
| 1-8' | 24 | 0.03 | −0.02 | Invention |
| 1-9' | 22 | 0.02 | −0.02 | Invention |
| 1-10' | 23 | 0.02 | −0.01 | Invention |
| 1-11' | 23 | 0.02 | −0.02 | Invention |
| 1-12' | 24 | 0.03 | −0.02 | Invention |
| 1-13' | 25 | 0.02 | −0.01 | Invention |
| 1-14' | 23 | 0.04 | −0.01 | Invention |
| 1-15' | 23 | 0.03 | −0.01 | Invention |
| 1-16' | 24 | 0.04 | −0.01 | Invention |
| 1-17' | 25 | 0.02 | −0.01 | Invention |
| 1-18' | 25 | 0.03 | −0.02 | Invention |

Results

Only when the hydrazide compound of the present invention was used as a nucleating agent, a light-sensitive material for argon laser scanner, which provides ultrahigh contrast and exhibits high processing stability with a developer having a low pH and also exhibits excellent aging stability could be obtained.

EXAMPLE 3

Preparation of Silver Halide Photographic Light-Sensitive Material (Preparation of Emulsion)

Emulsion B was prepared as follows.

Emulsion B was prepared in the same manner as Emulsion A except for adding 1 mg/mol-Ag of a selenium sensitizer having the following structural formula, 1 mg/mol-Ag of sodium thiosulfate and 4 mg/mol-Ag of chloroauric acid and performing chemical sensitization to have optimal sensitivity at 60° C.

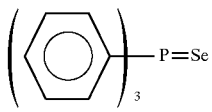

(Preparation of Coated Sample)

Samples were prepared in the same manner as in Example 2 except for adding $2\times10^{-4}$ mol/mol-Ag of Compound (S-3) shown below in place of the sensitizing dye used in EM Layer of Example 2 and for using Emulsion B as the emulsion in EM Layer.

Compound (S-3)

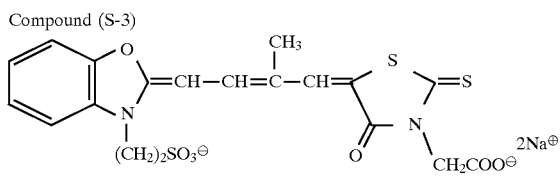

Evaluation (1) Exposure and Development

The thus-prepared samples each was exposed to a xenon flash light using a step wedge through an interference filter having a peak at 633 nm for a luminescence time of $10^{-6}$ sec. Then, samples each was developed with Developer A described in Example 2 in an automatic developing machine FG-680AG manufactured by Fuji Photo Film Co., Ltd., at 35° C. for 20 seconds, and subjected to fixing (same as in Example 2), water washing and drying. In the processing, the developer and the fixing solution each was replenished in an amount of 100 ml per 1 $m^2$ of the sample.

Evaluation of the contrast, the dependency of sensitivity on pH of the developer and the aging stability of the light-sensitive material was performed in the same manner as in Example 2.

Results

Similarly to Example 2, only when the hydrazide compound of the present invention was used as a nucleating agent, a light-sensitive material for helium-neon laser scanner, which provides ultrahigh contrast and exhibits high processing stability with a developer having a low pH and also exhibits excellent aging stability could be obtained.

EXAMPLE 4

Preparation of Silver Halide Photographic Light-Sensitive Material

Samples were prepared in the same manner as in Example 2 except for using Compound (S-4) shown below in place of the sensitizing dye used in EM Layer of Example 2.

Compound (S-4):

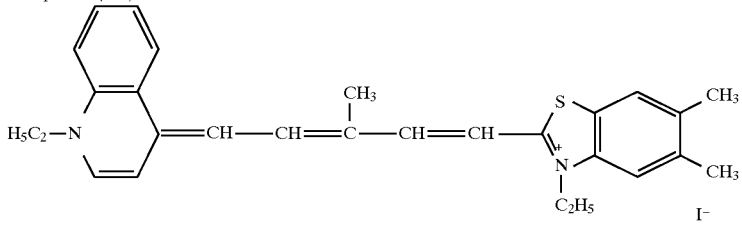

Evaluation

The thus-prepared samples each was exposed to a xenon flash light using a step wedge through an interference filter having a peak at 780 nm for a luminescence time of $10^{-6}$ sec. Then, samples each was developed with Developer A described in Example 2 in an automatic developing machine FG-680AG manufactured by Fuji Photo Film Co., Ltd., at 35° C. for 20 seconds, and subjected to fixing (same as in Example 2), water washing and drying. In the processing, the developer and the fixing solution each was replenished in an amount of 100 ml per 1 $m^2$ of the sample.

Evaluation of the contrast, the dependency of sensitivity on pH of the developer and the aging stability of the light-sensitive material was performed in the same manner as in Example 2.

Results

Similarly to Example 2, only when the hydrazide compound of the present invention was used as a nucleating agent, a light-sensitive material for semiconductor laser scanner, which provides ultrahigh contrast and exhibits high processing stability with a developer having a low pH and also exhibits excellent aging stability could be obtained.

EXAMPLE 5

Preparation of Silver Halide Photographic Light-Sensitive Material

Samples were prepared in the same manner as in Example 2 except for using Compound (S-5) shown below in place of the sensitizing dye used in EM Layer in Example 2.

Compound (S-5):

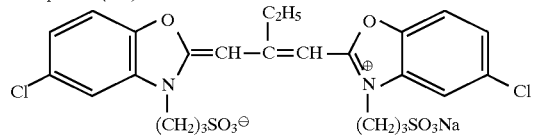

Evaluation

The thus-prepared samples each was exposed to a tungsten light of 3,200° K. through a step wedge. Then, samples each was developed with Developer A described in Example 2 in an automatic developing machine FG-680AG manufactured by Fuji Photo Film Co., Ltd., at 35° C. for 20 seconds, and subjected to fixing (same as in Example 2), water washing and drying. In the processing, the developer and the fixing solution each was replenished in an amount of 100 ml per 1 $m^2$ of the sample.

Evaluation of the contrast, the dependency of sensitivity on pH of the developer and the aging stability of the light-sensitive material was performed in the same manner as in Example 2.

Results

Similarly to Example 2, only when the hydrazide compound of the present invention was used as a nucleating agent, a light-sensitive material for photographing, which provides ultrahigh contrast and exhibits high processing stability with a developer having a low pH and also exhibits excellent aging stability could be obtained.

EXAMPLE 6

Preparation of Silver Halide Photographic Light-Sensitive Material (Preparation of Emulsion C)

To a 1.5% aqueous gelatin solution kept at 38° C., containing sodium chloride, $3\times10^{-5}$ mol/mol-Ag of Compound Z shown below and $5\times10^{-3}$ mol/mol-Ag of 4-hydroxy-6-methyl-1,3,3a,7-tetrazaindene and having a pH of 2.0, an aqueous silver nitrate solution and an aqueous sodium chloride solution containing $5\times10^{-5}$ mol/mol-Ag of $K_2Ru(NO)Cl_5$ were added simultaneously in an amount of half the silver amount of the final grain by a double jet method at an electric potential of 95 mV over 3 minutes and 30 seconds to prepare core grains having a size of 0.12 $\mu$m. Thereafter, an aqueous silver nitrate solution and an aqueous sodium chloride solution containing $5\times10^{-5}$ mol/mol-Ag of $K_2Ru(NO)Cl_5$ were added in the same manner as above over 7 minutes to prepare silver chloride cubic grains having an average grain size of 0.13 $\mu$m (coefficient of variation: 12%).

Thereafter, the emulsion was washed with water by a flocculation method well known in the art to remove soluble salts, then gelatin was added, Compound F and phenoxyethanol as antiseptics were added each in an amount of 60 mg/mol-Ag, the pH and the pAg were adjusted to 5.5 and 7.5, respectively, further $4\times10^{-5}$ mol/mol-Ag of chloroauric acid, $1\times10^{-5}$ mol/mol-Ag of the above-described selenium sensitizer and $1\times10^{-5}$ mol/mol-Ag of sodium thiosulfate were added, the mixture was heated at 60° C. for 60 minutes to perform chemical sensitization, and then $1\times10^{-3}$ mol/mol-Ag of 4-hydroxy-6-methyl-1,3,3a,7-tetrazaindene as a stabilizer was added (the final grain was silver chloride having a pH of 5.7 and a pAg of 7.5 and containing $5\times10^{-5}$ mol/mol-Ag of Ru).

Compound Z:

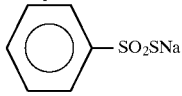

Preparation of Coated Sample
(Silver Halide Emulsion Layer)

To Emulsion C, the following compounds were added, and the mixture was coated on a support having an undercoat layer, which will be described later, to provide a silver halide emulsion layer having a gelatin coated amount of 0.9 g/m$^2$ and a coated silver amount of 2.75 g/m$^2$ on the support.

| | |
|---|---|
| N-Oleyl-N-methyltaurine sodium salt | 19 mg/m$^2$ |
| Solid dispersion of hydrazide compound prepared in Example 1, shown in Table 9 | 15 mg/m$^2$ (as hydrazide compound) |
| Nucleation Accelerator Z | 20 mg/m$^2$ |
| Sodium 3-(5-mercaptotetrazole)-benzene-sulfonate | 11 mg/m$^2$ |
| Compound A | 13 mg/m$^2$ |
| Ascorbic acid | 1 mg/m$^2$ |
| Compound B | 15 mg/m$^2$ |
| Compound C | 70 mg/m$^2$ |
| Acetic acid | in an amount of giving the layer surface pH of from 5.2 to 6.0 |
| Compound D | 950 mg/m$^2$ |
| Compound E (hardening agent) | in an amount of giving a swelling rate with water of 80% |

On the thus-provided emulsion layer, emulsion protective lower and upper layers were coated.

(Emulsion Protective Lower Layer)

To an aqueous gelatin solution, the following compounds were added and the solution was coated to give a gelatin coated amount of 0.8 g/m$^2$.

| | |
|---|---|
| Gelatin (Ca$^{++}$ content: 2,700 ppm) | 0.8 g/m$^2$ |
| Compound F | 1 mg/m$^2$ |
| 1,5-Dihydroxy-2-benzaldoxime | 14 mg/m$^2$ |
| C$_2$H$_5$SO$_2$SNa | 3 mg/m$^2$ |
| Compound C | 3 mg/m$^2$ |
| Sodium p-dodecylbenzenesulfonate | 7 mg/m$^2$ |
| Water-soluble Dye Y | 25 mg/m$^2$ |

(Preparation of Coating Solution for Emulsion Protective Upper Layer and Coating Thereof)

To an aqueous gelatin solution, the following compounds were added, and the solution was coated to give a gelatin coated amount of 0.45 g/m$^2$.

| | |
|---|---|
| Gelatin (Ca$^{++}$ content: 2,700 ppm) | 0.45 g/m$^2$ |
| Amorphous silica matting agent (average particle size: 4.4 μm) | 40 mg/m$^2$ |
| Amorphous silica matting agent (average particle size: 3.6 μm) | 10 mg/m$^2$ |
| Compound F | 1 mg/m$^2$ |
| Compound C | 8 mg/m$^2$ |
| Solid Disperse Dye G$_1$ | 68 mg/m$^2$ |
| Liquid paraffin | 21 mg/m$^2$ |
| Potassium N-perfluoroctanesulfonyl-N-propylglycine | 5 mg/m$^2$ |
| Sodium p-dodecylbenzenesulfonate | 29 mg/m$^2$ |

Then, on the opposite surface of the support, an electrically conductive layer and a back layer described below were coated simultaneously.

(Electrically Conductive Layer)

To an aqueous gelatin solution, the following compounds were added, and the solution was coated to give a gelatin coated amount of 0.06 g/m$^2$.

| | |
|---|---|
| SnO$_2$/Sb (9/1 by weight, average particle size: 0.25 μm) | 186 mg/m$^2$ |
| Gelatin (Ca$^{++}$ content: 2,700 ppm) | 0.06 mg/m$^2$ |
| Sodium p-dodecylbenzenesulfonate | 13 mg/m$^2$ |
| Sodium dihexyl-α-sulfosuccinate | 12 mg/m$^2$ |
| Compound C | 12 mg/m$^2$ |
| Compound F | 1 mg/m$^2$ |

(Back Layer)

To an aqueous gelatin solution, the following compounds were added, and the solution was coated to give a gelatin coated amount of 1.94 g/m$^2$.

| | |
|---|---|
| Gelatin (Ca$^{++}$ content: 3.0 ppm) | 1.94 g/m$^2$ |
| Polymethyl methacrylate fine particle (average particle size: 4.7 μm) | 7 mg/m$^2$ |
| Compound H | 233 mg/m$^2$ |
| Compound I | 21 mg/m$^2$ |
| Compound G | 146 mg/m$^2$ |
| Compound F | 3 mg/m$^2$ |
| Sodium p-dodecylbenzenesulfonate | 68 mg/m$^2$ |
| Sodium dihexyl-α-sulfosuccinate | 21 mg/m$^2$ |
| C$_8$F$_{17}$SO$_3$Li | 4 mg/m$^2$ |
| Potassium N-perfluoroctanesulfonyl-N-propylglycine | 6 mg/m$^2$ |
| Sodium sulfate | 177 mg/m$^2$ |
| Compound E (hardening agent) | in an amount of giving a swelling rate with water of 90% |

(Support and Undercoat Layer)

On both surfaces of a biaxially stretched polyethylene terephthalate support (thickness: 100 μm), undercoat first and second layers having the following compositions were coated.

| (Undercoat First Layer) | |
|---|---|
| Core-shell Type Vinylidene Chloride Copolymer (1) | 15 g |
| 2,4-Dichloro-6-hydroxy-s-triazine | 0.25 g |
| Polystyrene fine particle (average particle size: 3 μm) | 0.05 g |
| Compound M | 0.20 g |
| Colloidal silica (Snowtex ZL, produced by Nissan Chemical KK, particle size: 70 to 100 μm) | 0.12 g |
| Water to make | 100 g |

Further, the coating solution was adjusted to have a pH of 6 by adding 10 wt % of KOH and coated to have a dry thickness of 0.9 μm at a drying temperature of 180° C. for 2 minutes.

| (Undercoat Second Layer) | |
|---|---|
| Gelatin | 1 g |
| Methyl cellulose | 0.05 g |
| Compound J | 0.02 g |
| C$_{12}$H$_{25}$O(CH$_2$CH$_2$O)$_{10}$H | 0.03 g |
| Compound F | 3.5 × 10$^{-3}$ g |
| Acetic acid | 0.2 g |
| Water to make | 100 g |

The thus-obtained coating solution was coated to have a dry thickness of 0.1 μm at a drying temperature of 170° C. for 2 minutes. Thus, a support having undercoat layers was prepared.

Nucleation Accelerator Z:

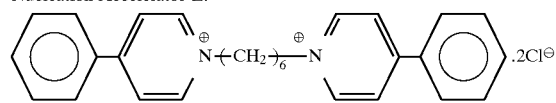

Compound A:

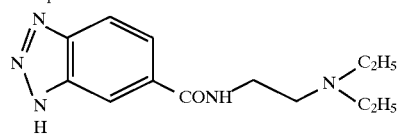

Compound C:

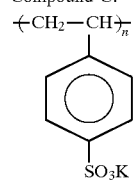

Compound B:

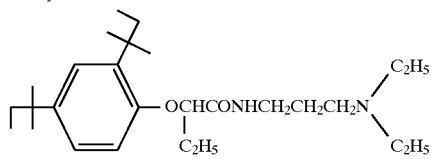

Compound D:

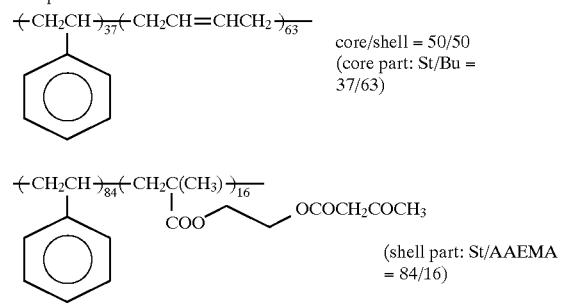

core/shell = 50/50
(core part: St/Bu = 37/63)

(shell part: St/AAEMA = 84/16)

Compound E:

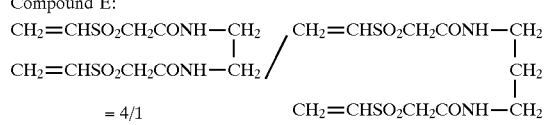

Compound F:

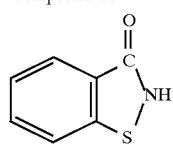

Compound G:

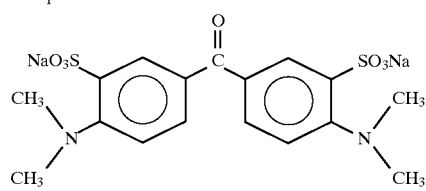

Solid Disperse Dye $G_1$:

-continued

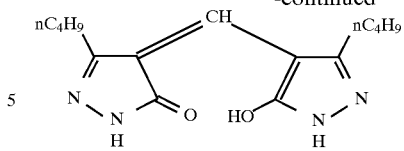

Compound H:

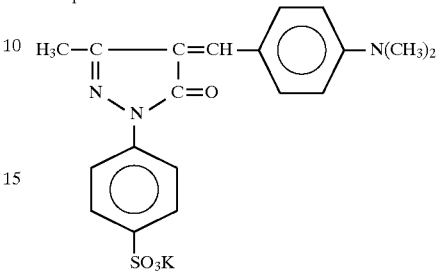

Water-Soluble Dye Y:

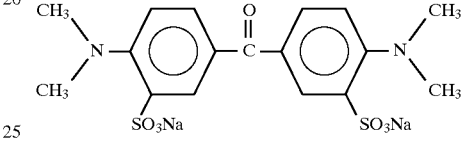

Compound I:

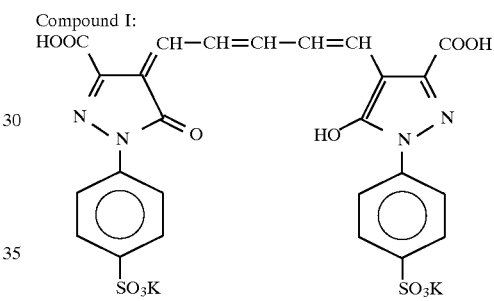

Compound J:

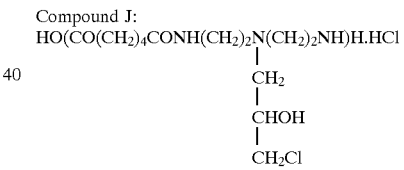

The coating method and the drying conditions were as follows.

Coating Method

On the emulsion surface side of the support having undercoat layers prepared above, an emulsion layer, an emulsion protective lower layer and an emulsion protective upper layer were simultaneously coated on one another in this sequence from the side nearer to the support while keeping at 35° C. and while adding a hardening agent solution by a slide hopper method, and the coated sample was passed through a cold blast set zone (5° C.). Thereafter, on the side opposite to the emulsion surface, an electrically conductive layer and a back layer were simultaneously coated on one another in this sequence from the side nearer to the support similarly while adding a hardening agent solution by the slide hopper method, and the coated sample was passed through a cold blast set zone (5° C.). At the time of passing respective set zones, the coating solution exhibited satisfactory setting property. Subsequently, both surfaces were simultaneously dried in a drying zone under the following conditions. After coating on the back surface side until winding up, the coated sample was transported without coming into contact with a roller and others at all. At this time, the coating rate was 120 m/min.

Drying Condition

After setting, the coated sample was dried by a drying air at 30° C. to give a weight ratio of water/gelatin of 800% and then by drying air at 35° C. and 30% to give the ratio of from 200 to 800%. The blowing of air was continued and 30 seconds after the time when the surface temperature reached 34° C. (regarded as completion of drying), the coated sample was dried by air at 48° C. and 2% for one minute. At this time, the drying time of from the initiation of drying until the water/gelatin ratio reached 800% was 50 seconds, the drying time until the ratio reached from 200 to 800% was 35 seconds and the drying time of from the ratio of 200% until completion of the drying was 5 seconds.

The thus-obtained light-sensitive material was wound up at 23° C. and 40%, cut under the same environment, subjected to humidity conditioning at 40° C. and 10% for 8 hours in a barrier bag of which humidity was conditioned for 6 hours, and then sealed together with a cardboard of which humidity was conditioned at 23° C. and 40% for 2 hours, to prepare a sample.

The humidity in the barrier bag was measured and found to be 40%.

Samples shown in Tables 5-1 and 5-2 were prepared as described above.

TABLE 5-1

| Sample No. | Solid Dispersion of Hydrazide Compound | Remarks |
| --- | --- | --- |
| 2-1 | K-1 | Comparison |
| 2-2 | K-2 | Comparison |
| 2-3 | K-3 | Comparison |
| 2-4 | K-4 | Comparison |
| 2-5 | K-5 | Invention |
| 2-6 | K-6 | Invention |
| 2-7 | K-7 | Invention |
| 2-8 | K-8 | Invention |
| 2-9 | K-9 | Invention |
| 2-10 | K-10 | Invention |
| 2-11 | K-11 | Invention |
| 2-12 | K-12 | Invention |
| 2-13 | K-13 | Invention |
| 2-14 | K-14 | Invention |
| 2-15 | K-15 | Invention |

TABLE 5-2

| Sample No. | Solid Dispersion of Hydrazide Compound | Remarks |
| --- | --- | --- |
| 2-1' | K-1' | Comparison |
| 2-2' | K-2' | Comparison |
| 2-3' | K-3' | Comparison |
| 2-4' | K-4' | Comparison |
| 2-5' | K-5' | Comparison |
| 2-6' | K-19' | Invention |
| 2-7' | K-20' | Invention |
| 2-8' | K-21' | Invention |
| 2-9' | K-22' | Invention |
| 2-10' | K-23' | Invention |
| 2-11' | K-24' | Invention |
| 2-12' | K-25' | Invention |
| 2-13' | K-26' | Invention |
| 2-14' | K-27' | Invention |
| 2-15' | K-28' | Invention |
| 2-16' | K-29' | Invention |
| 2-17' | K-30' | Invention |

TABLE 5-2-continued

| Sample No. | Solid Dispersion of Hydrazide Compound | Remarks |
| --- | --- | --- |
| 2-18' | K-31' | Invention |
| 2-19' | K-32' | Invention |

Evaluation

The above-described samples each was exposed through a step wedge in a printer P-627FM manufactured by Dainippon Screen Mfg. Co., Ltd. Then, the samples each was developed with Developer A described in Example 2 in an automatic developing machine FG-680AG manufactured by Fuji Photo Film Co., Ltd, at 35° C. for 20 seconds, and subjected to fixing (same as in Example 2), water washing and drying. In the processing, the developer and the fixing solution were replenished each in an amount of 100 ml per $m^2$ of the sample.

Evaluation of the contrast, the dependency of sensitivity on pH of the developer and the aging stability of the light-sensitive material was performed in the same manner as in Example 2.

The results obtained are shown in Tables 6-1 and 6-2.

TABLE 6-1

| Sample No. | γ | Dependency on pH of Developer ($\Delta S_{1.5}$) | Aging Stability of Light-Sensitive Material ($\Delta S_{1.5}$) | Remarks |
| --- | --- | --- | --- | --- |
| 2-1 | 9 | 0.11 | −0.01 | Comparison |
| 2-2 | 10 | 0.20 | −0.07 | Comparison |
| 2-3 | 13 | 0.16 | −0.06 | Comparison |
| 2-4 | 10 | 0.21 | −0.06 | Comparison |
| 2-5 | 18 | 0.06 | 0 | Invention |
| 2-6 | 18 | 0.09 | −0.01 | Invention |
| 2-7 | 19 | 0.09 | −0.01 | Invention |
| 2-8 | 21 | 0.07 | 0 | Invention |
| 2-9 | 21 | 0.06 | 0 | Invention |
| 2-10 | 20 | 0.08 | −0.01 | Invention |
| 2-11 | 21 | 0.06 | 0 | Invention |
| 2-12 | 19 | 0.06 | −0.01 | Invention |
| 2-13 | 18 | 0.07 | −0.01 | Invention |
| 2-14 | 18 | 0.06 | 0 | Invention |
| 2-15 | 20 | 0.08 | 0 | Invention |

TABLE 6-2

| Sample No. | γ | Dependency on pH of Developer ($\Delta S_{1.5}$) | Aging Stability of Light-Sensitive Material ($\Delta S_{1.5}$) | Remarks |
| --- | --- | --- | --- | --- |
| 2-1' | 9 | 0.11 | −0.01 | Comparison |
| 2-2' | 11 | 0.28 | −0.10 | Comparison |
| 2-3' | 13 | 0.15 | −0.08 | Comparison |
| 2-4' | 13 | 0.16 | −0.06 | Comparison |
| 2-5' | 13 | 0.18 | −0.08 | Comparison |
| 2-6' | 21 | 0.04 | −0.01 | Invention |
| 2-7' | 21 | 0.06 | −0.02 | Invention |
| 2-8' | 22 | 0.05 | −0.01 | Invention |
| 2-9' | 24 | 0.05 | −0.01 | Invention |
| 2-10' | 23 | 0.03 | −0.01 | Invention |
| 2-11' | 24 | 0.04 | −0.01 | Invention |
| 2-12' | 24 | 0.06 | −0.02 | Invention |
| 2-13' | 21 | 0.04 | −0.02 | Invention |
| 2-14' | 22 | 0.03 | −0.01 | Invention |
| 2-15' | 22 | 0.03 | −0.02 | Invention |
| 2-16' | 23 | 0.05 | −0.02 | Invention |
| 2-17' | 24 | 0.04 | −0.02 | Invention |

TABLE 6-2-continued

| Sample No. | γ | Dependency on pH of Developer ($\Delta S_{1.5}$) | Aging Stability of Light-Sensitive Material ($\Delta S_{1.5}$) | Remarks |
|---|---|---|---|---|
| 2-18' | 24 | 0.04 | −0.01 | Invention |
| 2-19' | 21 | 0.06 | −0.01 | Invention |

Results

Only when the hydrazide compound of the present invention was used as a nucleating agent, a light-sensitive material for dot-to-dot work in a bright room, which provides ultra-high contrast and exhibits high processing stability with a developer having a low pH and also exhibits excellent aging stability could be obtained.

EXAMPLE 7

In Examples 2, 3, 4, 5 and 6, even when Developer D or Developer E having the following composition was used in place of Developer A and Fixing Solution B having the following composition was used in place of Fixing Solution A, similarly to Examples 2, 3, 4, 5 and 6, only when the hydrazide compound of the present invention was used as a nucleating agent, a light-sensitive material which provides ultrahigh contrast and exhibits high processing stability with a developer having a low pH and also exhibits excellent aging stability could be obtained. In examining the dependency of the photographic property on pH of the developer, each developer reduced in the pH by 0.3 with acetic acid or increased in the pH by 0.3 with sodium hydroxide was used.

| (Developer D) | |
|---|---|
| Potassium hydroxide | 40.0 g |
| Diethylenetriaminepentaacetic acid | 2.0 g |
| Potassium carbonate | 60.0 g |
| Sodium metabisulfite | 70.0 g |
| Potassium bromide | 7.0 g |
| Hydroquinone | 40.0 g |
| 5-Methylbenzotriazole | 0.35 g |
| 4-Hydroxymethyl-4-methyl-1-phenyl-3-pyrazolidone | 1.50 g |
| Sodium 2-mercaptobenzimidazole-5-sulfonate | 0.30 |
| Sodium 3-(5-mercaptotetrazol-1-yl)-benzenesulfonate | 0.10 g |
| Sodium erythorbate | 60 g |
| Diethylene glycol | 5.0 g |
| Water to make | 1 l | pH was adjusted by adding potassium hydroxide to 10.65.

(Developer E)

A solid developer as a storing shape was formed into a use solution by adding water to make 10 l.

The solid developer was produced by a method where developer components in the form of solid, corresponding to 10 l portion as a use solution, were packed in a container (average wall thickness: 500 μm, partially: from 200 to 1,000 μm) made of a high density polyethylene. The respective components were mixed prior to the filling in the container.

The composition of the developer as a 10 l use solution and the forms of raw materials are shown in Table 7.

TABLE 7

| Developer No. | Form of Raw Material | |
|---|---|---|
| Sodium hydroxide (99.5%) (purity in the parenthesis) | beads | 115 g |
| Potassium sulfite | raw powder | 718 g |
| Sodium sulfite | raw powder | 350 g |
| Diethylenetriaminepentaacetic acid | | 20 g |
| 5-Methylbenzotriazole | | 3.5 g |
| Sodium 2-mercaptobenzimidazole-5-sulfonate | | 3.0 g |
| Sodium 3-(5-mercaptotetrazol-1-yl) benzenesulfonate | briquetted collectively | 1.0 g |
| Potassium bromide | | 66 g |
| 4-Hydroxymethyl-4-methyl-1-phenyl-3-pyrazolidone | | 15 g |
| Sodium erythorbate | | 60 g |
| Potassium carbonate | raw powder | 620 g |
| Hydroquinone | briquet | 400 g |
| Total weight | | 2,336 g |
| Alkali wt % | | 4.9% |
| pH | | 10.6 |

(Unit (other than pH): g)

With respect to the shape of raw materials, the raw powder was a general industrial product used as it was and the beads and the pellets of alkali metal salt were commercially available products.

The raw materials in the shape of a briquet each was compressed under pressure using a briquetting machine to have an undefined Rugby ball form having a length of approximately from 4 to 6 mm, and the briquet was crushed and used. With respect to components of small amount, respective components were blended and then briquetted.

(Fixing Solution B)

The following solid agent and liquid agent were formed into a use solution by adding water to make 10 l. The fixing solution used was obtained by packing the following formulation, including both the solid agent part and the liquid agent part, in a container (average wall thickness: 500 μm, width: from 200 to 1,000 μm) made of a high density polyethylene. After dissolving, the amount of solution was 10 l and the pH was 4.85.

| Solid agent part: | |
|---|---|
| Ammonium thiosulfate | 1,200 g |
| Sodium thiosulfate | 150 g |
| Sodium acetate | 400 g |
| Sodium metabisulfite | 200 g |
| Liquid agent part: | |
| Aluminum sulfate (27%) | 300 g |
| Sulfuric acid (75%) | 30 g |
| Sodium gluconate | 20 g |
| EDTA | 0.3 g |
| Citric acid | 40 g |

The solid agent part was packed after mixing.

EXAMPLE 8

A light-sensitive material was prepared in the same manner as in Example 2 except that the hydrazide compound powder shown in Table 12 was dissolved in methanol and then added to the coating solution. The samples each was developed in the same manner as in Example 2 and evaluated in terms of the contrast and the dependency of sensitivity on pH of the developer.

The results obtained are shown in Tables 8-1 and 8-2.

TABLE 8-1

| Sample No. | Hydrazide Compound | γ | Dependency on pH of Developer ($\Delta S_{1.5}$) | Remarks |
|---|---|---|---|---|
| 3-1 | Comparative Compound 1 | 14 | 0.22 | Comparison |
| 3-2 | Comparative Compound 2 | 12 | 0.26 | Comparison |
| 3-3 | Comparative Compound 3 | 17 | 0.17 | Comparison |
| 3-4 | Comparative Compound 4 | 13 | 0.15 | Comparison |
| 3-5 | 1d | 21 | 0.02 | Invention |
| 3-6 | 3d | 22 | 0.02 | Invention |
| 3-7 | 4d | 23 | 0.02 | Invention |
| 3-8 | 5d | 22 | 0.04 | Invention |
| 3-9 | 6d | 20 | 0.03 | Invention |
| 3-10 | 10d | 23 | 0.02 | Invention |
| 3-11 | 11d | 23 | 0.02 | Invention |
| 3-12 | 12d | 24 | 0.03 | Invention |
| 3-13 | 16d | 22 | 0.03 | Invention |
| 3-14 | 19d | 20 | 0.02 | Invention |

TABLE 8-2

| Sample No. | Hydrazide Compound | γ | Dependency on pH of Developer ($\Delta S_{1.5}$) | Remarks |
|---|---|---|---|---|
| 3-1' | Comparative Compound 1' | 14 | 0.22 | Comparison |
| 3-2' | Comparative Compound 2' | 13 | 0.23 | Comparison |
| 3-3' | Comparative Compound 3' | 16 | 0.14 | Comparison |
| 3-4' | Comparative Compound 4' | 17 | 0.17 | Comparison |
| 3-5' | Comparative Compound 5' | 15 | 0.14 | Comparison |
| 3-6' | 1b' | 26 | 0.01 | Invention |
| 3-7' | 2b' | 27 | 0.02 | Invention |
| 3-8' | 3b' | 25 | 0.01 | Invention |
| 3-9' | 4b' | 24 | 0.01 | Invention |
| 3-10' | 5b' | 25 | 0.01 | Invention |
| 3-11' | 6b' | 24 | 0.01 | Invention |
| 3-12' | 7a' | 26 | 0.02 | Invention |
| 3-13' | 8a' | 27 | 0.01 | Invention |
| 3-14' | 9a' | 25 | 0.02 | Invention |
| 3-15' | 10a' | 24 | 0.02 | Invention |
| 3-16' | 12a' | 26 | 0.02 | Invention |
| 3-17' | 13a' | 27 | 0.01 | Invention |
| 3-18' | 14a' | 28 | 0.01 | Invention |

Results

Similarly to Example 2, only when the hydrazide compound of the present invention was used as a nucleating agent, a light-sensitive material which provides ultrahigh contrast and exhibits high processing stability with a developer having a low pH could be obtained.

EXAMPLE 9

A solution composed of 1.0 g of the respective hydrazine nucleating agent which was used in Example 1 and shown in Table 2-2, 6.0 g of poly(N-tert-butylacrylamide) and 50 ml of ethyl acetate was heated to 60° C. to dissolve the compounds completely. Thereafter, the solution was added to 120 ml of an aqueous solution containing 12 g of gelatin and 0.7 g of sodium dodecylbenzenesulfonate, and stirred with a homogenizer (manufactured by Nippon Seiki Manufacturing Co., Ltd.) at a high rotational speed to obtain an emulsion dispersion of fine particles having an average particle diameter of about 0.2 μm. Then, the emulsion dispersion was heated and distilled under reduced pressure to remove ethyl acetate. A photographic light-sensitive material was prepared in the same manner as in Example 3, except for using the thus obtained solid dispersion of hydrazine nucleating agent. The photographic characteristics of the photographic light-sensitive material was evaluated in the same manner as in Example 3. As a result, only when the hydrazide compound of the present invention was used as a nucleating agent, a light-sensitive material for helium-neon laser scanner which provides ultrahigh contrast and exhibits high processing stability with a developer having a low pH and also exhibits excellent aging stability could be obtained.

While the invention has been described in detail and with reference to specific examples thereof, it will be apparent to one skilled in the art that various changes and modifications can be made therein without departing from the spirit and scope thereof.

What is claimed is:

1. A silver halide photographic light-sensitive material containing a hydrazide compound represented by the following formula (I), (II), (I'), or (II'):

$$A_1\text{-}(B)b_1 \qquad (I)$$

$$L_o\text{-}\{A_2\text{-}(B)b_2\}m_1 \qquad (II)$$

wherein $A_1$ represents a substituted or unsubstituted benzene ring, $A_2$ represents an arylene group, B represents a group represented by the following formula (III), $b_1$ represents an integer of from 3 to 6, $L_o$ represents a di-, tri-, tetra-, penta- or hexavalent linking group, $b_2$ represents an integer of from 1 to 5, and $m_1$ represents an integer of from 2 to 6, provided that when $b_2$ is 1, $m_1$ represents an integer of from 3 to 6:

$$-L_1-Ar_1-NHNH-G_1-R_1 \qquad (III)$$

wherein $G_1$ represents a carbonyl group, an oxalyl group, a sulfonyl group or a phosphoryl group, $R_1$ represents a hydrogen atom or a block group, $Ar_1$ represents an aromatic group and $L_1$ represents a linking group:

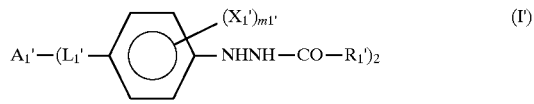

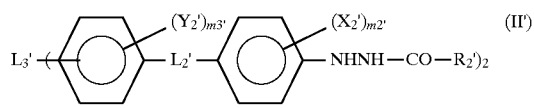

wherein $A_1'$ represents a substituted or unsubstituted benzene ring, $L_1'$, $L_2'$ and $L_3'$ each represents a divalent linking group, $X_1'$, $X_2'$ and $Y_2'$ each represents a substituent, $m_1'$, $m_2'$ and $m_3'$ each represents an integer of from 0 to 4, $R_1'$ and $R_2'$ each represents a hydrogen atom or a block group, provided that at least one of two $R_1'$ groups in formula (I') and at least one of two $R_2'$ groups in formula (II') each represents a substituted alkyl group substituted by one or more fluorine atoms; and wherein $L_3'$ does not contain a cationic group.

2. The silver halide photographic light-sensitive material of claim 1, wherein said hydrazide compound is represented by formula (I') or (II') and at least one of two $L_1'$ groups in formula (I') and at least one of two $L_2'$ groups in formula (II') each is an —SO₂NH group.

3. The silver halide photographic light-sensitive material of claim 2, wherein at least one $R_1'$ group in formula (I') and at least one $R_2'$ group in formula (II') each is a trifluoromethyl group or a difluoromethyl group.

* * * * *